US 8,415,356 B2

(12) United States Patent
Khanzhin et al.

(10) Patent No.: US 8,415,356 B2
(45) Date of Patent: Apr. 9, 2013

(54) ISOQUINOLINONE DERIVATIVES AS NK3 ANTAGONISTS

(75) Inventors: Nikolay Khanzhin, Humlebæk (DK); Karsten Juhl, Greve (DK); Søren Møller Nielsen, Hillerød (DK); Klaus Bæk Simonsen, Odense (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 12/997,282

(22) PCT Filed: Jun. 19, 2009

(86) PCT No.: PCT/EP2009/057660
§ 371 (c)(1),
(2), (4) Date: Feb. 15, 2011

(87) PCT Pub. No.: WO2009/156339
PCT Pub. Date: Dec. 30, 2009

(65) Prior Publication Data
US 2011/0130407 A1 Jun. 2, 2011

Related U.S. Application Data

(60) Provisional application No. 61/074,740, filed on Jun. 23, 2008.

(30) Foreign Application Priority Data

Jun. 23, 2008 (DK) .................. 2008 00859

(51) Int. Cl.
*C07D 401/04* (2006.01)
*A61K 31/4725* (2006.01)

(52) U.S. Cl. .............. 514/253.05; 514/255.05; 514/256; 514/309; 544/322; 544/363; 544/405; 546/141

(58) Field of Classification Search .................. None
See application file for complete search history.

(56) References Cited

U.S. PATENT DOCUMENTS

| 7,834,008 B2 | 11/2010 | Kehler et al. |
| 2009/0143402 A1 | 6/2009 | Simonsen et al. |

FOREIGN PATENT DOCUMENTS

| WO | 95/32948 A1 | 12/1995 |
| WO | 2005/014575 A1 | 2/2005 |
| WO | 2006/050991 A1 | 5/2006 |
| WO | 2006/050992 A1 | 5/2006 |
| WO | 2006/130080 A1 | 12/2006 |
| WO | 2008/131779 A1 | 11/2008 |
| WO | 2009130240 | 10/2009 |
| WO | 2010/028655 A1 | 3/2010 |
| WO | 2010/045948 A1 | 4/2010 |

OTHER PUBLICATIONS

Albert and Potts, Jan. 1, 2006, Expert Opinion on Therapeutic Patents, Informa Healthcare, GB, vol. 16, No. 7, pp. 925-937.
Modi, AR and Usgaonkar, R, Oct. 1979, Ind. J. Chem. vol. 18B, pp. 304-306.
Albert, J. S.; 2004, Neurokinin antagonists and their potential role in treating depression and other stress disorders, Expert Opin. Ther. Patents, 14(10):1421-1433.
Berge, et al., 1977, Pharmaceutical Salts, Journal of Pharmaceutical Sciences; 66:1, 1-19.
Cogan D.A. et al., 1999, Asymmetric Synthesis of Chiral Amines by Highly Diastereoselective 1,2-Additions of Organometallic Reagents to N-tert-Butanesulfinyl Imines, Tetranedron., 29(55): 8883-5904.
Daoui, Samira. et al., Jul. 1, 1998. Involvement of Tachykinin NK3 Receptors in Citric Acid-induced Cough and Bronchial Responses in Guinea Pigs, Am. .J. .Respir. Crit. Care. Med., 158(1): 42-48.
Evangelista, S., 2005, Talnetant GlaxoSmithKline, Curr. Opion. .Invest. .Drug., 6(7): 717-721.
Fioramonti, J. et al., 2003, "Intestinal anti-nociceptive behaviour of NK3 receptor antagonism in conscious rats: evidence to support a peripheral mechanism of action" Neurogastroenterol Motil., 15(4): 363-369.
Kemel, M. L. et al., Mar. 1, 2002, Facilitation of Endogenous Tachykinins of the NMDA-Evoked Release of Acetylcholine after Acute and Chronic Suppression of Dopaminergic Transmission of the Matrix of the Rat Striatum, J. Neurosci., 22(5): 1929-1936.
Langlois, X. et al., Nov. 1, 2001, Use of the B-Imager for Rapid ex Vivo Autoradiography Exemplified with Central Nervous System Penetrating Neurokinin 3 Antagonists, J. Pharm. Exp. Ther., 299(2): 712-717.
Liu, G., et al., Feb. 4, 1999, Synthesis of Enantiomerically Pure N-tert-Butanesulfinyl Imines (tert-Butanesulfinimines) by the Direct Condensation of tret-Butanesulfinamide with Aldehydes and Ketones, J. Org. Chem., 64(4): 1278-1284.

(Continued)

*Primary Examiner* — Zinna Northington Davis
(74) *Attorney, Agent, or Firm* — Stephen G. Kalinchak; Mary Catherine Di Nunzio; Kitae T. Lim

(57) ABSTRACT

Isoquinolone derivatives of the general formula I are provided. The compounds are NK3 antagonists and useful for the treatment of e.g. psychosis and schizophrenia.

23 Claims, No Drawings

OTHER PUBLICATIONS

Maubach, K. A. et al., 1998, Tachykinins May Modify Spontaneous Epileptiform Activity in the Rat Enthorhinal Cortex in Vitro by Activating Gabaergic Inhibition, Neuroscience., 83(4):1047-1062.

Mazelin, L., et al., 1998, Comparative Effects of Nonpeptide TachyKinin Receptor Antagonists of Experimental Gut Inflammation in Rats and Guinea-Pigs, Life Sci., 63(4):293-304.

Meltzer, et al., Jun. 2004, Placebo-Controlled Evaluation of Four Novel Compounds for the Treatment of Schizophrenia and Schizoaffective Disorder, Am. J. Psychiatry, 161(6):975-984.

Spooren et al., nk3 receptor antagonists: the next generation of antipsychotics?, 2005, Nature Reviews, 4(12):967-975.

Fioramonti, J. et al., Aug. 2003, Intestinal anti-nociceptive behaviour of NK3 receptor antagonism in conscious rats: evidence to support a peripheral mechanism of action, Neurogastroenterol. Motil., 15(4):363-369.

ISOQUINOLINONE DERIVATIVES AS NK3 ANTAGONISTS

CROSS-REFERENCE TO RELATED APPLICATIONS

The present application is a §371 U.S. National Stage Application of International Application No. PCT/EP2009/057660, filed June 19, 2009, which claims the benefit of priority under 35 U.S.C. §119(a)-(d) of Danish Patent Application No. PA200800859, filed June 23, 2008, and which claims the benefit of priority under 35 U.S.C. §119(e) of U.S. Provisional Application No. 61/074,740, filed June 23, 2008. Each of these applications is hereby incorporated by reference in its entirety.

FIELD OF THE INVENTION

The present invention relates to compounds useful in therapy, in particular in the treatment of psychosis, to compositions comprising said compounds, and to methods of treating diseases comprising the administration of said compounds.

BACKGROUND OF THE INVENTION

The currently approved antipsychotic drugs share the common feature of reducing the dopamine signalling in the brain. This is achieved through either a dopamine D2 receptor antagonistic or partial agonistic effect. The first generation antipsychotics (also referred to as "typical") are often associated with extra-pyrimidal side effects wherefore the use of these agents have diminished. Second generation or "atypical" antipsychotics in addition to the D2 receptor affinity have affinity to the serotonin receptor 2A (5-HT$_{2A}$). Some atypical antipsychotics in addition have affinity for the 5-HT$_{2C}$, 5-HT$_6$, or 5-HT$_7$ receptors. Atypical antipsychotics give rise to fewer extra-pyramidal side effects, but are still hampered by weight gain and QT$_C$ effects. Examples of atypicals are clozapine, olanzapine and risperidone.

More recently, neurokinin receptors have been suggested as targets for CNS diseases [Albert, *Expert Opin. Ther. Patents,* 14, 1421-1433, 2004]. Neurokinins (or tachykinins) are a family of neuropeptides, which include substance P(SP), neurokinin A (NKA), and neurokinin B (NKB). The biological effects of these substances are primarily effected through binding to and activation of the three neurokinin receptors NK1, NK2, and NK3. Although some cross reactivity probably exists, SP has the highest affinity and is believed to be the endogenous ligand for NK1, and likewise for NKA and NK2, and for NKB and NK3.

NK3 is primarily expressed centrally in regions including cortical regions, such as frontal, parietal and cingulated cortex; nuclei of the amygdala, such as the basal, central and lateral nuclei; the hippocampus; and mesencephalon structures, such as ventral tegmental area, substantia nigra pars compacta, and dorsal raphe nuclei [Spooren et al, *Nature Reviews,* 4, 967-975, 2005]. The NK3 receptor is expressed on dopaminergic neurons, and Spooren et al has suggested that the antipsychotic effects of NK3 antagonists are mediated by an inhibition of the dopamine tone, particularly at the D2 receptor combined with a reduction of the serotonergic tone, particularly at the 5-HT$_{2A}$ receptor.

Two structurally distinct NK3 antagonists, namely talnetant and osanetant, have been clinically tested for antipsychotic, and in particular antischizophrenic effects.

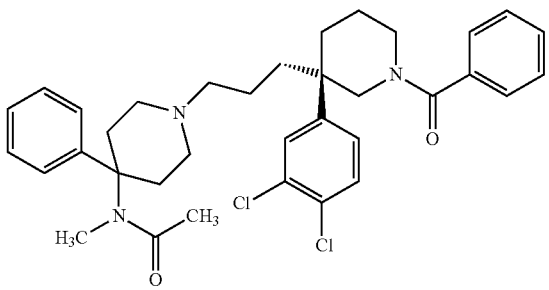

Osanetant

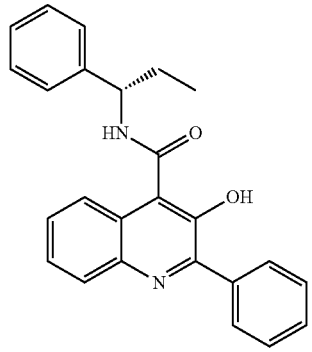

Talnetant

Osanetant proved superior to placebo in clinical trials, in particular on positive symptoms of psychosis, i.e. delusions, hallucinations and paranoia [*Am. J. Psychiatry,* 161, 2004, 975-984]. Similarly, talnetant has been shown in clinical trials to ameliorate the cognitive behaviour of schizophrenics [*Curr. Opion. Invest. Drug,* 6, 717-721, 2005]. Nevertheless, both compounds are hampered by poor pharmacokinetic and pharmacodynamic properties including poor solubility, poor bioavailability, relatively high clearance, and poor blood-brain barrier penetration [*Nature reviews,* 4, 967-975, 2005]. These results lend support to the notion that the NK3 receptor is a promising target for the treatment of e.g. psychosis, however emphasising the need for identifying compounds with adequate pharmacokinetic and pharmacodynamic properties.

WO95/32948 discloses a range of quinoline derivatives, including talnetant as NK3 antagonists.

More recently, WO 2006/130080 discloses compounds having the core structure

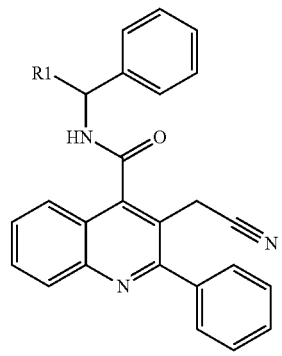

which compounds are said to be NK3 antagonists; and WO 2006/050991 and WO 2006/050992 disclose further quinolinecarboxamides derivatives, which derivatives are said to be NK3 antagonists.

WO 2005/014575 discloses compounds of the formula

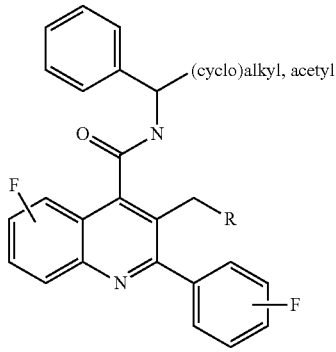

wherein R represents N-containing heterocycles, i.e. pyrazolyl, triazolyl and tetrazolyl.

Finally, *Ind. J. Chem. Section B*, 18B, 304-306, 1979 discloses a study on the synthesis of compounds with the following core structure

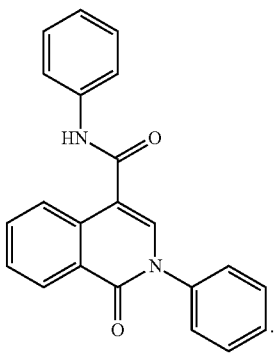 [SMILES: O=C(Nc1ccccc1)c1cn(-c2ccccc2)c(=O)c2ccccc12]

After the priority date of the present application, WO 2008/131779 has published disclosing NK3 antagonists of the general structure

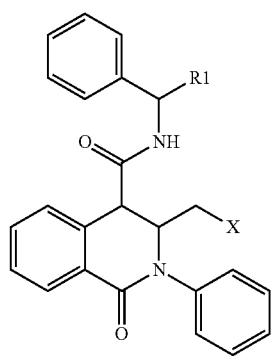

wherein R1 represents inter alia alkyl, and wherein X represents a cyclic moiety with at least one nitrogen ring atom.

SUMMARY OF THE INVENTION

The present inventors have surprisingly found that certain isoquinolinone derivatives are potent NK3 antagonists, which may as such be used in the treatment of e.g. psychosis. Accordingly, in one embodiment the invention relates to a compound of formula I

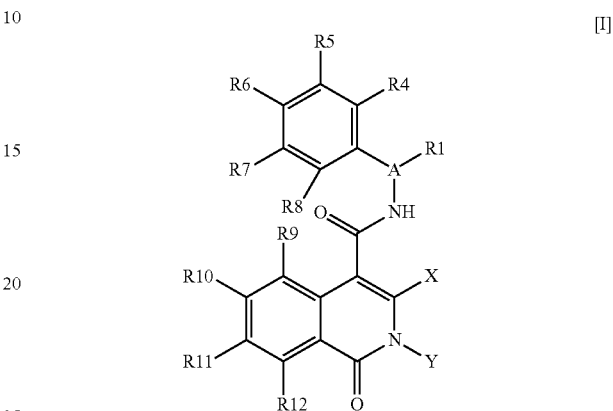

wherein A represent N, CH or $CR^1$;

each $R^1$ independently represents hydrogen, $C_{1-6}$alkyl, $C_{2-6}$alkenyl, $C_{2-6}$alkynyl, —C(O)—$C_{1-6}$alkyl, —C(O)—$C_{2-6}$alkenyl, —C(O)—$C_{2-6}$alkynyl, —C(O)—O—$C_{1-6}$alkyl, —C(O)—O—$C_{2-6}$alkenyl, —C(O)—O—$C_{2-6}$alkynyl or phenyl, wherein said phenyl, $C_{1-6}$alkyl, $C_{2-6}$alkenyl or $C_{2-6}$alkynyl is optionally substituted with one or more substituents selected from halogen, hydroxyl, halo$C_{1-6}$alkyl, nitro, $C_{1-6}$alkoxy, and $NR^2R^3$;

X represents hydrogen, $C_{1-6}$alkyl or —$CR^aR^b$—X', wherein X' represents a monocyclic saturated moiety having 5-6 ring atoms one of which is N and wherein one or two additional ring atom may be a hetero atom selected from N, O and S, which monocyclic ring may be substituted with one or more substituent W, wherein W is selected from $C_{1-6}$alkyl, $C_{2-6}$alkenyl, $C_{2-6}$alkynyl, or (═O);

$R^a$ and $R^b$ each individually represent hydrogen, —$CH_3$ or halogen;

Y represents a hetero aromatic moiety having 5-6 ring atoms, wherein 1-4 of said ring atoms are selected from N, O and S, which hetero aromatic moiety may optionally be benzofused, and which hetero aromatic moiety may be substituted with one or more substituent Z, wherein Z is selected from $C_{1-6}$alkyl, $C_{2-6}$alkenyl, $C_{2-6}$alkynyl, cyano, halogen, hydroxy, $C_{1-6}$alkoxy, $C_{1-6}$haloalkyl, and $NR^2R^3$; wherein each of $R^2$ and $R^3$ independently represents hydrogen, $C_{1-6}$alkyl, $C_{2-6}$alkenyl, $C_{2-6}$alkynyl, hydroxy$C_{1-6}$alkyl, or halo$C_{1-6}$alkyl;

each of $R^4$-$R^8$ and $R^9$-$R^{12}$ independently represents hydrogen, $C_{1-6}$alkyl, $C_{2-6}$alkenyl, $C_{2-6}$alkynyl, halogen, $NR^2R^3$, hydroxy, cyano, nitro, $C_{1-6}$alkoxy, halo$C_{1-6}$alkyl or hydroxy$C_{1-6}$alkyl;

and pharmaceutically acceptable salts thereof.

In one embodiment, the invention relates to a compound of formula I and pharmaceutically acceptable salts thereof for use in therapy.

In one embodiment, the invention relates to a pharmaceutical composition comprising a compound of formula I and pharmaceutically acceptable salts thereof.

In one embodiment, the invention relates to a method of treatment, which methods comprise the administration of a therapeutically effective amount of a compound of formula I and pharmaceutically acceptable salts thereof to a patient in need thereof.

In one embodiment, the invention relates to the use of a compound of formula I and pharmaceutically acceptable salts thereof in the manufacture of a medicament.

In one embodiment, the invention relates to a compound of formula I and pharmaceutically acceptable salts thereof for use in the treatment of diseases.

DEFINITIONS

In the present context, "alkyl" is intended to indicate a straight, branched and/or cyclic saturated hydrocarbon. In particular, "$C_{1-6}$alkyl" is intended to indicate such hydrocarbon having 1, 2, 3, 4, 5, or 6 carbon atoms. Examples of $C_{1-6}$alkyl include methyl, ethyl, propyl, butyl, pentyl, hexyl, cyclopropyl, cyclobutyl, cyclopentyl, cyclohexyl, 2-methyl-propyl, tert.-butyl, and cyclopropylmethyl.

In the present context, "alkenyl" is intended to indicate a non-aromatic, straight, branched and/or cyclic hydrocarbon comprising at least one carbon-carbon double bond. In particular, "$C_{2-6}$alkenyl" is intended to indicate such hydrocarbon having 2, 3, 4, 5, or 6 carbon atoms. Examples of $C_{2-6}$alkenyl include ethenyl, 1-propenyl, 2-propenyl, 1-butenyl, 2-butenyl, 3-butenyl, and cyclohexenyl.

In the present context, "alkynyl" is intended to indicate a non-aromatic, straight, branched and/or cyclic hydrocarbon comprising at least one carbon-carbon triple bond and optionally also one or more carbon-carbon double bonds. In particular "$C_{2-6}$alkynyl" is intended to indicate such hydrocarbon having 2, 3, 4, 5, or 6 carbon atoms. Examples of $C_{2-6}$alkynyl include ethynyl, 1-propynyl, 2-propynyl, 1-butynyl, 2-butynyl and 3-butyryl.

In the present context "halogen" is intended to indicate members of the $7^{th}$ group of the periodic system, e.g. fluoro, chloro, bromo, and iodo.

In the present context, "alkoxy" is intended to indicate a moiety of the formula —OR', wherein R' indicates alkyl as defined above. In particular "$C_{1-6}$alkoxy" is intended to indicate such moiety wherein the alkyl part has 1, 2, 3, 4, 5, or 6 carbon atoms.

In the present context, haloalkyl is intended to indicate an alkyl as defined above substituted with one or more halogens. In particular, halo$C_{1-6}$alkyl is intended to indicate a moiety wherein the alkyl part has 1, 2, 3, 4, 5 or 6 carbon atoms. One example of haloalkyl is trifluoromethyl.

In the present context, pharmaceutically acceptable salts include pharmaceutical acceptable acid addition salts, pharmaceutically acceptable metal salts, ammonium and alkylated ammonium salts. Acid addition salts include salts of inorganic acids as well as organic acids.

Examples of suitable inorganic acids include hydrochloric, hydrobromic, hydroiodic, phosphoric, sulfuric, sulfamic, nitric acids and the like.

Examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutical acceptable inorganic or organic acid addition salts include the pharmaceutically acceptable salts listed in J. Pharm. Sci. 1977, 66, 2, which is incorporated herein by reference.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, a "ring atom" is intended to indicate the atoms constituting a ring, and ring atoms are selected from C, N, O and S. As an example, benzene and toluene both have 6 carbons as ring atoms whereas pyridine has 5 carbons and 1 nitrogen as ring atoms.

In the present context, a "mono-cyclic moiety" is intended to indicate a ring formed structure comprising only one ring.

In the present context, the term "therapeutically effective amount" of a compound means an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician.

In the present context, the term "treatment" and "treating" means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. Nonetheless, prophylactic (preventive) and therapeutic (curative) treatments are two separate aspects of the invention. The patient to be treated is preferably a mammal, in particular a human being.

DETAILED DESCRIPTION OF THE INVENTION

In one embodiment, the invention provides compounds (i.e. the compounds of the invention) according to formula I

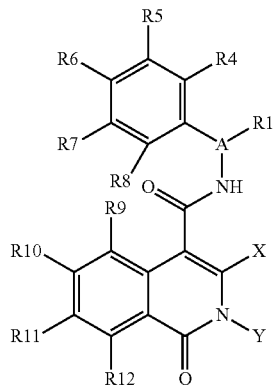

wherein A represent N, CH or CR$^1$;
each R$^1$ independently represents hydrogen, C$_{1-6}$alkyl, C$_{2-6}$alkenyl, C$_{2-6}$alkynyl, —C(O)—C$_{1-6}$alkyl, —C(O)—C$_{2-6}$alkenyl, —C(O)—C$_{2-6}$alkynyl, —C(O)—O—C$_{1-6}$alkyl, —C(O)—O—C$_{2-6}$alkenyl, —C(O)—O—C$_{2-6}$alkynyl or phenyl, wherein said phenyl, C$_{1-6}$alkyl, C$_{2-6}$alkenyl or C$_{2-6}$alkynyl is optionally substituted with one or more substituents selected from halogen, hydroxyl, haloC$_{1-6}$alkyl, nitro, C$_{1-6}$alkoxy, and NR$^2$R$^3$;
X represents hydrogen, C$_{1-6}$alkyl or —CR$^a$R$^b$—X', wherein X' represents a monocyclic saturated moiety having 5-6 ring atoms one of which is N and wherein one or two additional ring atom may be a hetero atom selected from N, O and S, which monocyclic ring may be substituted with one or more substituent W, wherein W is selected from C$_{1-6}$alkyl, C$_{2-6}$alkenyl, C$_{2-6}$alkynyl, or (═O);
R$^a$ and R$^b$ each individually represent hydrogen, —CH$_3$ or halogen;
Y represents a hetero aromatic moiety having 5-6 ring atoms, wherein 1-4 of said ring atoms are selected from N, O and S, which hetero aromatic moiety may be benzo-fused, and which hetero aromatic moiety may be substituted with one or more substituent Z, wherein Z is selected from C$_{1-6}$alkyl, C$_{2-6}$alkenyl, C$_{2-6}$alkynyl, cyano, halogen hydroxy, C$_{1-6}$alkoxy, C$_{1-6}$haloalkyl, and NR$^2$R$^3$; wherein each of R$^2$ and R$^3$ independently represents hydrogen, C$_{1-6}$alkyl, C$_{2-6}$alkenyl, C$_{2-6}$alkynyl, hydroxyC$_{1-6}$alkyl, or haloC$_{1-6}$alkyl;
each of R$^4$-R$^8$ and R$^9$-R$^{12}$ independently represent hydrogen, C$_{1-6}$alkyl, C$_{2-6}$alkenyl, C$_{2-6}$alkynyl, halogen, NR$^2$R$^3$, hydroxy, cyano, nitro, C$_{1-6}$alkoxy, haloC$_{1-6}$alkyl or hydroxyC$_{1-6}$alkyl;
and pharmaceutically acceptable salts thereof.

Example of such mono-cyclic saturated moieties having 5-6 ring atoms one of which is N and wherein one or two additional ring atoms may be a hetero atom selected from N, O, S include piperazinyl, pyrrolidinyl, imidazolidinyl, pyrazolidinyl, piperidyl, morpholinyl, and thiomorpholinyl.

Examples of such hetero aromatic moiety having 5-6 ring atoms, wherein 1-4 of said ring atoms are selected from N, O and S include furyl, pyranyl, isothiazolyl, pyrimidinyl, pyridazinyl, 4H-[1,2,4]triazolyl, thienyl, thiazolyl, 1H-pyrazolyl, 1H-imidazolyl, [1,3,4]thiadiazolyl, thiazolyl, oxazolyl, isoxazolyl, pyrrolyl, pyridyl, and pyrazinyl.

In one embodiment, A represents CH.
In one embodiment, R$^1$ represents C$_{1-6}$alkyl, such as ethyl, cyclopropyl, cyclobutyl or cyclopentyl.
In one embodiment, X represents H, methyl or —CH$_2$—X', wherein X' represents a monocyclic moiety selected from piperazinyl and pyrrolidinyl, wherein said monocyclic moiety may be substituted with one or more substituents W, wherein W is selected from C$_{1-6}$alkyl and (═O). In particular, X represents methyl.

In one embodiment, Y represents a hetero aromatic moiety having 5-6 ring atoms, wherein 1-3 of said ring atoms are selected from N, O and S, and which hetero aromatic moiety may be substituted with one or more substituent Z, wherein Z is selected from C$_{1-6}$alkyl, cyano, halogen C$_{1-6}$alkoxy, and NR$^2$R$^3$; wherein each of R$^2$ and R$^3$ independently represents hydrogen or C$_{1-6}$alkyl. In particular, Y represents a hetero aromatic moiety selected from 4H-[1,2,4]triazolyl, thienyl, thiazolyl, 1H-pyrazolyl, 1H-imidazolyl, [1,3,4]thiadiazolyl, thiazolyl, oxazolyl, isoxazolyl, pyrrolyl, pyridyl, or pyrazinyl.

In one embodiment, R$^4$-R$^8$ independently represent hydrogen or halogen. In particular, R$^7$ represents halogen and R$^4$, R$^5$, and R$^8$ represent hydrogen.

In one embodiment, R$^9$-R$^{12}$ independently represent hydrogen or halogen. In particular, R$^9$-R$^{11}$ represent hydrogen and R$^{12}$ represents halogen.

In one embodiment, the compounds of the invention are defined by formula I' or I''

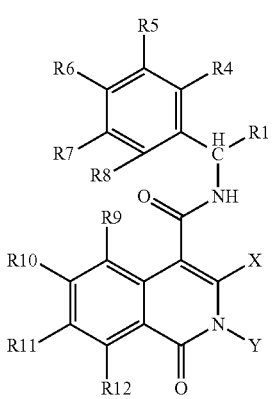

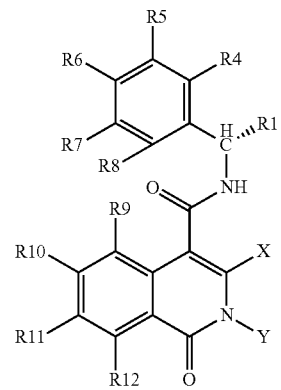

wherein R$^1$ represents C$_{1-6}$alkyl;
X represents hydrogen, C$_{1-6}$alkyl or —CH$_2$—X', wherein X' represents piperazinyl or pyrrolidinyl, wherein said piperazinyl or pyrrolodinyl may be substituted with one or more substituents W, wherein W is selected from C$_{1-6}$alkyl and (═O);
wherein Y represents a hetero aromatic moiety having 5-6 ring atoms, wherein 1-4 of said ring atoms are selected from N, O and S, which hetero aromatic moiety may optionally be benzo-fused, and which hetero aromatic moiety may be substituted with one or more substituent Z, wherein Z is selected from $C_{1-6}$alkyl, cyano, halogen, hydroxy, $C_{1-6}$alkoxy, $C_{1-6}$haloalkyl, and $NR^2R^3$; wherein each of $R^2$ and $R^3$ independently represents hydrogen or $C_{1-6}$alkyl;
each of $R^4$-$R^8$ and $R^9$-$R^{12}$ independently represent hydrogen, halogen $C_{1-6}$alkoxy or $C_{1-6}$haloalkyl;
and pharmaceutically acceptable salts thereof.

In one embodiment, wherein the compounds of the invention are defined by formula I' or I'', $R^1$ represents ethyl, cyclopropyl, or cyclobutyl.

In one embodiment, wherein the compounds of the invention are defined by formula I' or I'', $R^1$ represents ethyl, cyclopropyl, or cyclobutyl; X represents $C_{1-6}$alkyl, such as methyl; Y represents a hetero aromatic moiety having 5-6 ring atoms, wherein 1-4 of said ring atoms are selected from N, O and S, and which hetero aromatic moiety may be substituted with one or more substituent Z, wherein Z is selected from $C_{1-6}$alkyl, cyano, halogen hydroxy, $C_{1-6}$alkoxy, $C_{1-6}$haloalkyl, and $NR^2R^3$; wherein each of $R^2$ and $R^3$ independently represents hydrogen or $C_{1-6}$alkyl; $R^4$-$R^8$ independently represent hydrogen or halogen; and $R^9$-$R^{12}$ independently represent hydrogen or halogen. In particular, $R^7$ represents halogen and $R^4$, $R^5$, and $R^8$ represent hydrogen; and $R^9$-$R^{11}$ represent hydrogen and $R^{12}$ represents halogen. In particular, Y represents a hetero aromatic moiety selected from 4H-[1,2,4]triazolyl, thienyl, thiazolyl, 1H-pyrazolyl, 1H-imidazolyl, [1,3,4]thiadiazolyl, thiazolyl, oxazolyl, isoxazolyl, pyrrolyl, pyridyl, or pyrazinyl.

In one embodiment, compounds of the invention are selected from a list comprising 1a  3-Methyl-1-oxo-2-pyridin-3-yl-1,2-dihydro-isoquinoline-4-carboxylic acid ((S)-1-phenyl-propyl)-amide
1b  3-Methyl-1-oxo-2-[1,2,4]triazol-4-yl-1,2-dihydro-isoquinoline-4-carboxylic acid ((S)-1-phenyl-propyl)-amide
1c  3-Methyl-1-oxo-2-thiophen-3-yl-1,2-dihydro-isoquinoline-4-carboxylic acid ((S)-1-phenyl-propyl)-amide
2a  8-Fluoro-3-methyl-1-oxo-2-pyridin-3-yl-1,2-dihydro-isoquinoline-4-carboxylic acid [(S)-cyclopropyl-(3-fluoro-phenyl)-methyl]-amide
2aa 8-Fluoro-3-methyl-2-(5-methyl-isoxazol-3-yl)-1-oxo-1,2-dihydro-isoquinoline-4-carboxylic acid [(S)-cyclopropyl-(3-fluoro-phenyl)-methyl]-amide
2ab 8-Fluoro-3-methyl-2-(5-methyl-[1,3,4]thiadiazol-2-yl)-1-oxo-1,2-dihydro-isoquinoline-4-carboxylic acid [(S)-cyclopropyl-(3-fluoro-phenyl)-methyl]-amide
2ac  8-Fluoro-3-methyl-1-oxo-2-pyrrol-1-yl-1,2-dihydro-isoquinoline-4-carboxylic acid [(S)-cyclopropyl-(3-fluoro-phenyl)-methyl]-amide
2ad  8-Fluoro-3-methyl-2-(5-methyl-thiazol-2-yl)-1-oxo-1,2-dihydro-isoquinoline-4-carboxylic acid [(S)-cyclopropyl-(3-fluoro-phenyl)-methyl]-amide
2ae 2-(3-Cyano-thiophen-2-yl)-8-fluoro-3-methyl-1-oxo-1,2-dihydro-isoquinoline-4-carboxylic acid [(S)-cyclopropyl-(3-fluoro-phenyl)-methyl]-amide
2af  8-Fluoro-2-isoxazol-3-yl-3-methyl-1-oxo-1,2-dihydro-isoquinoline-4-carboxylic acid [(S)-cyclopropyl-(3-fluoro-phenyl)-methyl]-amide
2b  8-Fluoro-3-methyl-1-oxo-2-pyridin-2-yl-1,2-dihydro-isoquinoline-4-carboxylic acid [(S)-cyclopropyl-(3-fluoro-phenyl)-methyl]-amide
2c  8-Fluoro-3-methyl-1-oxo-2-pyrazin-2-yl-1,2-dihydro-isoquinoline-4-carboxylic acid [(S)-cyclopropyl-(3-fluoro-phenyl)-methyl]-amide
2d 2-(6-Chloro-pyridin-3-yl)-8-fluoro-3-methyl-1-oxo-1,2-dihydro-isoquinoline-4-carboxylic acid [(S)-cyclopropyl-(3-fluoro-phenyl)-methyl]-amide
2e 8-Fluoro-2-(6-methoxy-pyridin-3-yl)-3-methyl-1-oxo-1,2-dihydro-isoquinoline-4-carboxylic acid [(S)-cyclopropyl-(3-fluoro-phenyl)-methyl]-amide
2f  2-(2-Amino-pyridin-3-yl)-8-fluoro-3-methyl-1-oxo-1,2-dihydro-isoquinoline-4-carboxylic acid [(S)-cyclopropyl-(3-fluoro-phenyl)-methyl]-amide
2j  8-Fluoro-2-(2-fluoro-pyridin-3-yl)-3-methyl-1-oxo-1,2-dihydro-isoquinoline-4-carboxylic acid [(S)-cyclopropyl-(3-fluoro-phenyl)-methyl]-amide
2k  8-Fluoro-3-methyl-1-oxo-2-pyrimidin-5-yl-1,2-dihydro-isoquinoline-4-carboxylic acid
[(S)-cyclopropyl-(3-fluoro-phenyl)-methyl]-amide
2l  8-Fluoro-3-methyl-2-(6-methyl-pyridin-3-yl)-1-oxo-1,2-dihydro-isoquinoline-4-carboxylic acid [(S)-cyclopropyl-(3-fluoro-phenyl)-methyl]-amide
2m  8-Fluoro-3-methyl-2-(2-methyl-pyridin-3-yl)-1-oxo-1,2-dihydro-isoquinoline-4-carboxylic acid [(S)-cyclopropyl-(3-fluoro-phenyl)-methyl]-amide
2n  8-Fluoro-2-(6-fluoro-pyridin-3-yl)-3-methyl-1-oxo-1,2-dihydro-isoquinoline-4-carboxylic acid [(S)-cyclopropyl-(3-fluoro-phenyl)-methyl]-amide
2o 8-Fluoro-3-methyl-2-(4-methyl-pyridin-3-yl)-1-oxo-1,2-dihydro-isoquinoline-4-carboxylic acid [(S)-cyclopropyl-(3-fluoro-phenyl)-methyl]-amide
2p 8-Fluoro-3-methyl-2-(5-methyl-pyridin-3-yl)-1-oxo-1,2-dihydro-isoquinoline-4-carboxylic acid [(S)-cyclopropyl-(3-fluoro-phenyl)-methyl]-amide
2r  8-Fluoro-3-methyl-2-(4-methyl-thiazol-2-yl)-1-oxo-1,2-dihydro-isoquinoline-4-carboxylic acid [(S)-cyclopropyl-(3-fluoro-phenyl)-methyl]-amide
2s  2-(1,3-Dimethyl-1H-pyrazol-4-yl)-8-fluoro-3-methyl-1-oxo-1,2-dihydro-isoquinoline-4-carboxylic acid [(S)-cyclopropyl-(3-fluoro-phenyl)-methyl]-amide
2t  8-Fluoro-3-methyl-2-(2-methyl-imidazol-1-yl)-1-oxo-1,2-dihydro-isoquinoline-4-carboxylic acid [(S)-cyclopropyl-(3-fluoro-phenyl)-methyl]-amide
2u  8-Fluoro-3-methyl-1-oxo-2-[1,2,4]triazol-4-yl-1,2-dihydro-isoquinoline-4-carboxylic acid [(S)-cyclopropyl-(3-fluoro-phenyl)-methyl]-amide
2v  2-(5-Ethyl-[1,3,4]thiadiazol-2-yl)-8-fluoro-3-methyl-1-oxo-1,2-dihydro-isoquinoline-4-carboxylic acid [(S)-cyclopropyl-(3-fluoro-phenyl)-methyl]-amide
2w  8-Fluoro-3-methyl-1-oxo-2-thiazol-2-yl-1,2-dihydro-isoquinoline-4-carboxylic acid [(S)-cyclopropyl-(3-fluoro-phenyl)-methyl]-amide
2x  2-(1H-Benzoimidazol-2-yl)-8-fluoro-3-methyl-1-oxo-1,2-dihydro-isoquinoline-4-carboxylic acid [(S)-cyclopropyl-(3-fluoro-phenyl)-methyl]-amide
2y  2-(3,5-Dimethyl-[1,2,4]triazol-4-yl)-8-fluoro-3-methyl-1-oxo-1,2-dihydro-isoquinoline-4-carboxylic acid [(S)-cyclopropyl-(3-fluoro-phenyl)-methyl]-amide
2z  2-(2,5-Dimethyl-2H-pyrazol-3-yl)-8-fluoro-3-methyl-1-oxo-1,2-dihydro-isoquinoline-4-carboxylic acid [(S)-cyclopropyl-(3-fluoro-phenyl)-methyl]-amide
3a  8-Fluoro-3-methyl-1-oxo-2-pyridin-3-yl-1,2-dihydro-isoquinoline-4-carboxylic acid [(S)-cyclobutyl-(3-fluoro-phenyl)-methyl]-amide
3b  8-Fluoro-3-methyl-1-oxo-2-pyrazin-2-yl-1,2-dihydro-isoquinoline-4-carboxylic acid [(S)-cyclobutyl-(3-fluoro-phenyl)-methyl]-amide
3c  8-Fluoro-3-methyl-2-(5-methyl-isoxazol-3-yl)-1-oxo-1,2-dihydro-isoquinoline-4-carboxylic acid [(S)-cyclobutyl-(3-fluoro-phenyl)-methyl]-amide
3d  8-Fluoro-2-(6-hydroxy-pyridin-3-yl)-3-methyl-1-oxo-1,2-dihydro-isoquinoline-4-carboxylic acid [(S)-cyclobutyl-(3-fluoro-phenyl)-methyl]-amide 4a  8-Fluoro-3-methyl-1-oxo-2-pyridin-3-yl-1,2-dihydro-isoquinoline-4-carboxylic acid ((S)-cyclobutyl-phenyl-methyl)-amide 5a  8-Fluoro-3-methyl-1-oxo-2-pyridin-3-yl-1,2-dihydro-isoquinoline-4-carboxylic acid [(S)-cyclopropyl-(3,4-difluoro-phenyl)-methyl]-amide 5b  8-Fluoro-3-methyl-1-oxo-2-pyridin-3-yl-1,2-dihydro-isoquinoline-4-carboxylic acid [(S)-cyclobutyl-(4-fluoro-phenyl)-methyl]-amide 5c  8-Fluoro-3-methyl-1-oxo-2-pyridin-3-yl-1,2-dihydro-isoquinoline-4-carboxylic acid [(S)-cyclobutyl-(3,4-difluoro-phenyl)-methyl]-amide 6a  3-(4-tert-Butyl-piperazin-1-ylmethyl)-8-fluoro-1-oxo-2-pyridin-3-yl-1,2-dihydro-isoquinoline-4-carboxylic acid [(S)-cyclopropyl-(3-fluoro-phenyl)-methyl]-amide 6b  8-Fluoro-1-oxo-3-(2-oxo-pyrrolidin-1-ylmethyl)-2-pyridin-3-yl-1,2-dihydro-isoquinoline-4-carboxylic acid [(S)-cyclopropyl-(3-fluoro-phenyl)-methyl]-amide 7a  4-({[(S)-Cyclopropyl-(3-fluoro-phenyl)-methyl]-amino}-methyl)-7,8-difluoro-3-methyl-2-pyridin-3-yl-2H-isoquinolin-1-one 5d  N'-(3-Methyl-1-oxo-2-pyridin-3-yl-1,2-dihydro-isoquinoline-4-carbonyl)-N-phenyl-hydrazinecarboxylic acid methyl ester 7b  7,8-Difluoro-3-methyl-1-oxo-2-pyrazin-2-yl-1,2-dihydro-isoquinoline-4-carboxylic acid [(S)-cyclopropyl-(3-fluoro-phenyl)-methyl]-amide 5e  8-Fluoro-3-methyl-1-oxo-2-pyridin-3-yl-1,2-dihydro-isoquinoline-4-carboxylic acid [(S)-cyclopropyl-(3,5-difluoro-phenyl)-methyl]-amide 5f 8-Fluoro-3-methyl-1-oxo-2-pyridin-3-yl-1,2-dihydro-isoquinoline-4-carboxylic acid [(S)-cyclopropyl-(4-fluoro-phenyl)-methyl]-amide 7c  6,8-Difluoro-3-methyl-1-oxo-2-pyridin-3-yl-1,2-dihydro-isoquinoline-4-carboxylic acid [(S)-cyclobutyl-(3-fluoro-phenyl)-methyl]-amide 3e  2-(6-Bromo-pyridin-3-yl)-8-fluoro-3-methyl-1-oxo-1,2-dihydro-isoquinoline-4-carboxylic acid [(S)-cyclobutyl-(3-fluoro-phenyl)-methyl]-amide 2ag  8-Fluoro-3-methyl-2-(1-methyl-1H-pyrazol-3-yl)-1-oxo-1,2-dihydro-isoquinoline-4-carboxylic acid [(S)-cyclopropyl-(3-fluoro-phenyl)-methyl]-amide 3f 8-Fluoro-3-methyl-2-(1-methyl-1H-pyrazol-3-yl)-1-oxo-1,2-dihydro-isoquinoline-4-carboxylic acid [(S)-cyclobutyl-(3-fluoro-phenyl)-methyl]-amide 8a  8-Hydroxy-3-methyl-1-oxo-2-pyridin-3-yl-1,2-dihydro-isoquinoline-4-carboxylic acid [(S)-cyclopropyl-(3-fluoro-phenyl)-methyl]-amide.

Further, the compounds of the invention may exist in unsolvated as well as in solvated forms with pharmaceutically acceptable solvents such as water, ethanol and the like. In general, the solvated forms are considered equivalent to the unsolvated forms for the purposes of this invention.

The compounds of the present invention may have one or more asymmetric carbons and it is intended that any optical isomers (i.e. enantiomers or diastereomers), as separated, pure or partially purified optical isomers and any mixtures thereof including racemic mixtures, i.e. a mixture of stereoisomeres, are included within the scope of the invention. In particular, when A represents CH or CR$^1$, A may be an optical centre giving rise to two optical isomers, an R form and an S form. In one embodiment, the compounds of the present invention have the S form.

In a particular embodiment, the compounds of the present invention have the following absolute configuration around A, A being CH

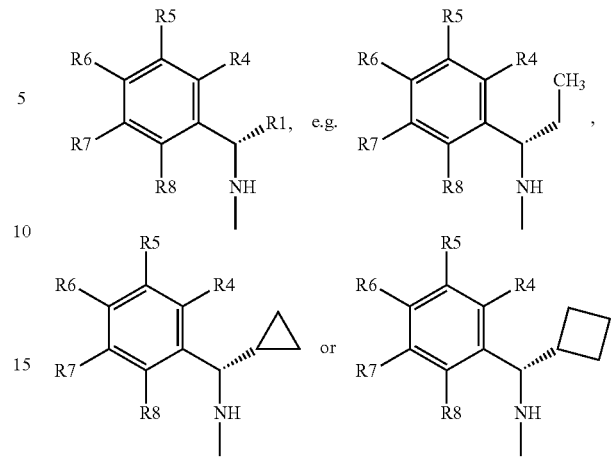

In this context is understood that when specifying the enantiomeric form, then the compound is in enantiomeric excess, e.g. essentially in a pure form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

NK3 receptor antagonists have been implicated in various diseases in addition to psychosis and schizophrenia discussed above. Langlois et al in *J. Pharm. Exp. Ther.*, 299, 712-717, 2001, concludes that NK3 antagonists may be applicable in CNS diseases in general, and in anxiety and depression in particular. Yip et al in *Br. J. Phar.*, 122, 715-722, 1997 further implicates NK3 antagonists in diverse brain functions, such as cortical processing, learning and memory, neuroendocrine and behavioral regulation. Additional studies have shown that NKB and NK3 receptors are involved in pain, and that NK3 antagonists have an antinociceptive and analgesic effect [Fioramonti, *Neurogastroenterol. Motil.*, 15, 363-369, 2003].

Mazelin et al in *Life Sci.*, 63, 293-304, 1998 show that NK3 antagonists have an effect in gut inflammation and concludes that such antagonists may be used in the treatment of irritable bowel syndrome (IBS). In addition, NK3 antagonists have in in vivo models been demonstrated to be useful in the treatment of airway related diseases, such as asthma, airway hyperresponsiveness, cough, and bronchorestriction [Daoui, *Am. J. Respir. Crit. Care Med.*, 158, 42-48, 1998]. Maubach et al in *Neurosci.*, 83, 1047-1062, 1998 show that NKB and the NK3 agonist senktide increase the frequency and duration of epileptiform discharges, and thus by inference that NK3 antagonists have a anticonvulsive potential. Finally, Kernel et al in *J. Neurosci.*, 22, 1929-1936, 2002, suggests the use of NK3 antagonists in the treatment of Parkinson's Disease.

Accordingly, clinical, pre-clinical, in vivo and in vitro studies support that NK3 receptor antagonists are of relevance for the treatment of various disorders including psychosis, schizophrenia, depression, anxiety, cognitive impairment, obesity, Alzheimer's disease, Parkinson's disease, pain, convulsions, cough, asthma, airway hyperresponsiveness, microvascular hypersensitivity, bronchoconstriction, gut inflammation, and inflammatory bowel syndrome.

Schizophrenia may be classified into subgroups. The paranoid type is characterised by delusions and hallucinations and absence of thought disorder, disorganized behavior and affective flattening. The disorganized type, which is also named 'hebephrenic schizophrenia' in the ICD, in which thought disorder and flat affect are present together. The catatonic type, in which prominent psychomotor disturbances are evident, and symptoms may include catatonic stupor and waxy flexibility. The undifferentiated type in which psychotic symptoms are present but the criteria for paranoid, disorganized, or catatonic types have not been met. The symptoms of schizophrenia normally manifest themselves in three broad categories, i.e. positive, negative and cognitive symptoms. Positive symptoms are those, which represent an "excess" of normal experiences, such as hallucinations and delusions. Negative symptoms are those where the patient suffers from a lack of normal experiences, such as anhedonia and lack of social interaction. The cognitive symptoms relate to cognitive impairment in schizophrenics, such as lack of sustained attention and deficits in decision making. The current antipsychotics are fairly successful in treating the positive symptoms but fare less well for the negative and cognitive symptoms. Contrary to that, NK3 antagonists have been shown clinically to improve on both positive and negative symptoms in schizophrenics [*Am. J. Psychiatry*, 161, 975-984, 204], and according to the above discussion they are also expected to deliver an effect on the cognitive symptoms.

Cognitive impairment include a decline in cognitive functions or cognitive domains, e.g. working memory, attention and vigilance, verbal learning and memory, visual learning and memory, reasoning and problem solving e.g. executive function, speed of processing and/or social cognition. In particular, cognitive impairment may indicate deficits in attention, disorganized thinking, slow thinking, difficulty in understanding, poor concentration, impairment of problem solving, poor memory, difficulties in expressing thoughts and/or difficulties in integrating thoughts, feelings and behaviour, or difficulties in extinction of irrelevant thoughts.

In one embodiment, the present invention relates to the compounds of the present invention for use in therapy.

In one embodiment, the present invention relates to a method of treating a disease selected from psychosis; schizophrenia; schizophreno form disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; post traumatic stress disorder; dementia; agitation and delirium in elderly; and inflammatory bowel syndrome the method comprising the administration of a therapeutically effective amount of a compound of the present invention to a patient in need thereof.

In one embodiment, the present invention relates to a method for the treatment of schizophrenia, the method comprising the administration of a therapeutically effective amount of a compound of the present invention to a patient in need thereof. In particular, said treatment includes the treatment of the positive, negative and/or cognitive symptoms of schizophrenia.

In one embodiment, the present invention relates to a method of treating cognitive impairment, the method comprising the administration of a therapeutically effective amount of a compound of the present invention to a patient in need thereof. In particular, said cognitive impairment is manifested as a decline in working memory, attention and vigilance, verbal learning and memory, visual learning and memory, reasoning and problem solving e.g. executive function, speed of processing and/or social cognition.

The antipsychotic effect of typical and atypical anti-psychotics, in particular D2 antagonists is exerted via an inhibition of the post-synaptic D2 receptors. Pre-synaptic D2 autoreceptors, however, are also affected by the administration of these compounds giving rise to an increase in the dopamine neuron firing rate, which, in fact, counteracts the antipsychotic effects. The increased firing rate continues until the effect of the pre-synaptic auto-receptors is blocked (the depolarization block), typically after approximately 3 weeks of chronic treatment with typical or atypical anti-psychotics. This model explains the up to 3 weeks delay of clinical effect normally seen when D2 antagonist treatment is initiated. NK3 antagonists seem to inhibit the increase in the dopamine neuron firing mediated by the pre-synaptic D2 auto-receptors brought about by D2 antagonists, wherefore the combined administration of NK3 antagonists and D2 antagonists is expected to give rise to a faster onset of the clinical effect. Moreover, D2 antagonists are known to increase prolactin levels, which may give rise to serious side effects, such as osteoporosis. It is known that NK3 agonists give rise to an increase in prolactin from which it may be deduced that a NK3 antagonist will lower an increased prolactin level, i.e. normalise the prolactin level. A combined use of NK3 antagonists and D2 antagonists may thus address some of the safety aspects associated with D2 antagonists administration. Similarly, NK3 antagonists may be administered together with antagonists/inverse agonists/negative modulators/partial agonists of one or more of the targets dopamine D2 receptor, dopamine D3 receptor, dopamine D4 receptor, phosphodiesterase PDE10, serotonin $5\text{-HT}_{1A}$ receptor, serotonin $5\text{-HT}_{2A}$ receptor, serotonin $5\text{-HT}_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin 5-HT$_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Such combined administration of compounds of the present invention and other anti-psychotic compounds, such as D2 antagonists, D2 partial agonists, PDE10 antagonists, 5-HT$_{2A}$ antagonists, 5-HT$_6$ antagonists or KCNQ4 antagonists may be sequential or concomitant. Examples of D2 antagonists or partial agonists include haloperidol, chlorpromazine, sulpirid, risperidone, ziprasidon, olanzapine, quetiapin, and clozapine.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day, such as 1-100 mg/day or 1-50 mg/day.

In one embodiment, the present invention relates to the use of the compounds of the present invention in the manufacture of a medicament for the treatment of a disease selected from psychosis; schizophrenia; schizophreno form disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; post traumatic stress disorder; dementia; agitation and delirium in elderly; and inflammatory bowel syndrome.

In one embodiment, the present invention relates to the use of a compound of the present invention in the manufacture of a medicament for the treatment of schizophrenia. In particular, said treatment includes the treatment of the positive, negative and/or cognitive symptoms of schizophrenia.

In one embodiment, the present invention relates to the use of a compound of the present invention in the manufacture of a medicament for the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

In one embodiment, the present invention relates to a compound of the present invention for use in the treatment of a disease selected from psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder (cocaine, alcohol, amphetamine etc); schizoid personality disorder; schizoptypal personality disorder; psychosis or schizophrenia associated with major depression, bipolar disorder, Alzheimer's disease or Parkinson's disease; major depression; general anxiety disorder; bipolar disorder (maintenance treatment, recurrence prevention and stabilization); mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; post traumatic stress disorder; dementia; agitation and delirium in elderly; and inflammatory bowel syndrome.

In one embodiment, the present invention relates to a compound of the present invention for use in the treatment of schizophrenia. In particular, said treatment includes the treatment of the positive, negative and/or cognitive symptoms of schizophrenia.

In one embodiment, the present invention relates to a compound of the present invention for use in the treatment of cognitive impairment. In particular, said cognitive impairment is manifested as a decline in working memory, attention and vigilance, verbal learning and memory, visual learning and memory, reasoning and problem solving e.g. executive function, speed of processing and/or social cognition.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19 Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 1 mg, 5 mg, 10 mg, 50 mg 100 mg, 150 mg, 200 mg or 250 mg of a compound of the present invention.

For parenteral routes such as intravenous, intrathecal, intramuscular and similar administration, typically doses are in the order of about half the dose employed for oral administration.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

In one embodiment, the invention relates to a pharmaceutical composition comprising a compound of the present invention together with a second anti-psychotic agent. In one embodiment, said second anti-psychotic agent is selected from antagonists/inverse agonists/negative modulators/partial agonists of the targets dopamine D2 receptor, dopamine D3 receptor, dopamine D4 receptor, phosphodiesterase PDE10, serotonin 5-$HT_{1A}$ receptor, serotonin 5-$HT_{2A}$ receptor, serotonin 5-$HT_6$ receptor, adrenergic alpha 2 receptor, cannabinoid type 1 receptor, histamine H3 receptor, cyclooxygenases, sodium channels or glycine transporter GlyT1; or from agonists/positive modulators/partial agonists of the targets serotonin 5-$HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor. In one embodiment, said second anti-psychotic agent is selected from typical anti-psychotics, atypical anti-psychotics, D2 antagonists, partial D2 agonists, PDE10 antagonists, 5-$HT_{2A}$ antagonists, 5-$HT_6$ antagonists and KCNQ4 antagonists, and in particular atypical anti-psychotics, D2 antagonists, partial D2 agonists. Particular examples of such anti-psychotics include haloperidol, chlorpromazine, sulpirid, risperidone, ziprasidon, olanzapine, quetiapine, and clozapine.

In one embodiment, the invention relates to a pharmaceutical kit comprising a container comprising a compound of the present invention and a separate container comprising an anti-psychotic drug, such as typical anti-psychotics, atypical anti-psychotics, antagonists/inverse agonists/negative modulators/partial agonists of one or more of the targets dopamine D2 receptor, dopamine D3 receptor, dopamine D4 receptor, phosphodiesterase PDE10, serotonin 5-$HT_{1A}$ receptor, serotonin 5-$HT_{2A}$ receptor, serotonin 5-$HT_6$ receptor, adrenergic alpha 2 receptor, cannabinoid type 1 receptor, histamine H3 receptor, cyclooxygenases, sodium channels or glycine transporter GlyT1; or with agonists/positive modulators/partial agonists of one or more of the targets serotonin 5-$HT_{2C}$ receptor, KCNQ channels, NMDA receptor, AMPA receptor, nicotinic alpha-7 receptor, muscarinic M1 receptor, muscarinic M4 receptor, metabotropic glutamate receptor mGluR2, metabotropic glutamate receptor mGluR5, dopamine D1 receptor or dopamine D5 receptor.

Particular examples of such anti-psychotics include haloperidol, chlorpromazine, sulpirid, risperidone, ziprasidon, olanzapine, quetiapine, and clozapine.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

Unless otherwise indicated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Synthetic Routes

The compounds of the present invention of the general formula I, wherein $R^1$-$R^{12}$, A, and X are as defined above can be prepared by the methods outlined in the following reaction schemes and examples. In the described methods it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

In the intermediate compounds of the general formulae II—XXXI, $R^1$-$R^{12}$, A, X, and Y are as defined under formula I.

For compounds, which can exist as a mixture or equilibrium between two or more tautomers, only one tautomer is represented in the schemes, although it may not be the most stable tautomer. For compounds, which can exist in enantiomeric, stereoisomeric or geometric isomeric forms their geometric configuration is specified; otherwise the structure represents a mixture of stereoisomers. Such compounds include, but not limited to 1,3-ketoesters or enamines of the general formula IV and VII, which can exist in equilibrium between keto or enol forms and the latter may also exist in isomeric Z- and E-forms as well-known to chemists skilled in the art. Such compounds also include compounds of the present invention of the general formula I, which may exist as a mixture of atropisomers due to restricted rotation around carbon-carbon single bonds similar to atropisomerism in ortho, ortho'-disubstituted biaryl compounds also well-known to the person skilled in the art.

Starting materials of the general formulae III, VI, and XI are either obtained from commercial sources as summarized in the Table 2 or they can be readily prepared by standard methods or their modifications described in the literature.

2-Bromobenzoic acids of the general formula II are coupled with keto-esters of the general formula III in the presence of a strong base such as sodium hydride and copper or copper salts such as copper (I) bromide in a suitable solvent such as 1,4-dioxane, acetonitrile or an excess of the above keto-esters at suitable temperature such as reflux or at 70° C. with the formation of compounds of the general formula IV. Such arylation reaction is well-known in general as copper-catalyzed Ullmann-type coupling reaction (review: S. V. Ley, A. W. Thomas *Angew. Chem. Int. Ed.* 2003, 42, 5400). Also, in this particular case when the coupling reaction involves activated methylene compounds such as compounds of the general formula IV in the presence of copper or copper salts the reaction is known as the Hurtley reaction (W. R. H. Hurtley *J. Chem. Soc.* 1929, 1870).

The obtained compounds of the general formula IV are then reacted with anilines of the general formula VI with or without appropriate solvent under the heating conditions with the formation of isoquinolones of the general formula VIII via intermediate formation of enamines of the general formula VII which are usually not separated from the reaction mixture. Alternatively, the enamines of the general formula VII can be obtained from anilines of the general VI in the presence of the appropriate dehydrating agent such as tetraethoxysilane under heating conditions or at ambient temperature in the presence of a catalytic amount of acid such as acetic acid. Then, the cyclisation reaction with the formation of isoquinolones of the general formula VIII can be carried out under the heating conditions as mentioned above or at ambient temperature in the presence of an appropriate coupling reagent such as EDC/HOBT.

Furthermore, isoquinolinones of the general formula VIII can be obtained directly from the starting 2-bromobenzoic acids of the general formula II and deprotonated enamines of the general formula V in a modified one-pot procedure involving Hurtley reaction performed at 70° C. with the formation of the compounds of the general formula VII and subsequent cyclisation performed at higher temperature. Enamines of the general formula V are readily available from ketoesters III and anilines VI under conditions described above for preparation of enamines of the general formula VII.

Compounds of the general formula VIII are readily hydrolyzed to acids of the general formula IX under conditions for ester hydrolysis well known to chemists skilled in the art. Finally, the subsequent coupling with amines (A=C) or hydrazines (A=N) of the general formula XI leads to the formation of the compounds of the invention of the general formula I. Such coupling reactions usually performed via activation of the acid with an appropriate coupling or activation reagent such as but not limited to thionyl chloride with the formation of corresponding acid chloride or in the presence EDC/HOBT. Hydrazines of the general formula I where $R^1$=H can be converted to disubstituted hydrazides of the same general formula where $R^1$ is not hydrogen by acylation, alkylation or arylation reactions with appropriate acylation or alkylation reagents such as but not limited to acid chlorides, carbamoyl chlorides, chloroformates or alkylhalogenides.

Compounds of the general formula I where X is hydrogen can be converted to the compounds of the general formula XII by regio selective bromination reaction in the presence of bromination reagent such as bromine. Then the bromine atom can be substituted by various nucleophiles of the general formula X—H or X⁻ with the formation of the compounds of the invention of the general formula I. Those skilled in the art will readily appreciate that many nitrogen, carbon and sulphur nucleophiles such as but not limited to amines, aromatic amines, amides, heterocycles, alcohols, phenols, cyanides or thiols are commercially or readily available in the neutral or in the deprotonated anionic form required for such transformation.

If necessary, further derivatisation or transformation can be performed in the substituents $R^4$-$R^{12}$ and X using standard methods of organic synthesis known to the person of ordinary skill in the art.

Scheme 1

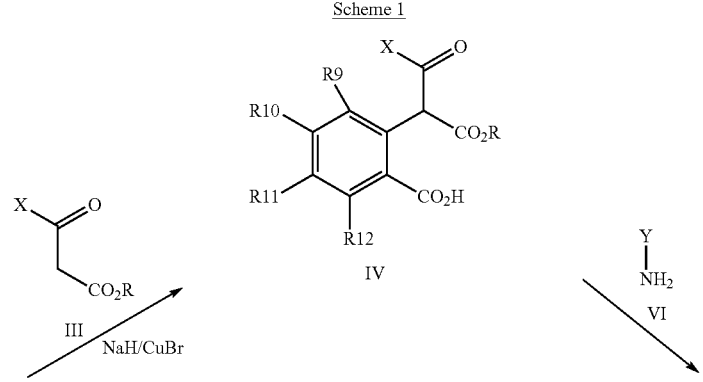

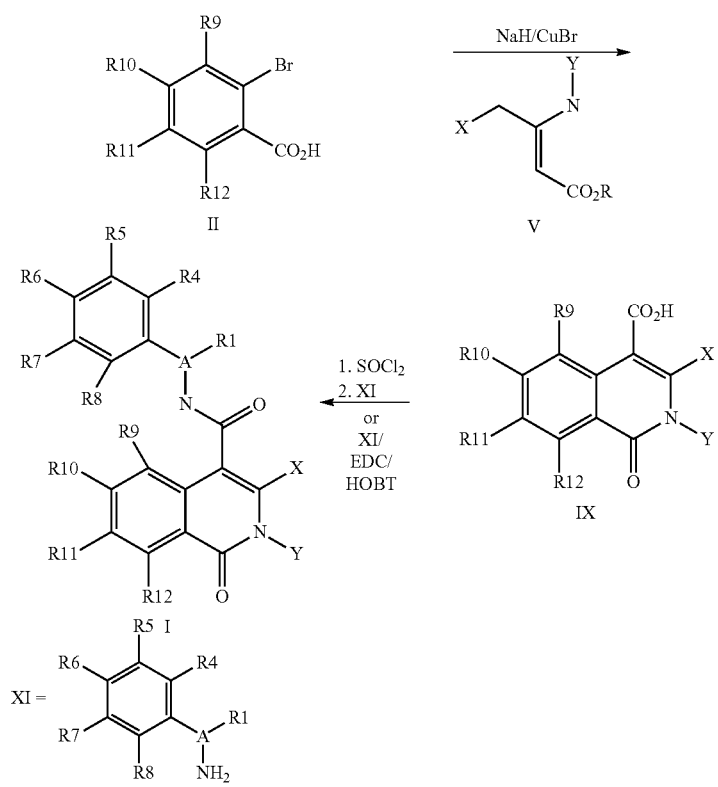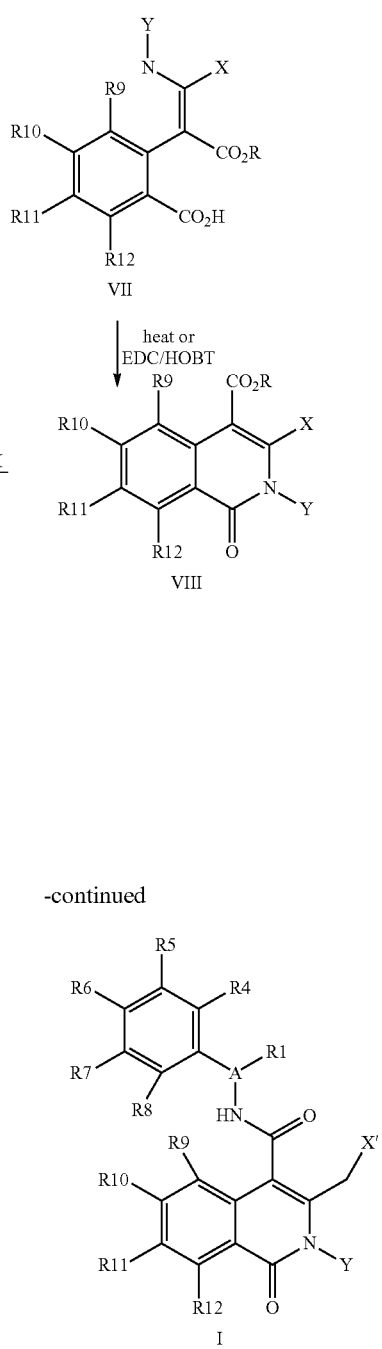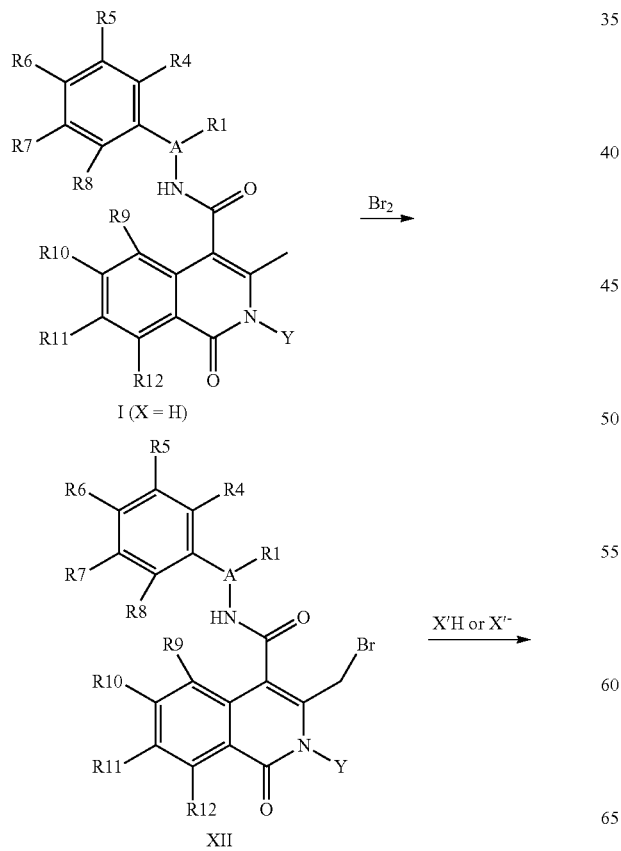
Scheme 2

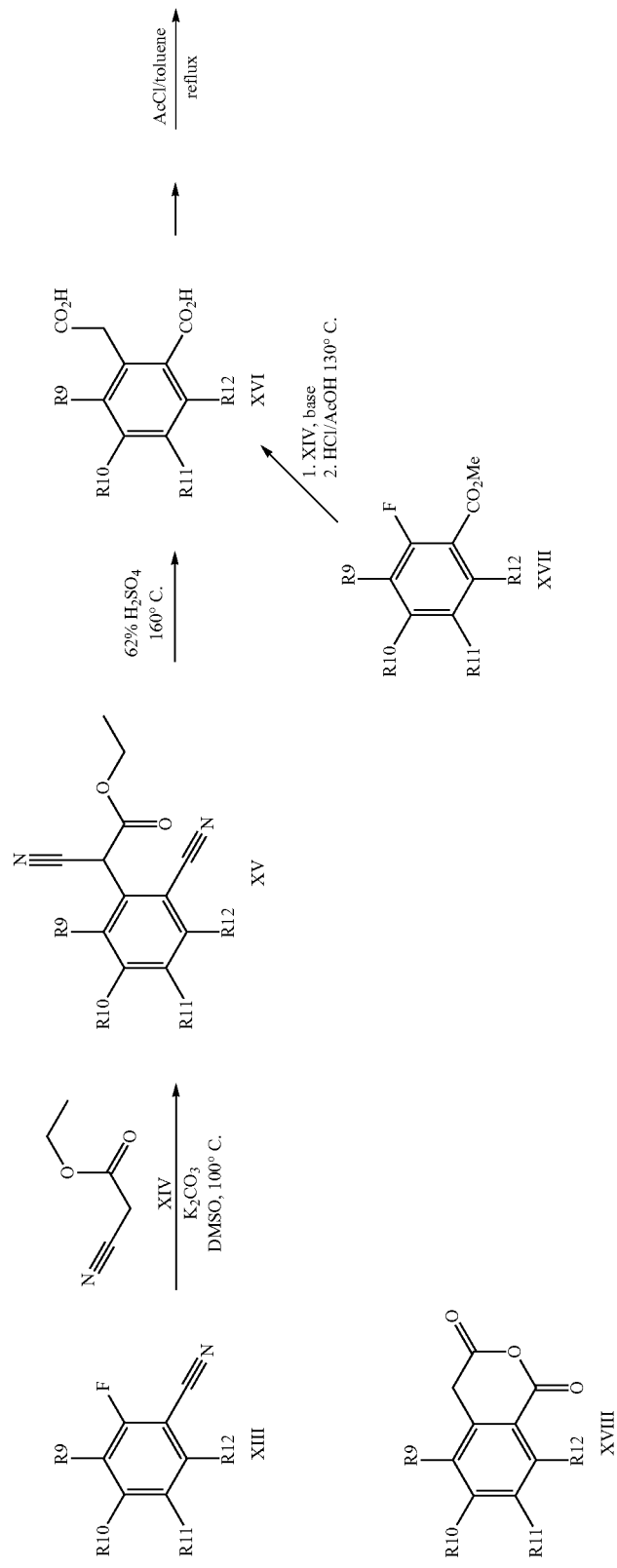
Scheme 3. Synthesis of homophthalic anhydrides

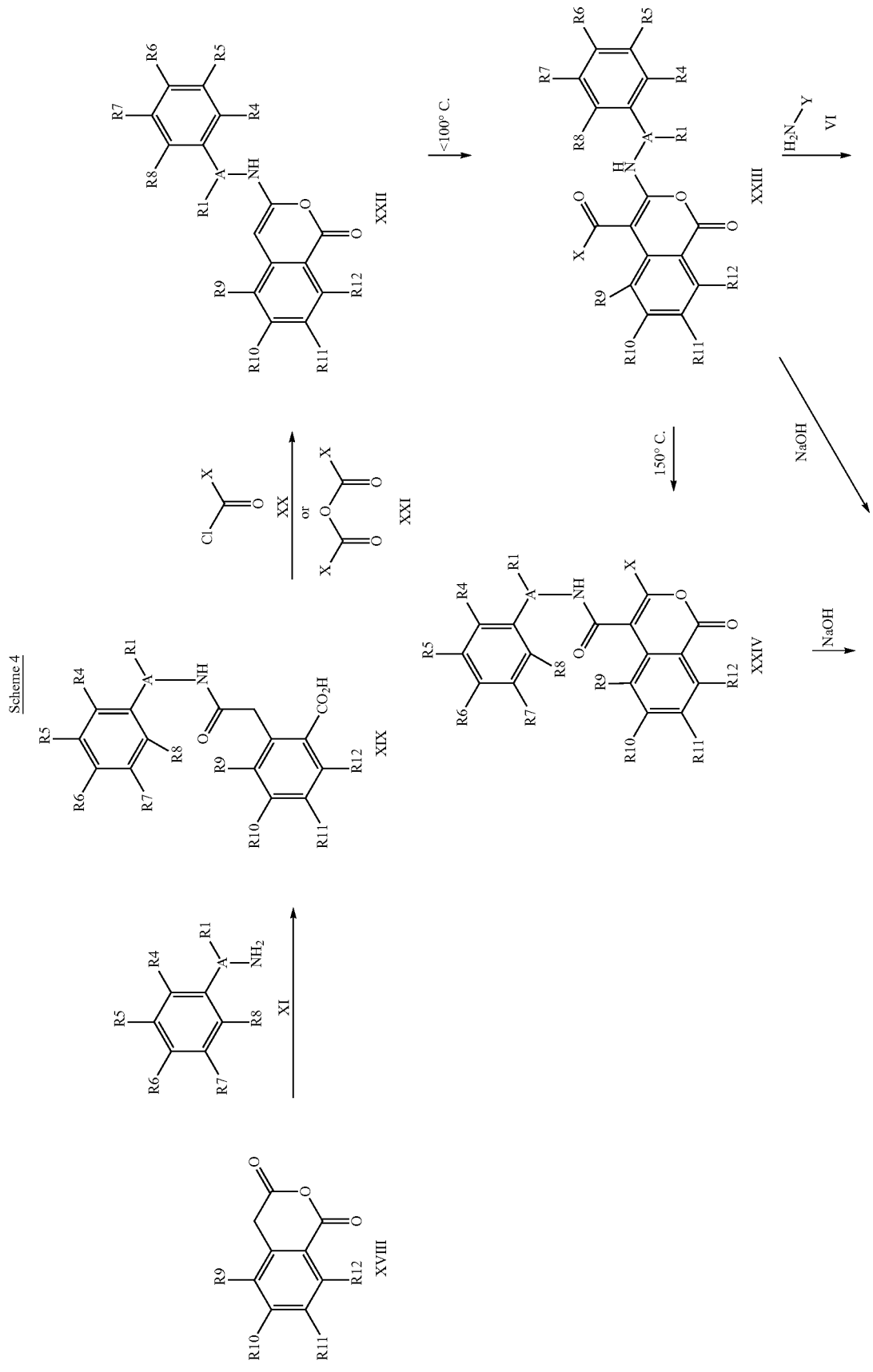

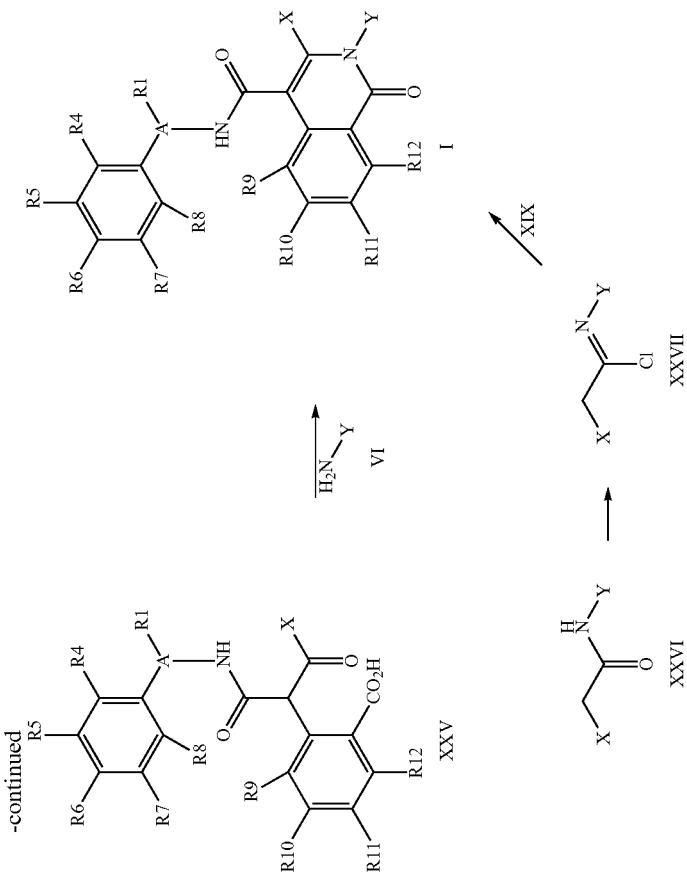

Scheme 5

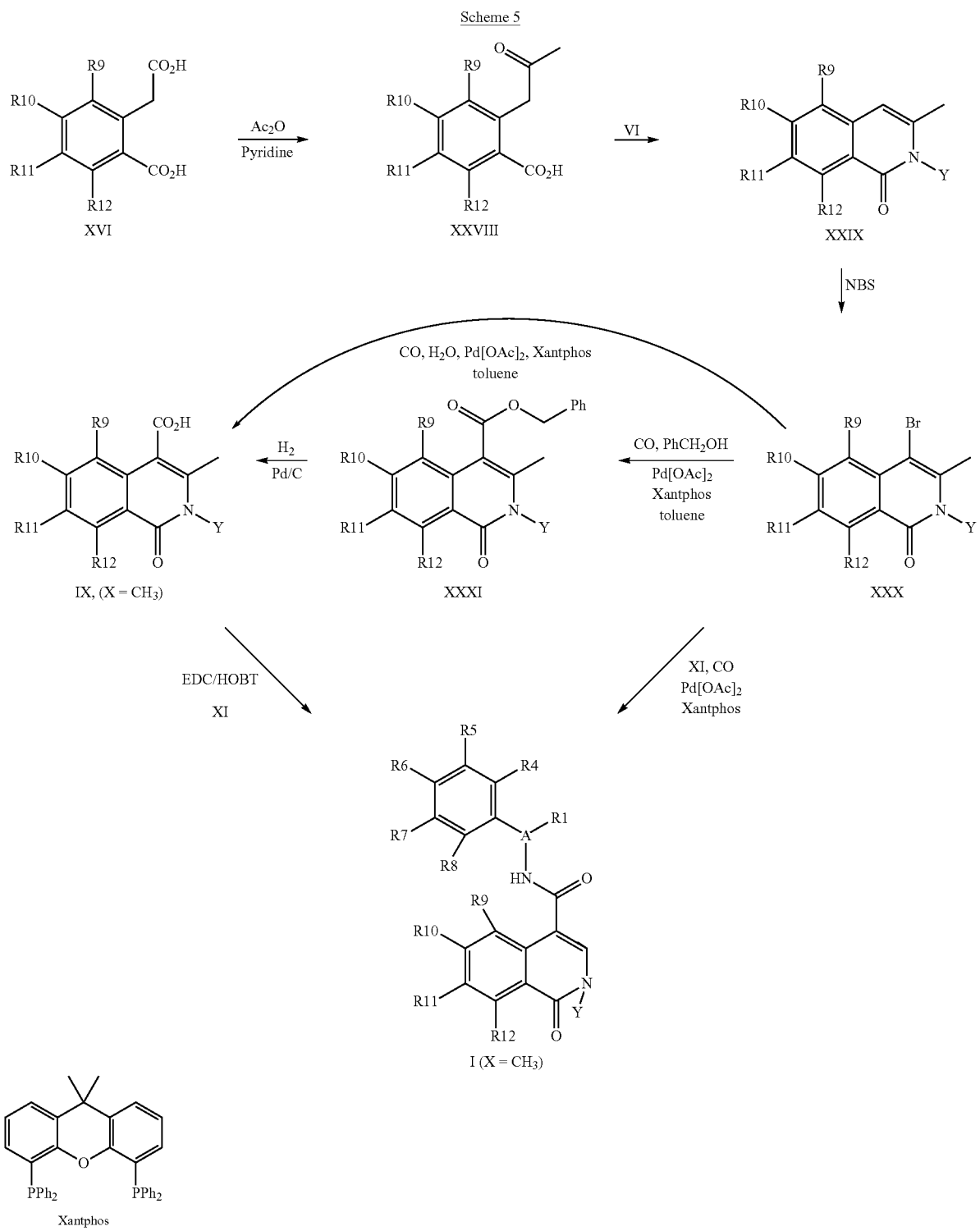

Alternatively, compounds of the general formula I can be prepared starting from substituted homophthalic anhydrides of the general formula XVIII as shown in Scheme 4. Homophthalic anhydrides are either commercially available or can be prepared as shown in scheme 3 starting from corresponding fluorobenzonitriles or fluorobenzoates of the general formula XIII and XVII, respectively. They undergo aromatic nucleophilic substitution reaction with ethyl cyanoacetate XIV in the presence of base such as potassium carbonate or cesium carbonate under heating conditions in appropriate solvent such as dimethylsulfoxide. The coupling products are hydrolyzed in the presence of strong acids such as sulfuric or hydrochloric acids in water under heating conditions with the formation of diacids of the general formula XVI. Finally, the diacids are converted into the homophthalic anhydrides of the general formula XVIII in the presence of dehydrating agent such as but not limited to acetyl chloride without a solvent or in the appropriate solvent such as toluene under heating conditions such as reflux.

Homophthalic anhydrides of the general formula XVIII can be regioselectively converted into the acid-amides of the general formula XIX at room temperature or under heating conditions in the appropriate solvent such as acetonitrile. Then they are treated with appropriate acid anhydrides or acid chlorides of the general formula XX and XXI, respectively, in the absence or presence of base such as triethyl amine and DMAP in the appropriated solvent, usually in acetonitrile, at room temperature or under mild heating conditions (T<+100° C.). This transformation first provides intermediate ketene-aminals of the general formula XXII, which undergo further acylation reaction with the formation of ketene-aminals of the general formula XXIII. Further heating at higher temperature such as at +150° C. leads to the rearrangement with the formation of amides of the general formula XIV. Compounds of the general formula XXIII and XXIV can be readily hydrolyzed at ambient temperature with an appropriate base such as sodium hydroxide in aqueous methanol or aqueous tetrahydrofurane as a solvent. The obtained keto-acids of the general formula XXV or ketene-aminals of the general formula XXIII are converted to the final compounds of the invention of the general formula I by condensation with anilines of the general formula VI under the same conditions as described above for condensation with keto-acids of the general formula IV.

Alternatively, acid-amides of the general formula XIX can be converted directly to the compounds of the invention of the general formula I by condensation with appropriate imidoyl chlorides of the general formula XXVII which are readily available from corresponding amide of the general formula XXVI, which are easily prepared by well-known coupling between aminoheterocycles of the general formula VI and corresponding carboxylic acids or their anhydrides or acid chlorides of the general formula XX and XXI, respectively.

In addition to the above methods, carbonylation reaction, in particular, the three-component coupling of an aryl halide, carbon monoxide, and a nucleophile, such as amine or alcohol (Schoenberg, A.; Bartoletti, I.; Heck, R. F. *J. Org. Chem.* 1974, 39, 3318; Schoenberg, A.; Heck, R. F. *J. Org. Chem.* 1974, 39, 3327) can be used in a key step as illustrated in scheme 5. Thus, diacids of the general formula XVI are converted into keto-acids of the general formula XXVIII in one-pot acylation—decarboxylation reaction in acetic anhydride (in the case of acetic anhydride substituent X is Me) and in the presence of pyridine followed by condensation with aminoheterocycles of the general formula VI with formation of isoquinolinones of the formula XXIX. They are regioselectively brominated with N-bromosuccinimide with formation of bromides of the general formula XXX. The aminocarbonylation reaction with bromides of the general formula XXX in the presence of amines of the general formula XI under an atmosphere of carbon monoxide promoted by a catalyst, for example palladium acetate—Xanthphos (Kranenburg, M.; van der Burgt, Y. E. M.; Kamer, P. C. J.; van Leeuwen, P. W. N. M. *Organometallics* 1995, 14, 3081) leads to the formation of compounds of the invention of the general formula I where X is Me. Alternatively, carbonylation reaction in the presence of alcohols such as benzyl alcohol under the same conditions leads to formation of benzyl esters of the general formula XXXI, which are readily converted into acids of the general formula IX by palladium catalyzed hydrogenation reaction followed by condensation with amines of the general formula XI as described above (scheme I). Also, acids of the general formula IX can be prepared directly by the carbonylation method in the presence of water instead of the benzyl alcohol under the same conditions (Scheme 5).

EXAMPLES

Analytical LC-MS, method A (used in most cases unless noted otherwise): data were obtained on a Sciex API 150EX analytical LC/MS system equipped with Applied Biosystems API150EX single qaudrupole mass spectrometer and atmospheric pressure photo ionisation (APPI) ion source, Shimadzu LC10ADvp LC pumps (3×), Shimadzu SPD-M20A photodiode array detector, SEDERE Sedex 85—low temperature Evaporative Light Scattering Detector (ELSD), Shimadzu CBM-20A system controller, Gilson 215 autosampler and Gilson 864 degasser controlled by Analyst Software. Column: 30×4.6 mm Waters Symmetry C18 column with 3.5 µm particle size; Injection Volume: 15 µL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 2.4 minutes then with 10% B in 0.4 minutes and with a flow rate of 3.3 mL/minute. The retention times ($t_R$) are expressed in minutes based on UV-trace at 254 nm.

Analytical LC-MS, method B: data were obtained on a Sciex API300 analytical LC/MS system equipped with Applied Biosystems API300 triple qaudrupole mass spectrometer with atmospheric pressure photo ionisation (APPI) ion source, Shimadzu LC10ADvp LC pumps (3X), Shimadzu SPD-M20A photodiode array detector, Polymer Labs PL-ELS 2100—low temperature Evaporative Light Scattering Detector (ELSD), Shimadzu SCL10A VP system controller, Gilson 215 autosampler and Gilson 864 degasser controlled by Analyst Software. Column: Symmetry C18 3.5 µm, 4.6× 30 mm 30×4.6 mm; Injection Volume: 5 µL; Column temperature: 60° C.; Solventsystem: A=water/trifluoroacetic acid (100:0.05) and B=water/acetonitrile/trifluoroacetic acid (5:95:0.035); Method: Linear gradient elution with 10% B to 100% B in 1.45 minutes then with 10% B in 0.55 minutes and with a flow rate of 5.5 mL/minute:

| Time, min. | % B |
| --- | --- |
| 0.00 | 10.0 |
| 1.45 | 100.0 |
| 1.55 | 10.0 |
| 2.0 | 10.0 |

The retention times ($t_R$) are expressed in minutes based on UV-trace at 254 nm.

Preparative LC-MS purification was performed on the same Sciex API 150EX system equipped with Gilson 333 and 334 pumps, Shimadzu LC10ADvp pump, Gilson UV/VIS 155 UV detector, Gilson 233XL autosampler, Gilson FC204 fraction, Gilson 506C system interface, Gilson 864 degasser, DIY flowsplitter (approx. 1:1000), and LC Packings Accurate flowsplitter (1:10.000@ 140 ml/min). The MS and fraction collector was controlled by Masschrom software (Macintosh PC), the LC system was controlled by Unipoint software. For a small scale (<20 mg) purification fractions were collected in 4 ml vials using Symmetry C18 5 µm, 10×50 mm column, injection volume of 0-300 µL, flow rate of 5.7 ml/min and duration of 8 min. Gradient:

| Time, min. | % B |
|---|---|
| 0.00 | 10.0-50.0 (variable, depending on the sample) |
| 7.00 | 100.0 |
| 7.10 | 10.0-50.0 |
| 8.00 | 10.0-50.0 |

$^1$H NMR spectra were recorded at 500.13 MHz on a Bruker Avance DRX-500 instrument at T=303.3 K. Variable temperature $^1$H NMR spectra were recorded on the same instrument or at 250 MHz on a Bruker Avance DPX-250 instrument. Deuterated dimethyl sulfoxide (DMSO-$d_6$, 99.8% D) was used as solvent unless noted otherwise. Tetramethylsilane was used as internal reference standard. Chemical shift values are expressed in ppm-values relative to tetramethylsilane unless noted otherwise. The following abbreviations or their combinations are used for multiplicity of NMR signals: s=singlet, d=doublet, t=triplet, q=quartet, qui=quintet, h=heptet, dd=double doublet, ddd=double double doublet, dt=double triplet, dq=double quartet, tt=triplet of triplets, m=multiplet and br=broad or broad singlet.

Microwave experiments were performed in sealed process vials or reactors using an Emrys Synthesizer or Emrys Optimizer EXP from Personal Chemistry or a Milestone Microsynth instrument from Milestone. Before sealing the process vial it was flashed with argon. When a reaction was heated in a microwave instrument, it was cooled to 25° C. before the next process step.

PREPARATION OF INTERMEDIATES

Synthesis of Homophthalic Anhydrides of the General Formula XVIII:

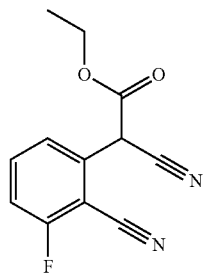

Cyano-(2-cyano-3 fluoro-phenyl)-acetic acid ethyl ester

A mixture of cyanoacetic acid ethyl ester (26.7 mL, 251 mmol), 2,6-difluorobenzonitrile (33.2 g, 239 mmol) and potassium carbonate (82.5 g, 597 mmol) in dimethyl sulfoxide (120 mL) was stirred at +55° C. for 16 hours and poured into ice-water mixture (ca. 400 mL). It was acidified with conc. aq. HCl with caution ($CO_2$ evolution) and extracted with ethyl acetate (600 mL). The organic phase was washed with brine (100 mL) and evaporated to give 55.1 g of a pale yellow solid that was used in the next step without further purification. $^1$H NMR (500 MHz, CDCl$_3$): 1.35 (t, J=7.0 Hz, 3H), 4.34 (m, 2H), 5.13 (s, 1H), 7.33 (t, J=8.4 Hz, 1H), 7.57 (d, J=7.9 Hz, 1H), 7.33 (dd, J=7.9 Hz, J=13.9 Hz, 1H).

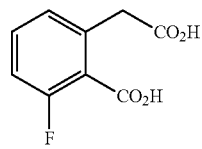 [SMILES: O=C(O)Cc1cccc(F)c1C(=O)O]

2-Carboxymethyl-6-fluoro-benzoic acid

A mixture of 62% sulfuric acid (2:1 conc. $H_2SO_4$ in water, 400 ml) and cyano-(2-cyano-3-fluoro-phenyl)-acetic acid ethyl ester (52.0 g, 224 mmol) was stirred at +150° C. overnight (16 hours). The reaction mixture was poured into ice (ca. 500 g) and neutralised with 10.8 N aq. NaOH (500 mL) with cooling. The mixture was extracted with ethyl acetate (3×500 mL) and the combined organic solution was washed with brine, dried over MgSO$_4$ and evaporated to give 40.28 g of crude product that was used in the next step without further purification. The analytical sample was prepared by recrystallisation from toluene-ethyl acetate. $^1$H NMR (500 MHz, DMSO-$d_6$): 3.4 (br, CO$_2$H+H$_2$O), 3.77 (s, 2H), 7.17 (d, J=7.9 Hz, 1H), 7.2 (overlapping t (unres. dd), 1H), 7.45 (dd, J=7.9 Hz, J=13.9 Hz, 1H), 12.95 (br, CO$_2$H).

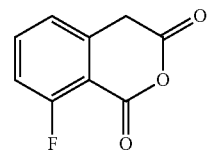 [SMILES: O=C1Cc2cccc(F)c2C(=O)O1]

8-Fluoro-isochroman-1,3-dione

2-Carboxymethyl-6-fluoro-benzoic acid (130 mg, 0.65 mmol) in acetyl chloride (2 ml) was heated under microwave irradiation at 150° C. for 10 min then concentrated in vacuo to give the title product (120 mg, 100% yield). The compound is hydroscopic and slowly decomposes back to the starting diacid in wet solvents or under moisturised atmosphere. $^1$H NMR (500 MHz, DMSO-$d_6$): 4.29 (s, 2H), 7.27 (d, J=7.8 Hz, 1H), 7.34 (dd, J=8.5 Hz, J=11 Hz, 1H), 7.76 (dt, J=5.3 Hz, J=8 Hz, 1H).

The following homophthalic anhydrides were synthesized analogously:

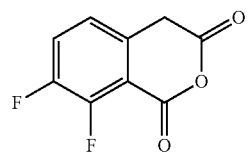 [SMILES: O=C1Cc2ccc(F)c(F)c2C(=O)O1]

7,8-Difluoro-isochroman-1,3-dione

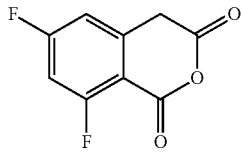

6,8-Difluoro-isochroman-1,3-dione

Synthesis of chiral and racemic amines of the general formula XI:

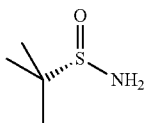

(S)-(−)-2-Methyl-2-propanesulfinamide

The title chiral auxiliary was prepared according to a described procedure for the (R)-(+)-enantiomer by D. J. Weix and J. A. Ellman *Organic Syntheses* 2005, 82, 157.

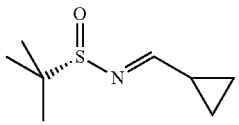

(S)-2-Methyl-2-propanesulfinic acid 1-cyclopropyl-methylideneamide

The title compound was prepared according to a general procedure described by G. Liu, D. A. Cogan, T. D. Owens, T. P. Tang, and J. A. Ellman J. Org. Chem. 1999, 64, 1278: A mixture of cyclopropanecarboxaldehyde (35.0 g, 0.5 mol), 2-methyl-2-propanesulfinic acid 1-cyclopropyl-methylideneamide (30 g, 0.25 mol) and anhydrous $CuSO_4$ (120 g, 0.75 mol) in $CH_2Cl_2$ (1500 mL) was stirred at room temperature overnight. The reaction mixture was filtered and evaporated to give the title compound (39 g, yield 95%), which was used in the next step without further purification.

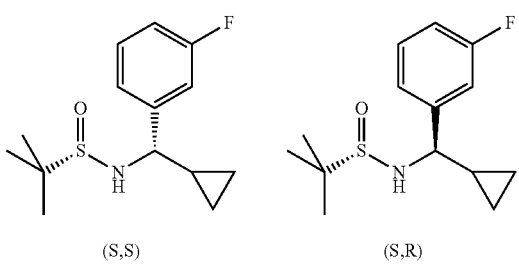

(S)-2-Methyl-2-propanesulfinic acid [(S)-cyclopropyl-(3-fluoro-phenyl)-methyl]-amide and (S)-2-Methyl-2-propanesulfinic acid [(R)-cyclopropyl-(3-fluoro-phenyl)-methyl]-amide The title compounds were obtained according to a general described procedure for 1,2-stereoselective addition of organometallic reagents to sulfinyl imines by D. A. Cogan, G. Liu, J. A. Ellman, *Tetrahedron* 1999, 55, 8883.

Procedure A: To an anhydrous lithium chloride (1.7 g, 40 mmol) THF (20 ml) was added under nitrogen followed by slow addition of i-PrMgCl (22 mL, 2 M in THF) and the obtained mixture was stirred at r.t. overnight. The obtained i-PrMgCl.LiCl solution was added dropwise to a stirred solution of 1-bromo-3-fluorobenzene (5.6 g, 33 mmol) in THF (25 ml) at 0° C. and stirring continued for 2 hours. The obtained Grignard reagent was added to a solution of (S)-2-methyl-2-propanesulfinic acid 1-cyclopropyl-methylideneamide (2.5 g, 14 mmol) in $CH_2Cl_2$ (60 mL) at −48° C. The mixture was stirred at −48° C. for 5 hours and then at room temperature overnight. The reaction mixture was quenched by addition of aq. sat. $NH_4Cl$ (50 mL) and extracted with $CH_2Cl_2$ (3×100 mL). The combined organic solution was dried ($Na_2SO_4$) and evaporated to give a crude mixture, which was purified by column chromatography on silica gel (EtOAc/petroleum ether=1/10). The obtained mixture of diastereoisomers was resolved by SFC to give the title (S,S)-isomer as the major product (1.5 g, yield 37.5%) and the title (S,R)-isomer (0.16 g, yield: 4.0%).

Procedure B: Alternatively, to a suspension of Mg (13.4 g, 0.55 mol) in 50 mL of anhydrous THF at 50° C. a solution of 1-bromo-3-fluorobenzene (89.0 g, 0.50 mol) was added dropwise. The mixture was stirred for 2 hours at +50° C. and then it was added dropwise to a solution of (S)-2-methyl-2-propanesulfinic acid 1-cyclopropyl-methylideneamide (78.0 g, 0.46 mol) in 100 mL of THF at 50-60° C. and stirred for 2 hours. It was quenched with aq. sat. $NH_4Cl$ (100 ml), water (300 mL), filtered, and the both solid and filtrate were extracted with hot ethyl acetate (600 mL) and evaporated in vacuo. The residue was crystallized from a mixture of ethyl acetate and petroleum ether (1:1, 200 mL) at −20° C. to give 80 g of the title (S,S)-isomer as a white powder, 66% yield, de 100% according to chiral HPLC. $^1H$ NMR ($CDCl_3$, 400 MHz, TMS=0 ppm): 7.34-7.28 (m, 1H), 7.16-7.12 (m, 2H), 7.00-6.96 (m, 1H), 3.68 (dd, J=8.8 Hz, 3.2 Hz, 1H), 3.52 (s, 1H), 1.42 (s, 9H), 1.15-1.08 (m, 1H), 0.84-0.75 (m, 1H), 0.69-0.61 (m, 1H), 0.55-0.46 (m, 1H), 0.28-0.21 (m, 1H).

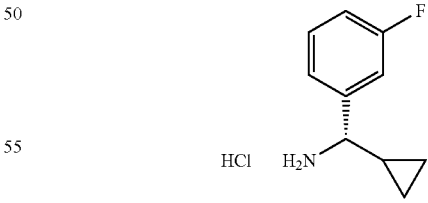

(S)-(+)-C[C-Cyclopropyl-C-(3-fluoro-phenyl)]-methylamine hydrochlorid

To a saturated solution of HCl in anhydrous dioxane (400 ml) (S)-2-methyl-2-propanesulfinic acid [(S)-cyclopropyl-(3-fluoro-phenyl)-methyl]-amide (80 g, 0.3 mol) was added at 0° C. After stirring at r.t. for 1 hour, the reaction mixture was evaporated in vacuo. The residue was washed with anhydrous ether (2×100 ml) and dried in vacuo to give 56 g of the title compound as a white solid, yield 93%, ee 100% according to chiral HPLC. $[\alpha]^{20}{}_D$=+52.69 (c=10 mg/mL, $CH_3OH$). $^1H$ NMR ($CD_3OD$, 400 MHz, TMS=0): 7.44-7.39 (m, 1H), 7.25-7.19 (m, 2H), 7.12-7.07 (m, 1H), 3.56 (d, J=10.0 Hz, 1H), 1.37-1.28 (m, 1H), 0.78-0.75 (m, 1H), 0.61-0.55 (m, 2H), 0.39-0.36 (m, 1H).

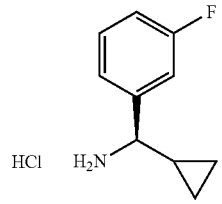

(R)-(−)-C[C-Cyclopropyl-C-(3-fluoro-phenyl)]-methylamine hydrochloride

The title compound was prepared according to the above identical procedure from (S)-2-methyl-2-propanesulfinic acid [(R)-cyclopropyl-(3-fluoro-phenyl)-methyl]-amide (0.16 g, 0.6 mmol) to give 0.116 g of the title compound as a white solid. $[\alpha]^{20}{}_D$=49.18 (c=10 mg/mL, $CH_3OH$), ee 100%. $^1H$ NMR ($CD_3OD$, 400 MHz, TMS=0): identical with (S)-enantiomer.

The following enantiomerically pure amine hydrochlorides were obtained analogously in three-step procedure starting from condensation of the corresponding aldehyde with chiral auxiliary, stereoselective Grignard addition where the mixture of diastereoisomers was resolved either by recrystallisation or by chromatography (SFC or column) and the major (S,S)-diastereoisomer was finally converted to a chiral amine with HCl.

| Structure (HCl salt) | Chemical name | $[\alpha]^{20}{}_D$, (10 mg/ml) MeOH | ee (chiral HPLC) | $^1H$ NMR ($CD_3OD$, 400 MHz) |
|---|---|---|---|---|
| | C-((S)-C-Cyclobutyl-C-phenyl)-methylamine | +17.57 | 95.4 | 7.37-7.31 (m, 5H), 4.12 (d, J = 10.4 Hz, 1H), 2.84-2.75 (m, 1H), 2.21-2.13 (m, 1H), 1.99-1.64 (m, 5H). |
| | C-[(S)-C-Cyclobutyl-C-(3-fluoro-phenyl)]-methylamine | +19.45 | 100 | 7.48-7.44 (m, 1H), 7.24-7.15 (m, 3H), 4.26 (d, J = 10.4 Hz, 1H), 2.87-2.84 (m, 1H), 2.25-2.24 (m, 1H), 2.05-1.76 (m, 5H). |
| | C-[(S)-C-Cyclobutyl-C-(4-fluoro-phenyl)]-methylamine | +26.98 | 100 | 7.45-7.41 (m, 2H), 7.18-7.14 (m, 2H), 4.22 (d, J = 10.6 Hz, 1H), 2.89-2.81 (m, 1H), 2.28-2.21 (m, 1H), 2.05-1.71 (m, 5H). |
| | C-[(S)-C-Cyclopropyl-C-(3,4-difluoro-phenyl)]-methylamine | +44.26 | 96 | 7.50-7.32 (m, 3H), 3.62 (d, J = 10.4 Hz, 1H), 1.38 (m, 1H), 0.86 (m, 1H), 0.68 (m, 1H), 0.62 (m, 1H), 0.45 (m, 1H) |
| | C-[(S)-C-Cyclobutyl-C-(3,4-difluoro-phenyl)]-methylamine | +27.22 | >99 | 7.41-7.32 (m, 2H), 7.25 (m, 1H), 4.26 (d, J = 10.4 Hz, 1H), 2.48 (m, 1H), 2.24 (m, 1H), 2.05-1.72 (m, 5H) |
| | C-[(S)-C-Cyclopropyl-C-(3,5-difluoro-phenyl)]-methylamine | +47.5 | 97.3 | 7.16 (m, 2H), 7.05 (m, 1H), 3.65 (d, J = 10.8 Hz, 1H), 1.36 (m, 1H), 0.86 (m, 1H), 0.72 (m, 1H), 0.65 (m, 1H), 0.48 (m, 1H) |

-continued

| Structure (HCl salt) | Chemical name | $[\alpha]^{20}{}_D$, (10 mg/ml) MeOH | ee (chiral HPLC) | $^1$H NMR (CD$_3$OD, 400 MHz) |
|---|---|---|---|---|
| 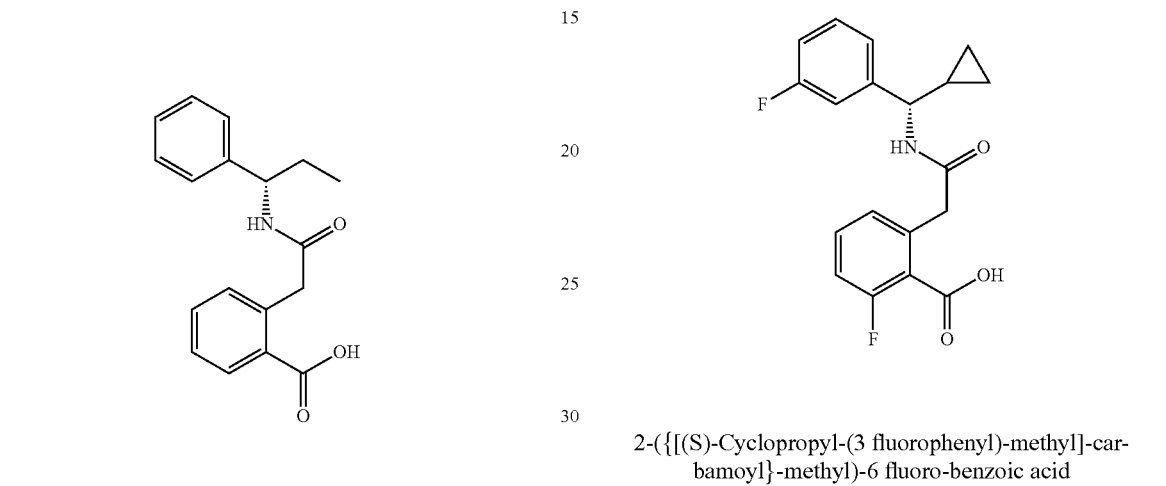 | C-[(S)-C-Cyclopropyl-C-(4-fluoro-phenyl)]-methylamine | +47.25 | 98.9 | 7.50-7.46 (m, 2H), 7.19-7.14 (m, 2H), 3.56 (d, J = 10.0 Hz, 1H), 1.40-1.31 (m, 1H), 0.83-0.76 (m, 1H), 0.67-0.54 (m, 2H), 0.40-0.31 (m, 1H) |

Synthesis of Acid-Amides of the General Formula XIX:

2-[((S)-1-Phenyl-propylcarbamoyl)-methyl]-benzoic acid

A mixture of homophthalic anhydride (810 mg, 5 mmol) and (S)-(−)-1-phenylpropylamine (676 mg, 5 mmol) in acetonitrile (15 ml) was heated under microwave irradiation at +150° C. for 15 min. White precipitate was collected by filtration, washed with heptane and dried in vacuo to give pure title compound in 72% yield (1.065 g). Alternatively, to a stirred solution of homophthalic anhydride (16.214 g, 0.1 mol) in acetonitrile (100 ml) (S)-(−)-1-phenylpropylamine (13.83 g, 0.102 mol) was added dropwise (exothermic reaction) and the obtained reaction mixture was refluxed for 5 min. It was allowed to cool and the product was isolated by filtration as above to give 23.4 g of colourless solid, 79% yield. LC-MS (m/z) 298.5 (MH$^+$); $t_R$=1.11. $^1$H NMR (500 MHz, DMSO-d$_6$): 0.84 (t, J=7.3 Hz, 3H), 1.67 (quintet, J=7.3 Hz, 2H), 3.85 (d of AB system, J=15.1 Hz, 1H), 3.95 (d of AB system, J=15.1 Hz, 1H), 4.66 (q, J=7.6 Hz, 1H), 7.2 (unres. m, 1H), 7.25-7.34 (m, 5H), 7.45 (t, J=7.3 Hz, 1H), 7.8 (d, J=7.8 Hz, 1H), 8.39 (br. d, J=7.7 Hz, 1H, NH).

The following compounds were obtained analogously from corresponding homophthalic anhydrides and amines of the general formula XVIII and XI, respectively. The reactions were usually run at room temperature and the products were isolated by extraction or filtration and used in the next steps without further purification.

2-({[(S)-Cyclopropyl-(3 fluorophenyl)-methyl]-carbamoyl}-methyl)-6 fluoro-benzoic acid LC-MS (m/z) 346.2 (MH$^+$); $t_R$=1.14. $^1$H NMR (500 MHz, DMSO-d$_6$): 0.35 (m, 1H), 0.39 (m, 1H), 0.5 (m, 2H), 1.12 (m, 1H), 3.68 & 3.74 (two d of AB system, J=15.2 Hz, 2H, CH$_2$), 4.25 (t, J=8.5 Hz, 1H), 7.05 (dt, J=2.2, 8.05 Hz, 1H), 7.13 (d, J=8.1 Hz, 1H), 7.16-7.21 (m, 2H), 7.35 (m, 1H), 7.42 (m, 1H), 8.66 (d, J=8.2 Hz, 1H, NH), 13.44 (br., CO$_2$H).

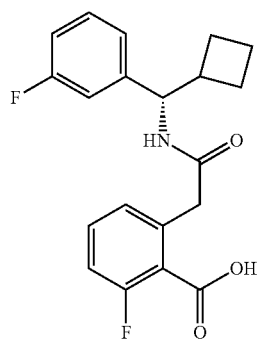 [SMILES: O=C(Cc1cccc(F)c1C(=O)O)N[C@H](c1cccc(F)c1)C1CCC1]

2-({[(S)-Cyclobutyl-(3 fluoro phenyl)-methyl]-carbamoyl}-methyl)-6 fluoro-benzoic acid LC-MS (m/z) 360.2 (MH$^+$); $t_R$=1.31.

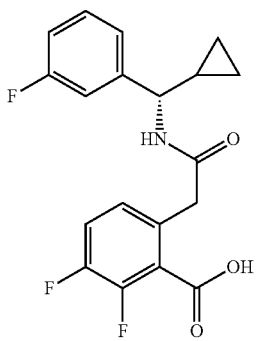 [SMILES: O=C(Cc1ccc(F)c(F)c1C(=O)O)N[C@H](c1cccc(F)c1)C1CC1]

6-({[(S)-Cyclopropyl-(3-fluoro-phenyl)-methyl]-carbamoyl}-methyl)-2,3-difluoro-benzoic acid

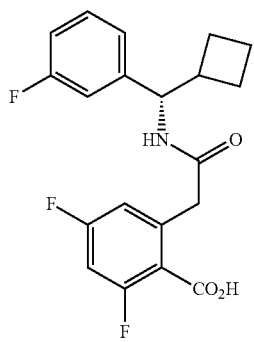 [SMILES: O=C(Cc1cc(F)cc(F)c1C(=O)O)N[C@H](c1cccc(F)c1)C1CCC1]

2-({[(S)-Cyclobutyl-(3-fluoro-phenyl)-methyl]-carbamoyl}-methyl)-4,6-difluoro-benzoic acid LC-MS (m/z) 378.4 (MH$^+$); t$_R$=1.28.
Synthesis of Compounds of the General Formula XXIII:

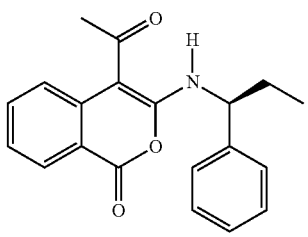

4-Acetyl-3-((S)-1-phenyl-propylamino)-isochromen-1-one

A mixture of 2-[((S)-1-phenyl-propylcarbamoyl)-methyl]-benzoic acid (10 g), acetic anhydride (50 ml), and N,N-dimethylaminopyridine (100 mg) was heated at gentle reflux (T$_{max}$=+124° C.) for 7 min and evaporated in vacuo at +50° C. to give the title compound as a yellow-brown solid (11.1 g, purity 98% by NMR). LC-MS (m/z) 322.3 (MH$^+$); t$_R$=1.72. $^1$H NMR (500 MHz, DMSO-d$_6$): 0.89 (t, J=7.2 Hz, 3H), 1.86-1.97 (m, 2H), 2.56 (s, 3H), 4.95 (q, J=7.1 Hz, 1H, CH—NH), 7.26 (t, J=7.5 Hz, 1H), 7.29 (unres. m, 1H), 7.36-7.41 (unres m., 3H), 7.71 (t, J=7.5 Hz, 1H), 7.75 (d, J=8.3 Hz, 1H), 7.98 (d, J=7.8 Hz, 1H), 11.53 (d, J=7.6 Hz, 1H, NH). $^{13}$C APT NMR (125 MHz, DMSO-d$_6$, δ(DMSO-d$_6$)=39.87 ppm): 10.68 (CH$_3$), 30.0 (CH$_2$), 31.57 (CH$_3$), 57.01 (CH), 92.44 (C), 114.88 (C), 124.2 (CH), (CH), 124.26 (CH), 126.65 (CH), 127.8 (CH), 129.05 (CH), 129.93 (CH), 135.71 (CH), 138.68 (C), 141.86 (C), 158.51 (C), 160.55 (C), 194.82 (C, MeCO).

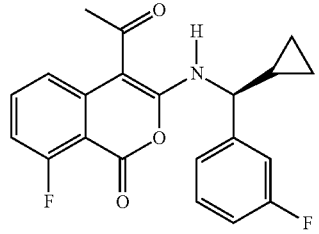 [SMILES: CC(=O)c1c(N[C@H](c2cccc(F)c2)C2CC2)oc(=O)c2c(F)cccc12]

4-Acetyl-3-{[(S)-cyclopropyl-(3-fluoro-phenyl)-methyl]-amino}-8-fluoro-isochromen-1-one A mixture of 2-({[(S)-cyclopropyl-(3-fluoro-phenyl)-methyl]-carbamoyl}-methyl)-6-fluoro-benzoic acid (12.92 g, 37.41 mmol) and acetic anhydride (100 mL, 1 mol) was stirred at +65° C. for 20 hours and evaporated in vacuo (65° C., 10 mbar, 2 hours) to give the title compound as a thick brown oil, which was used in the next step without purification (14.30 g, yield 103.5%, purity 95% according to $^1$H NMR). LC-MS (m/z) 370.1 (MH$^+$); t$_R$=1.65. $^1$H NMR (500 MHz, DMSO-d$_6$): 0.45-0.59 (m, 3H), 0.64 (m, 1H), 1.41 (m, 1H), 2.53 (s, 3H), 4.36 (t (unres. dd), 1H), 7.03 (dd, J=8.3, 10.7 Hz, 1H), 7.12 (dt, J=1.9, 8.5 Hz, 1H), 7.27 (d, J=10.2 Hz, 1H), 7.3 (d, J=7.8 Hz, 1H), 7.42 (q, J=7.8 Hz, 1H), 7.53 (d, 8.5 Hz, 1H), 7.7 (m, 1H), 11.3 (d, J=7.3 Hz, 1H, NH).

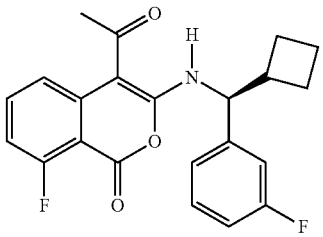 [SMILES: CC(=O)c1c(N[C@H](c2cccc(F)c2)C2CCC2)oc(=O)c2c(F)cccc12]

4-Acetyl-3-{[(S)-cyclobutyl-(3-fluoro-phenyl)-methyl]-amino}-8-fluoro-isochromen-1-one LC-MS (m/z) 384.4 (MH$^+$); t$_R$=1.82.
Hydrolysis of Compounds of the General Formula XXIII into Compounds of the General Formula XXV:

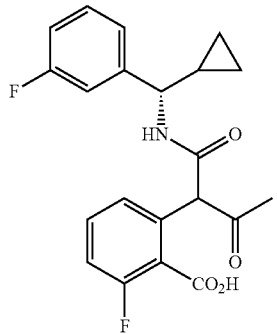

2-(1-{[(S)-Cyclopropyl-(3-fluoro-phenyl)-methyl]-carbamoyl}-2-oxo-propyl)-6-fluoro-benzoic acid 4-Acetyl-3-{[(S)-cyclopropyl-(3-fluoro-phenyl)-methyl]-amino}-8-fluoro-2-benzopyran-1-one (14.30 g, 38.72 mmol) was dissolved in a mixture of tetrahydrofuran (50 mL) and methanol (50 mL) and placed on an ice/water bath with stirring. NaOH (1 M in H$_2$O, 100 ml) was added and stirring continued for 1 hour. The cold bath removed and the mixture was allowed to warm to r.t. (20° C.) during 1 hour. The reaction mixture was poured into ice-water mixture (200 g+200 ml), followed by slow addition of 2 M aq. HCl (200 mL) and extracted with ethyl acetate (200 mL), washed with sat. aq. NaCl, dried (Na$_2$SO$_4$), filtered and evaporated to give the title compound (14.65 g, yield 97.7%) as a pale brown foam. The crude product was used in the next step without further purification. LC-MS (m/z) 388.3 (MH$^+$); t$_R$=1.2. $^1$H NMR (500 MHz, DMSO-d$_6$): a mixture of tautomers and diastereoisomers.

The following compound was prepared analogously:

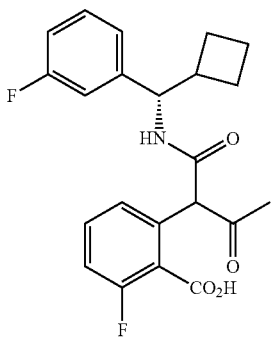 [SMILES: CC(=O)C(C(=O)N[C@H](c1cccc(F)c1)C1CCC1)c1cccc(F)c1C(=O)O]

2-(1-{[(S)-Cyclobutyl-(3-fluoro-phenyl)-methyl]-carbamoyl}-2-oxo-propyl)-6-fluoro-benzoic acid LC-MS (m/z) 402.2 (MH$^+$); t$_R$=1.36.

Synthesis of compounds of the general formula XXIV and XXV: Compounds of general formula XXIV obtained analogously as described above for compounds of general formula XXIII but at higher temperature (150° C., 15 min) and they are usually hydrolyzed to compounds of the general formula XXV without isolation and characterization, so only two examples of compounds XXIV are given below.

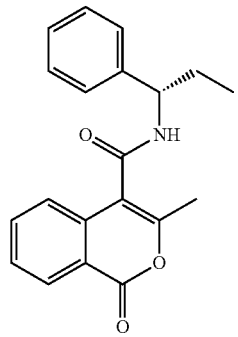

3-Methyl-1-oxo-1H-isochromene-4-carboxylic acid ((S)-1-phenyl-propyl)-amide

The title compound was purified by flash chromatography on SiO$_2$. LC-MS (m/z) 322.1 (MH$^+$); t$_R$=1.27. $^1$H NMR (500 MHz, CDCl$_3$): 1.03 (t, J=7.3 Hz, 3H), 1.91-2.06 (complex m, 2H, CH$_2$), 2.19 (s, 3H), 5.11 (q, J=7.8 Hz, 1H), 7.06 (br. d, J=8.3 Hz, 1H, NH), 7.22-7.33 (m, 3H), 7.36-7.43 (m, 4H), 7.54 (t, J=7.6 Hz, 1H), 7.95 (d, J=7.8 Hz, 1H). $^1$H NMR (500 MHz, DMSO-d$_6$): 0.92 (t, J=7.3 Hz, 3H), 1.76 (m, 2H), 2.18 (s, 3H), 4.93 (q, J=8.3 Hz, 1H), 7.21-7.41 (m, 6H), 7.59 (t, J=7.7 Hz, 1H), 7.82 (t, J=7.2 Hz, 1H), 8.17 (d, J=7.8 Hz, 1H), 9.1 (br. d, J=8.4 Hz, 1H, NH).

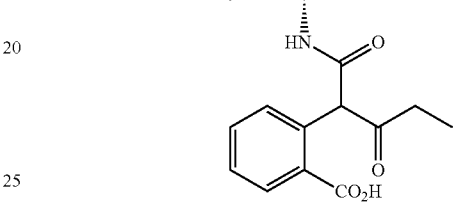

2-[2-oxo-1-((S)-1-phenyl-propylcarbamoyl)-butyl]-benzoic acid

A sealed mixture of 2-[((S)-1-phenyl-propylcarbamoyl)-methyl]-benzoic acid (409 mg, 1.38 mmol), propionic anhydride (10 ml) and 4-N,N-dimethylaminopyridine (15 mg) was heated under microwave irradiation at 150° C. for 20 min and partitioned between 1M HCl (50 ml) and ethyl acetate (100 ml). The organic layer was washed with sat. aq. NaHCO$_3$ (2×50 ml) and brine and concentrated in vacuo. To the obtained residue methanol (25 ml) tetrahydrofurane (25 ml) and 2M aq. NaOH (50 ml) was added and stirred at r.t. for 1 hour. The organic volatiles were removed in vacuo and the pH was adjusted to 1 with 3M aq. HCl. The crude title product (495 mg) was separated by extraction with ethyl acetate (150 ml) and used in the next step without further purification. $^1$H NMR (500 MHz, DMSO-d$_6$): a mixture of tautomers and diastereoisomers.

The following compound was obtained analogously:

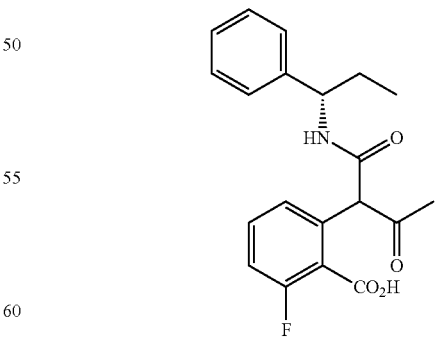

2-Fluoro-6-[2-oxo-1-((S)-1-phenyl-propylcarbamoyl)-propyl]-benzoic acid

LC-MS (m/z) 358.4 (MH$^+$); t$_R$=1.17.

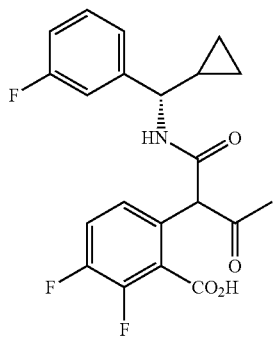

6-(1-{[(S)-Cyclopropyl-(3-fluoro-phenyl)-methyl]-carbamoyl}-2-oxo-propyl)-2,3-difluoro-benzoic acid LC-MS (m/z) 406.4 (MH$^+$); $t_R$=1.26

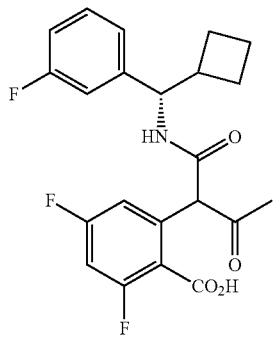

2-(1-{[(S)-Cyclobutyl-(3-fluoro-phenyl)-methyl]-carbamoyl}-2-oxo-propyl)-4,6-difluoro-benzoic acid 2-({[(S)-Cyclobutyl-(3-fluoro-phenyl)-methyl]-carbamoyl}-methyl)-4,6-difluoro-benzoic acid (3.4 g, 9.0 mmol in acetic anhydride (60 mL) was stirred at 100° C. overnight then evaporated and co-evaporated with toluene twice in vacuo to give a mixture of 4-acetyl-3-{[(S)-cyclobutyl-(3-fluoro-phenyl)-methyl]-amino}-6,8-difluoro-2-benzopyran-1-one and 6,8-difluoro-3-methyl-1-oxo-1H-2-benzopyran-4-carboxylic acid [(S)-cyclobutyl-(3-fluoro-phenyl)-methyl]-amide. The obtained residue was dissolved in tetrahydrofuran (15 mL), allowed to cool on an ice-water bath and 2M aqueous NaOH (18 mL) was added. The cold bath removed and the reaction mixture was stirred for 30 min. The obtained mixture was diluted with water (20 mL) and extracted with isopropyl acetate (40 mL) which was washed with water (40 mL). The combined aqueous phase was cooled on ice bath and the pH was adjusted to 1 with conc. HCl. The title product was separated by extraction with isopropylacetate (2×40 mL) and purified by flash chromatography (50 g SiO$_2$, the product was eluted with 1:1 ethyl acetate-heptane, 1.58 g, yield 42%). LC-MS (m/z) 420.6 (MH$^+$); $t_R$=1.35.

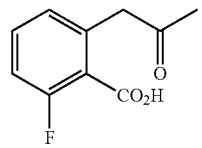

2-Fluoro-6-(2-oxo-propyl)-benzoic acid

2-Carboxymethyl-6-fluoro-benzoic acid (11.16 g, 56.32 mmol) in acetic anhydride (65 mL, 690 mmol) was heated at 110° C. for 60 minutes. Pyridine (20 mL, 250 mmol) was added. Gas evolution was observed. The reaction mixture was refluxed overnight and rotovaped. The residue was dissolved in tetrahydrofuran (100 mL) and 4 M aq. NaOH (100 mL) was added. The reaction mixture was stirred at room temperature for 2 hours. The reaction mixture was acidified with conc. HCl (aq). The two phases were separated and the aqueous phase was extracted with ethyl acetate (2×300 mL). The combined organic phases were washed with brine, dried over MgSO$_4$ and rotavaped. 20 mL toluene was added and the mixture was rotovaped to give crude 2-Fluoro-6-(2-oxo-propyl)-benzoic acid (12.3 g, yield 55.7%, purity ca. 50%). The purity was estimated by $^1$H NMR and the crude product was used in the next step without further purification.

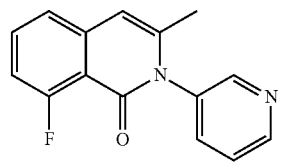 [SMILES: Cc1cc2cccc(F)c2c(=O)n1-c1cccnc1]

8-Fluoro-3-methyl-2-pyridin-3-yl-2H-isoquinolin-1-one

2-Fluoro-6-(2-oxo-propyl)-benzoic acid (12.33 g, 31.43 mmol) and 3-aminopyridine (5.12 g, 54.4 mmol) in 25 mL dioxane were refluxed overnight. The reaction mixture was poured into water (250 mL). The mixture was extracted with ethyl acetate (200 mL). The organic phase was washed with brine, dried over MgSO$_4$ and filtered through a pad of silica gel. The silica gel pad was washed with 250 mL ethyl acetate. The organic fractions were combined and rotavaped. The crude product was flash chromatographed on silica gel (eluent: 50% heptane/ethyl acetate to ethyl acetate) to obtain the product as a pale pink solid (1.3 g, yield 16.3%). LC-MS (m/z) 255.5 (MH$^+$); $t_R$=0.64. $^1$H NMR (500 MHz, CDCl$_3$): 1.99 (s, 3H, Me), 6.43 (s, 1H), 7.07 (dd, J=8.12 Hz, J=11.3 Hz, 1H), 7.24 (d, J=7.9 Hz, 1H), 7.49 (dd, J=4.9 Hz, J=8.1 Hz, 1H), 7.58 (td, J(d)=4.8 Hz, J(t)=8 Hz, 1H), 7.64 (unresolved dt, J(d)=8.1 Hz, J(t)=ca. 1.5 Hz, 1H), 8.53 (d, J=2 Hz, 1H), 8.71 (d, J=4.8 Hz, J=0.9 Hz, 1H).

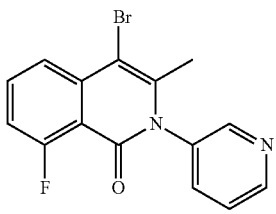 [SMILES: Cc1c(Br)c2cccc(F)c2c(=O)n1-c1cccnc1]

3-Bromo-8fluoro-3-methyl-2-pyridin-3-yl-2H-isoquinolin-1-one

8-Fluoro-3-methyl-2-pyridin-3-yl-2H-isoquinolin-1-one (550 mg, 2.2 mmol) and N-bromosuccinimide (396 mg, 2.23 mmol) were dissolved in N,N-dimethylformamide (10 mL). The reaction mixture was stirred at 50° C. for 60 minutes and poured into diethyl ether (50 mL) and ethyl acetate (20 mL). A white solid precipitated, which was removed by filtration. The filtrate was washed with diluted brine (water/sat. NaCl (aq.)=1:1; 4×20 mL), dried over MgSO$_4$ and rotavaped. $^1$H NMR (500 MHz, CDCl$_3$): 2.27 (s, 3H, Me), 7.2 (dd, J=8.4 Hz, J=10.7 Hz, 1H), 7.52 (dd, J=4.9 Hz, J=7.9 Hz, 1H), 7.64 (d (d of unresolved m), J=8 Hz, 1H), 7.72 (td, J(d)=5 Hz, J(t)=8.1 Hz, 1H), 7.84 (d, J=8.2 Hz), 8.53 (d, J=1.8 Hz, 1H), 8.74 (d, J=4.3 Hz, 1H).

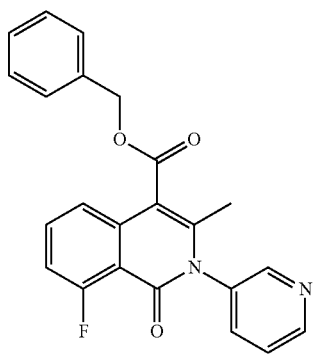 [SMILES: Cc1c(C(=O)OCc2ccccc2)c2cccc(F)c2c(=O)n1-c1cccnc1]

8-Fluoro-3-methyl-1-oxo-2-pyridin-3-yl-1,2-dihydro-isoquinoline-4-carboxylic acid benzyl ester 4-Bromo-8-fluoro-3-methyl-2-pyridin-3-yl-2H-isoquinolin-1-one (320 mg, 0.96 mmol) and benzyl alcohol (300 μL, 2.90 mmol) were added to palladium (II) acetate (22 mg, 0.096 mmol) and 4,5-bis-diphenylphosphanyl-9,9-dimethyl-9H-xanthene (56 mg, 0.096 mmol) and sodium carbonate (305 mg, 2.88 mmol) in toluene (3 mL). The reaction mixture was stirred under an atmosphere of carbon monoxide at 100° C. for 2 days. The reaction mixture was poured onto a 25 g silica gel column and it was flash chromatographed (gradient: heptane-ethyl acetate) to give the title compound (151 mg, yield 40.5%). LC-MS (m/z) 389.2 (MH$^+$); t$_R$=1.15. $^1$H NMR (500 MHz, CDCl$_3$): 1.96 (s, 3H, Me), 5.42 (s, 2H), 7.12 (dd, J=8.3 Hz, J=10.9 Hz, 1H), 7.31 (d, J=8.2 Hz, 1H), 7.35-7.42 (m, 3H), 7.43-7.5 (m, 3H), 7.55-7.63 (m, 2H), 8.5 (d, J=2.1 Hz, 1H), 8.71 (dd, J=4.7 Hz, J=1 Hz, 1H).

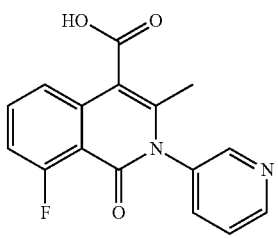 [SMILES: Cc1c(C(=O)O)c2cccc(F)c2c(=O)n1-c1cccnc1]

8-Fluoro-3-methyl-1-oxo-2-pyridin-3-yl-1,2-dihydro-isoquinoline-4-carboxylic acid 8-Fluoro-3-methyl-1-oxo-2-pyridin-3-yl-1,2-dihydro-isoquinoline-4-carboxylic acid benzyl ester (0.150 g, 0.386 mmol) was dissolved in methanol (2 mL) and added to 10% Palladium on Charcoal (10 mg). The reaction mixture was stirred under an atmosphere of hydrogen for 60 minutes at room temperature. The reaction mixture was filtered and was rotovaped to give the title compound (0.105 g; yield 91.2%) as a yellow oil. Alternatively, the title acid can be obtained directly under the same conditions according to the above described Pd-catalysed carbonylation in the presence of water instead of benzyl alcohol. LC-MS (m/z) 299.3 (MH$^+$); t$_R$=0.43. $^1$H NMR (500 MHz, CDCl$_3$): 2.15 (s, 3H), 7.16 (m, 1H), 7.59 (m, 1H), 7.61-7.7 (m, 2H), 7.73 (m, 1H), 8.6 (br. s, 1H), 8.78 (br., 1H).

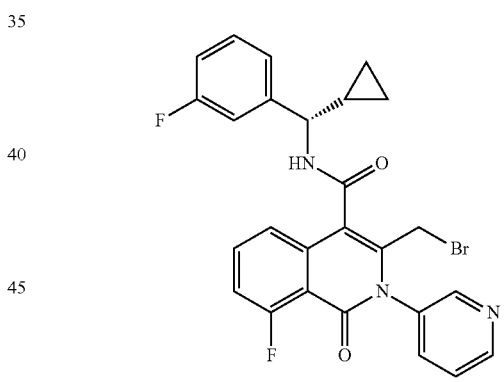

3-Bromomethyl-8-fluoro-1-oxo-2-pyridin-3-yl-1,2-dihydro-isoquinoline-4-carboxylic acid[(S)-cyclopropyl-(3-fluoro-phenyl)-methyl]-amide Bromine (220 mg, 1.3 mmol) in 0.5 ml 1,2-dichloroethane was added to 8-fluoro-3-methyl-1-oxo-2-pyridin-3-yl-1,2-dihydro-isoquinoline-4-carboxylic acid[(S)-cyclopropyl-(3-fluoro-phenyl)-methyl]-amide (200 mg, 0.450 mmol) in 1,2-dichloroethane (5 mL) at 60° C. The reaction mixture was stirred for 15 minutes at 60° C. The reaction mixture was concentrated in vacuo to give crude 3-bromomethyl-8-fluoro-1-oxo-2-pyridin-3-yl-1,2-dihydro-isoquinoline-4-carboxylic acid[(S)-cyclopropyl-(3-fluoro-phenyl)-methyl]-amide, which was used in the next step without purification.

COMPOUNDS OF THE INVENTION

Example 1

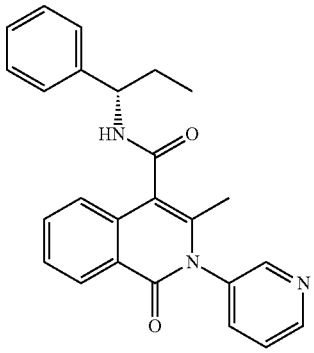 [SMILES: CC[C@H](NC(=O)c1c(C)n(-c2cccnc2)c(=O)c2ccccc12)c1ccccc1]

1a 3-Methyl-1-oxo-2-pyridin-3-yl-1,2-dihydro-isoquinoline-4-carboxylic acid ((S)-1-phenyl-propyl)-amide A mixture of 4-acetyl-3-((S)-1-phenyl-propylamino)-isochromen-1-one (100 mg) and 3-aminopyridine (400 mg, excess) in acetonitrile (0.2 mL) was heated under microwave irradiation at 170° C. for 15 min. The reaction mixture was partitioned between water (20 ml) and ethyl acetate (20 ml), and the organic phase was washed with water (3×10 ml). The product was extracted into aqueous phase with aq. 2M HCl (10 ml), the aqueous solution was neutralised with aq. 10% $Na_2CO_3$ and extracted again with ethyl acetate and evaporated. The obtained residue was purified by flash chromatography on $SiO_2$ (5 g, gradient heptane-ethyl acetate, the product came out with 100% ethyl acetate) to give 37 mg of oil, which was precipitated from methanol (0.1 mL) and water (10 mL) with sonication for 10 min. The title compound was separated by filtration to give 10 mg of brown solid. LC-MS (m/z) 398.1 (MH$^+$); $t_R$=1.06. $^1$H NMR (250 MHz, 70° C., DMSO-$d_6$): 0.93 (t, J=7.4 Hz, 3H, Me of Et), 1.72-1.88 (overlapping m, $CH_2$ of Et), 1.85 (overlapping s, 3H, Me), 4.97 (q (dt), J=8 Hz, J=6.9 Hz, 1H, CHNH), 7.23 (m, 1H), 7.28-7.42 (m, 5H), 7.49 (t, J=7.6 Hz, 1H), 7.59 (dd, J=4.8 Hz, J=8.1 Hz, 1H), 7.69 (t, J=7.7 Hz, 1H), 7.76 (d of dd, J=8.1 Hz, J=2.4 Hz, J=1.4 Hz, 1H), 8.21 (dd, J=8 Hz, J=0.8 Hz, 1H), 8.49 (d, J=2.4 Hz), 8.67 (dd, J=4.7 Hz, J=2.4 Hz, 1H), 8.72 (br d, J=8.2 Hz, NHCO).

The following compounds were obtained analogously from corresponding ketene-aminals of the general formula XXIII and appropriate aminoheterocycles of the general formula VI:

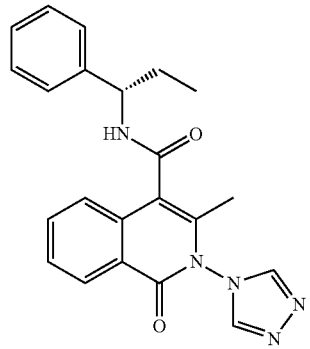

1b 3-Methyl-1-oxo-2-[1,2,4]-triazol-4-yl-1,2-dihydro-isoquinoline-4-carboxylic acid ((S)-1-phenyl-propyl)-amide The title compound was isolated by preparative LC-MS. LC-MS (m/z) 388.3 (MH$^+$); $t_R$=1.03.

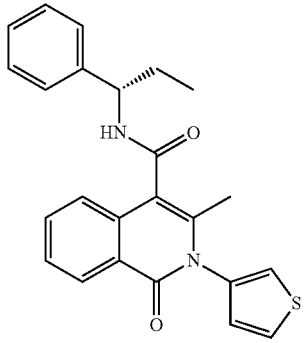 [SMILES: CC[C@H](NC(=O)c1c(C)n(-c2ccsc2)c(=O)c2ccccc12)c1ccccc1]

1c 3-Methyl-1-oxo-2-thiophen-3-yl-1,2-dihydro-isoquinoline-4-carboxylic acid ((S)-1-phenyl-propyl)-amide The reaction was run at +150° C. for 15 min. LC-MS (m/z) 403.4 (MH$^+$); $t_R$=1.37. $^1$H NMR (250 MHz, 70° C., DMSO-$d_6$): 0.94 (t, J=7.3 Hz, 3H, Me of Et), 1.73-1.91 (m, $CH_2$ of Et), 1.93 (s, 3H, Me), 4.98 (q (dt), J=8 Hz, J=6.9 Hz, 1H, CHNH), 7.03 (dd, J=5.1 Hz, J=1.2 Hz, 1H), 7.21-7.42 (m, 6H), 7.44-7.55 (m, 2H), 7.62-7.71 (m, 2H), 8.21 (d, J=7.5 Hz, 1H), 8.73 (br d, J=8.1 Hz, NHCO).

Example 2

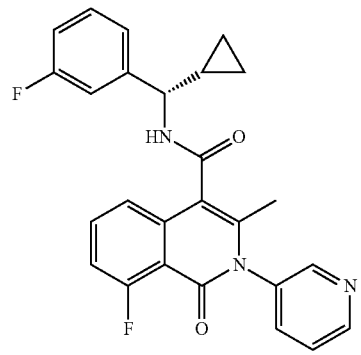 [SMILES: Cc1c(C(=O)N[C@H](c2cccc(F)c2)C2CC2)c2cccc(F)c2c(=O)n1-c1cccnc1]

2a 8-Fluoro-3-methyl-1-oxo-2-pyridin-3-yl-1,2-dihydro-isoquinoline-4-carboxylic acid [(S)-cyclopropyl-(3-fluoro-phenyl)-methyl]-amide A suspension of 2-(1-{[(S)-cyclopropyl-(3-fluoro-phenyl)-methyl]-carbamoyl}-2-oxo-propyl)-6-fluoro-benzoic acid (12.86 g, 33.2 mmol) and 3-aminopyridine (20.00 g, 212.5 mmol) in acetonitrile (19 mL) was heated under microwave irradiation at +150° C. for 60 min. It was poured into a mixture of ice (200 g) and 1% aq. $NaHCO_3$ (100 ml) and extracted with ethyl acetate (300 ml), washed with 1% aq. $NaHCO_3$ (3×100 ml) and brine (50 ml), dried ($Na_2SO_4$) and evaporated to give 15.2 g of dark brown oil. The crude product was transferred into a 100 g $SiO_2$ column with 1,2-dichloroethane and flash chromatographed (gradient 50% to 100% ethyl acetate in heptane). The product came out with 75-100% ethyl acetate to give 3.8 g of pale purple foam, which was precipitated from 10 ml MeOH and 100 g of ice with sonication (30 min) to give 3.23 mg of the title compound, yield 23%. Alternatively, the condensation was performed in toluene instead of acetonitrile under reflux for 16 hours and the product was separated as above, yield 64%. LC-MS (m/z) 446.1 (MH$^+$); $t_R$=1.07. $^1$H NMR (250 MHz, 70° C., DMSO-d$_6$, DMSO-d$_5$=2.5 ppm): 0.42-0.54 (complex m, 2H), 0.53-0.66 (complex m, 2H), 1.27 (complex m, 1H), 1.9 (s, 3H, Me), 4.52 (t, J=8.7 Hz, 1H, CHNH), 7.07 (ddt, J(t)=8.2 Hz, J=2.7 Hz, J=1.1 Hz, 1H), 7.17-7.33 (m, 4H), 7.4 (dt, J(t)=, 7.6 Hz, J(d)=6.2 Hz, 1H), 7.61 (ddd, J=0.7 Hz, J=4.7 Hz, J=8.1 Hz, 1H), 7.72 (dt, J(t)=8.1 Hz, J(d)=5.2 Hz, 1H), 7.79 (td (unres. ddd), J(d)=8.1 Hz, J=2 Hz, 1H), 8.52 (d, J=2.3 Hz, 1H), 8.69 (dd, J=1.5 Hz, J=4.8 Hz, 1H), 8.96 (br d, J=8.3 Hz, NHCO).

The following compounds were obtained analogously from corresponding acid-catamites of the general formula XXV and aminoheterocycles of the general formula VI:

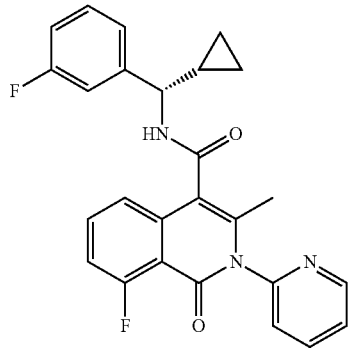

2b 8-Fluoro-3-methyl-1-oxo-2-pyridin-2-yl-1,2-dihydro-isoquinoline-4-carboxylic acid [(S)-cyclopropyl-(3-fluoro-phenyl)-methyl]-amide LC-MS (m/z) 446.5 (MH$^+$); $t_R$=1.25. $^1$H NMR (250 MHz, 70° C., DMSO-d$_6$, DMSO-d$_5$=2.5 ppm): 0.41-0.53 (complex m, 2H), 0.52-0.64 (complex m, 2H), 1.27 (complex m, 1H), 1.86 (s, 3H, Me), 4.51 (t, J=8.7 Hz, 1H, CHNH), 7.06 (ddt, J(t)=8.1 Hz, J=2.8 Hz, J=1.1 Hz), 7.15-7.34 (m, 4H), 7.39 (dt, J(t)=7.8 Hz, J(d)=6.2 Hz, 1H), 7.49 (d, J=8 Hz, 1H), 7.54 (ddd, J=7.6 Hz, J=4.7 Hz, J=0.8 Hz), 7.7 (dt, J(t)=8.1 Hz, J(d)=5.1 Hz, 1H), 8.05 (dt, J(t)=7.7 Hz, J(d)=2 Hz, 1H), 8.66 (ddd, J=1 Hz, J=2 Hz, J=4.8 Hz, 1H), 9.06 (br d, J=8.2 Hz, NHCO).

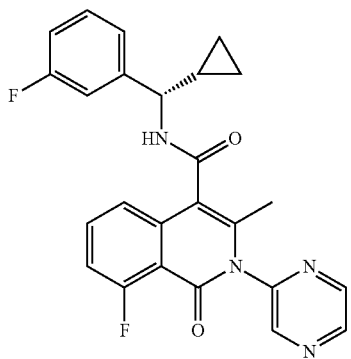 [SMILES: Cc1c(C(=O)N[C@H](c2cccc(F)c2)C2CC2)c2cccc(F)c2c(=O)n1-c1cnccn1]

2c 8-Fluoro-3-methyl-1-oxo-2-pyrazin-2-yl-1,2-dihydro-isoquinoline-4-carboxylic acid [(S)-cyclopropyl-(3-fluoro-phenyl)-methyl]-amide LC-MS (m/z) 447.6 (MH$^+$); $t_R$=1.19. $^1$H NMR (250 MHz, 70° C., DMSO-d$_6$, DMSO-d$_5$=2.5 ppm): 0.42-0.54 (complex m, 2H), 0.54-0.65 (complex m, 2H), 1.27 (complex m, 1H), 1.89 (s, 3H, Me), 4.51 (t, J=8.7 Hz, 1H, CHNH), 7.06 (ddt, J(t)=8.2 Hz, J=2 Hz, J=1 Hz, 1H), 7.2-7.32 (m, 4H), 7.4 (dt, J(t)=8 Hz, J(d)=6.1 Hz, 1H), 7.74 (dt, J(t)=8.1 Hz, J(d)=5.1 Hz, 1H), 8.76-8.84 (m, 3H), 9.1 (br d, J=8.2 Hz, NHCO).

The following compounds were obtained analogously by condensation at 170° C. (15 min) in acetonitrile followed by purification by preparative LC-MS.

| Chemical name | Structure | $t_R$ (min) | m/z (MH$^+$) | MW |
|---|---|---|---|---|
| 2d 2-(6-Chloro-pyridin-3-yl)-8-fluoro-3-methyl-1-oxo-1,2-dihydro-isoquinoline-4-carboxylic acid [(S)-cyclopropyl-(3-fluoro-phenyl)-methyl]-amide | 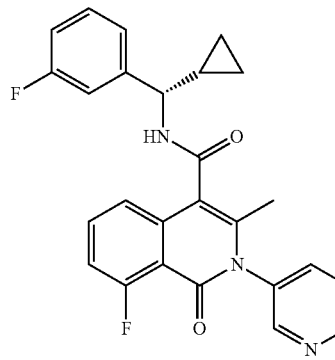 | 1.39 | 480.2 | 479.91 |

| | Chemical name | Structure | $t_R$ (min) | m/z (MH$^+$) | MW |
|---|---|---|---|---|---|
| 2e | 8-Fluoro-2-(6-methoxy-pyridin-3-yl)-3-methyl-1-oxo-1,2-dihydro-isoquinoline-4-carboxylic acid [(S)-cyclopropyl-(3-fluoro-phenyl)-methyl]-amide | 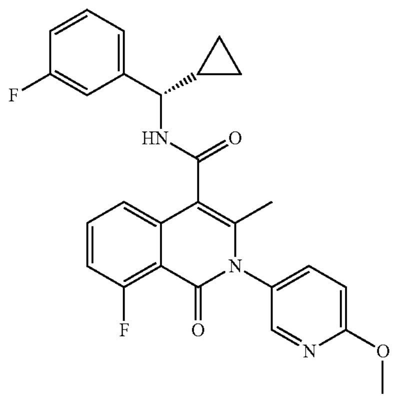 [SMILES: COc1ccc(-n2c(C)c(C(=O)N[C@H](c3cccc(F)c3)C3CC3)c3cccc(F)c3c2=O)cn1] | 1.36 | 476.3 | 475.49 |
| 2f | 2-(2-Amino-pyridin-3-yl)-8-fluoro-3-methyl-1-oxo-1,2-dihydro-isoquinoline-4-carboxylic acid [(S)-cyclopropyl-(3-fluoro-phenyl)-methyl]-amide | 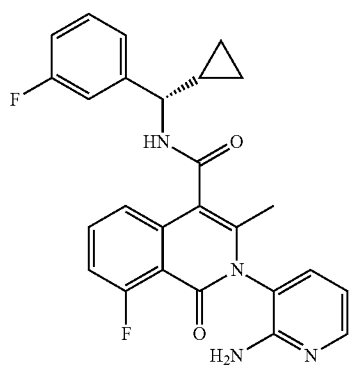 [SMILES: Cc1c(C(=O)N[C@H](c2cccc(F)c2)C2CC2)c2cccc(F)c2c(=O)n1-c1cccnc1N] | 0.89 | 461.5 | 460.48 |
| 2j | 8-Fluoro-2-(2-fluoro-pyridin-3-yl)-3-methyl-1-oxo-1,2-dihydro-isoquinoline-4-carboxylic acid [(S)-cyclopropyl-(3-fluoro-phenyl)-methyl]-amide | 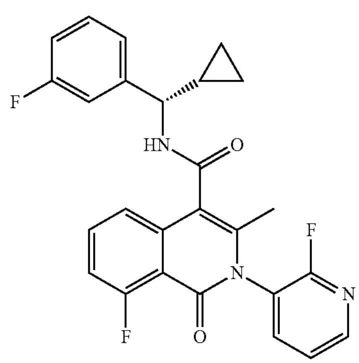 [SMILES: Cc1c(C(=O)N[C@H](c2cccc(F)c2)C2CC2)c2cccc(F)c2c(=O)n1-c1cccnc1F] | 1.31 | 464.4 | 463.45 |
| 2k | 8-Fluoro-3-methyl-1-oxo-2-pyrimidin-5-yl-1,2-dihydro-isoquinoline-4-carboxylic acid [(S)-cyclopropyl-(3-fluoro-phenyl)-methyl]-amide | 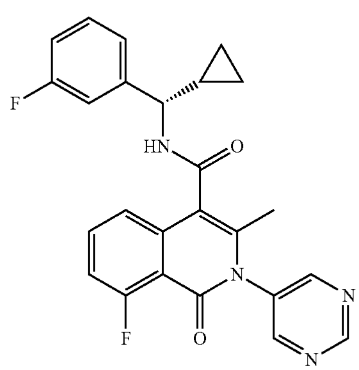 [SMILES: Cc1c(C(=O)N[C@H](c2cccc(F)c2)C2CC2)c2cccc(F)c2c(=O)n1-c1cncnc1] | 1.16 | 447.5 | 446.45 |

-continued

| | Chemical name | Structure | $t_R$ (min) | m/z (MH$^+$) | MW |
|---|---|---|---|---|---|
| 2l | 8-Fluoro-3-methyl-2-(6-methyl-pyridin-3-yl)-1-oxo-1,2-dihydro-isoquinoline-4-carboxylic acid [(S)-cyclopropyl-(3-fluoro-phenyl)-methyl]-amide | 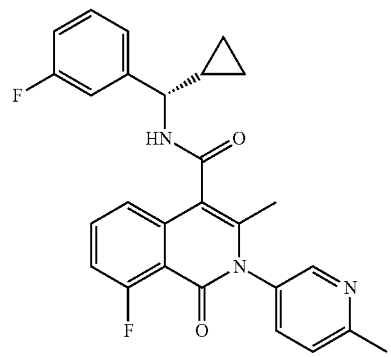 [SMILES: Cc1ccc(-n2c(C)c(C(=O)N[C@H](c3cccc(F)c3)C3CC3)c3cccc(F)c3c2=O)cn1] | 1.03 | 460.6 | 459.49 |
| 2m | 8-Fluoro-3-methyl-2-(2-methyl-pyridin-3-yl)-1-oxo-1,2-dihydro-isoquinoline-4-carboxylic acid [(S)-cyclopropyl-(3-fluoro-phenyl)-methyl]-amide | 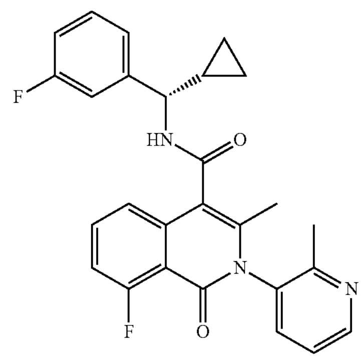 [SMILES: Cc1ncccc1-n1c(C)c(C(=O)N[C@H](c2cccc(F)c2)C2CC2)c2cccc(F)c2c1=O] | 1.03 | 460.5 | 459.49 |
| 2n | 8-Fluoro-2-(6-fluoro-pyridin-3-yl)-3-methyl-1-oxo-1,2-dihydro-isoquinoline-4-carboxylic acid [(S)-cyclopropyl-(3-fluoro-phenyl)-methyl]-amide | 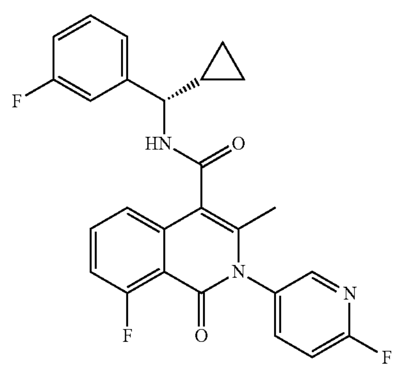 [SMILES: Cc1c(C(=O)N[C@H](c2cccc(F)c2)C2CC2)c2cccc(F)c2c(=O)n1-c1ccc(F)nc1] | 1.32 | 464.4 | 463.45 |
| 2o | 8-Fluoro-3-methyl-2-(4-methyl-pyridin-3-yl)-1-oxo-1,2-dihydro-isoquinoline-4-carboxylic acid [(S)-cyclopropyl-(3-fluoro-phenyl)-methyl]-amide | 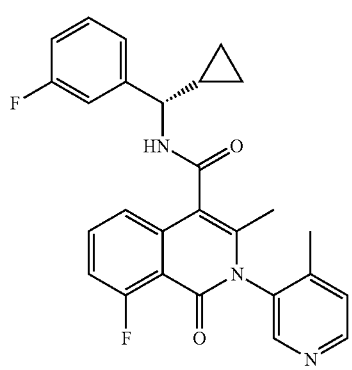 [SMILES: Cc1ccncc1-n1c(C)c(C(=O)N[C@H](c2cccc(F)c2)C2CC2)c2cccc(F)c2c1=O] | 1.05 | 460.7 | 459.49 |

-continued

| | Chemical name | Structure | $t_R$ (min) | m/z (MH$^+$) | MW |
|---|---|---|---|---|---|
| 2p | 8-Fluoro-3-methyl-2-(5-methyl-pyridin-3-yl)-1-oxo-1,2-dihydro-isoquinoline-4-carboxylic acid [(S)-cyclopropyl-(3-fluoro-phenyl)-methyl]-amide | 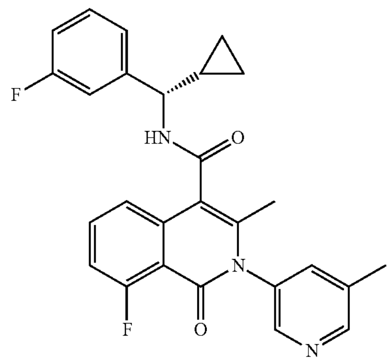 [SMILES: Cc1cncc(-n2c(C)c(C(=O)N[C@H](c3cccc(F)c3)C3CC3)c3cccc(F)c3c2=O)c1] | 1.12 | 460.6 | 459.49 |
| 2r | 8-Fluoro-3-methyl-2-(4-methyl-thiazol-2-yl)-1-oxo-1,2-dihydro-isoquinoline-4-carboxylic acid [(S)-cyclopropyl-(3-fluoro-phenyl)-methyl]-amide | 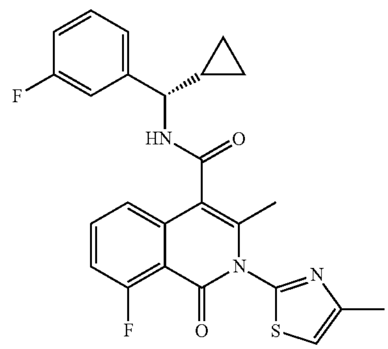 [SMILES: Cc1csc(-n2c(C)c(C(=O)N[C@H](c3cccc(F)c3)C3CC3)c3cccc(F)c3c2=O)n1] | 1.38 | 466.3 | 465.52 |
| 2s | 2-(1,3-Dimethyl-1H-pyrazol-4-yl)-8-fluoro-3-methyl-1-oxo-1,2-dihydro-isoquinoline-4-carboxylic acid [(S)-cyclopropyl-(3-fluoro-phenyl)-methyl]-amide | 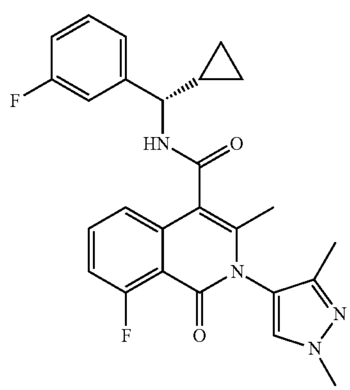 [SMILES: Cc1nn(C)cc1-n1c(C)c(C(=O)N[C@H](c2cccc(F)c2)C2CC2)c2cccc(F)c2c1=O] | 1.2 | 463.4 | 462.50 |
| 2t | 8-Fluoro-3-methyl-2-(2-methyl-imidazol-1-yl)-1-oxo-1,2-dihydro-isoquinoline-4-carboxylic acid [(S)-cyclopropyl-(3-fluoro-phenyl)-methyl]-amide | 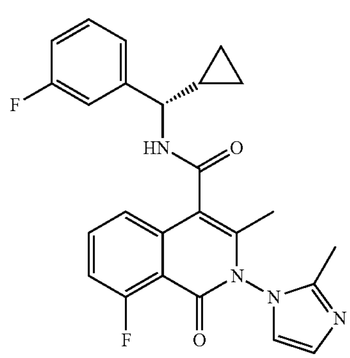 [SMILES: Cc1nccn1-n1c(C)c(C(=O)N[C@H](c2cccc(F)c2)C2CC2)c2cccc(F)c2c1=O] | 0.9 | 449.3 | 448.47 |

| | Chemical name | Structure | $t_R$ (min) | m/z (MH$^+$) | MW |
|---|---|---|---|---|---|
| 2u | 8-Fluoro-3-methyl-1-oxo-2-[1,2,4]triazol-4-yl-1,2-dihydro-isoquinoline-4-carboxylic acid [(S)-cyclopropyl-(3-fluoro-phenyl)-methyl]-amide | 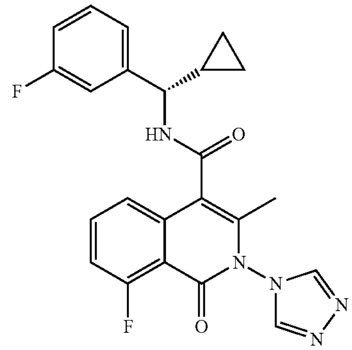 [SMILES: Cc1c(C(=O)N[C@H](c2cccc(F)c2)C2CC2)c2cccc(F)c2c(=O)n1-n1cnnc1] | 1.06 | 436.3 | 435.43 |
| 2v | 2-(5-Ethyl-[1,3,4]thiadiazol-2-yl)-8-fluoro-3-methyl-1-oxo-1,2-dihydro-isoquinoline-4-carboxylic acid [(S)-cyclopropyl-(3-fluoro-phenyl)-methyl]-amide | 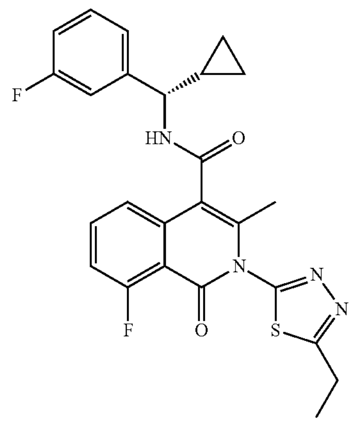 [SMILES: CCc1nnc(-n2c(C)c(C(=O)N[C@H](c3cccc(F)c3)C3CC3)c3cccc(F)c3c2=O)s1] | 1.37 | 481.3 | 480.54 |
| 2w | 8-Fluoro-3-methyl-1-oxo-2-thiazol-2-yl-1,2-dihydro-isoquinoline-4-carboxylic acid [(S)-cyclopropyl-(3-fluoro-phenyl)-methyl]-amide | 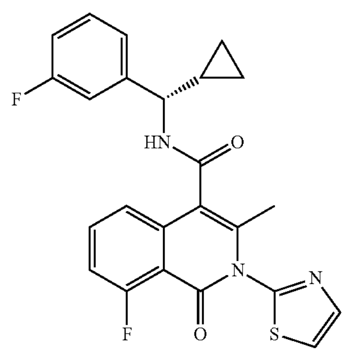 [SMILES: Cc1c(C(=O)N[C@H](c2cccc(F)c2)C2CC2)c2cccc(F)c2c(=O)n1-c1nccs1] | 1.29 | 452.3 | 451.50 |
| 2x | 2-(1H-Benzoimidazol-2-yl)-8-fluoro-3-methyl-1-oxo-1,2-dihydro-isoquinoline-4-carboxylic acid [(S)-cyclopropyl-(3-fluoro-phenyl)-methyl]-amide | 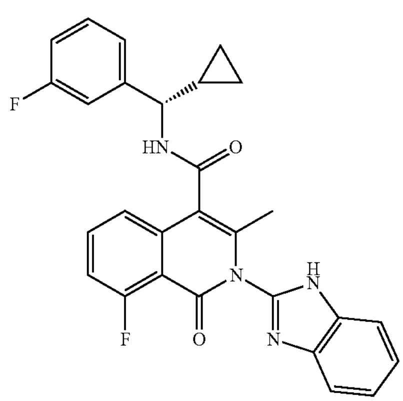 [SMILES: Cc1c(C(=O)N[C@H](c2cccc(F)c2)C2CC2)c2cccc(F)c2c(=O)n1-c1nc2ccccc2[nH]1] | 1.31 | 485.5 | 484.50 |

-continued

| | Chemical name | Structure | $t_R$ (min) | m/z (MH$^+$) | MW |
|---|---|---|---|---|---|
| 2y | 2-(3,5-Dimethyl-[1,2,4]triazol-4-yl)-8-fluoro-3-methyl-1-oxo-1,2-dihydro-isoquinoline-4-carboxylic acid [(S)-cyclopropyl-(3-fluoro-phenyl)-methyl]-amide | 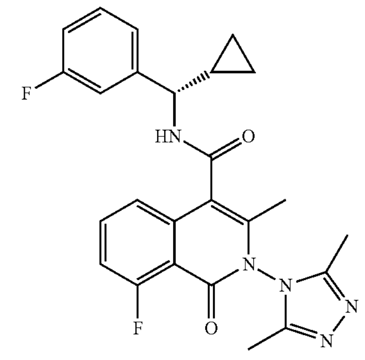 [SMILES: Cc1nnc(C)n1-n1c(C)c(C(=O)N[C@H](c2cccc(F)c2)C2CC2)c2cccc(F)c2c1=O] | 1.12 | 464.5 | 463.49 |
| 2z | 2-(2,5-Dimethyl-2H-pyrazol-3-yl)-8-fluoro-3-methyl-1-oxo-1,2-dihydro-isoquinoline-4-carboxylic acid [(S)-cyclopropyl-(3-fluoro-phenyl)-methyl]-amide | 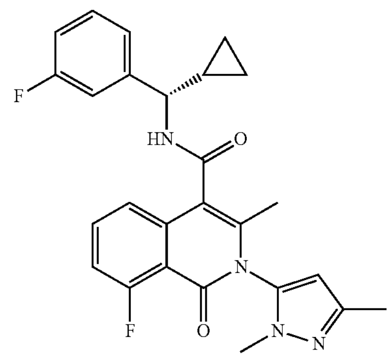 [SMILES: Cc1cc(-n2c(C)c(C(=O)N[C@H](c3cccc(F)c3)C3CC3)c3cccc(F)c3c2=O)n(C)n1] | 1.28 | 463.5 | 462.50 |
| 2aa | 8-Fluoro-3-methyl-2-(5-methyl-isoxazol-3-yl)-1-oxo-1,2-dihydro-isoquinoline-4-carboxylic acid [(S)-cyclopropyl-(3-fluoro-phenyl)-methyl]-amide | 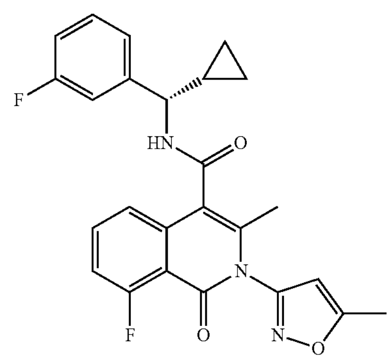 [SMILES: Cc1cc(-n2c(C)c(C(=O)N[C@H](c3cccc(F)c3)C3CC3)c3cccc(F)c3c2=O)no1] | 1.37 | 450.3 | 449.45 |
| 2ab | 8-Fluoro-3-methyl-2-(5-methyl-[1,3,4]thiadiazol-2-yl)-1-oxo-1,2-dihydro-isoquinoline-4-carboxylic acid [(S)-cyclopropyl-(3-fluoro-phenyl)-methyl]-amide | 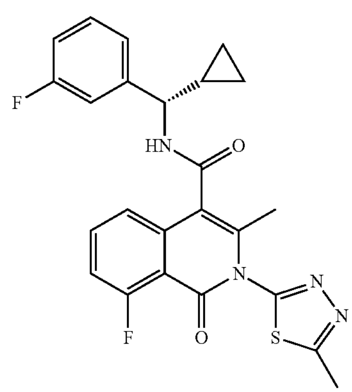 [SMILES: Cc1nnc(-n2c(C)c(C(=O)N[C@H](c3cccc(F)c3)C3CC3)c3cccc(F)c3c2=O)s1] | 1.3 | 467.2 | 466.51 |

| Chemical name | Structure | $t_R$ (min) | m/z (MH⁺) | MW |
|---|---|---|---|---|
| 2ac 8-Fluoro-3-methyl-1-oxo-2-pyrrol-1-yl-1,2-dihydro-isoquinoline-4-carboxylic acid [(S)-cyclopropyl-(3-fluoro-phenyl)-methyl]-amide | | 1.42 | 434.5 | 433.46 |
| 2ad 8-Fluoro-3-methyl-2-(5-methyl-thiazol-2-yl)-1-oxo-1,2-dihydro-isoquinoline-4-carboxylic acid [(S)-cyclopropyl-(3-fluoro-phenyl)-methyl]-amide | | 1.39 | 466.4 | 465.52 |
| 2ae 2-(3-Cyano-thiophen-2-yl)-8-fluoro-3-methyl-1-oxo-1,2-dihydro-isoquinoline-4-carboxylic acid [(S)-cyclopropyl-(3-fluoro-phenyl)-methyl]-amide | | 1.4 | 476.2 | 475.52 |
| 2af 8-Fluoro-2-isoxazol-3-yl-3-methyl-1-oxo-1,2-dihydro-isoquinoline-4-carboxylic acid [(S)-cyclopropyl-(3-fluoro-phenyl)-methyl]-amide | | 1.27 | 436.4 | 435.43 |

| Chemical name | Structure | $t_R$ (min) | m/z (MH$^+$) | MW |
|---|---|---|---|---|
| 2ag 8-Fluoro-3-methyl-2-(1-methyl-1H-pyrazol-3-yl)-1-oxo-1,2-dihydro-isoquinoline-4-carboxylic acid [(S)-cyclopropyl-(3-fluoro-phenyl)-methyl]-amide | | 1.15 | 449.4 | 448.47 |

Example 3

The following compounds were prepared analogously as in example 2a from 2-(1-{[(S)-cyclobutyl-(3-fluoro-phenyl)-methyl]-carbamoyl}-2-oxo-propyl)-6-fluoro-benzoic acid and appropriate aminoheterocycle of the general formula VI:

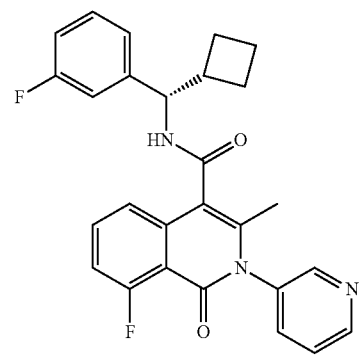

3a 8-Fluoro-3-methyl-1-oxo-2-pyridin-3-yl-1,2-dihydro-isoquinoline-4-carboxylic acid [(S)-cyclobutyl-(3-fluoro-phenyl)-methyl]-amide LC-MS (m/z) 460.4 (MH$^+$); $t_R$=1.22. $^1$H NMR (250 MHz, 100° C., DMSO-d$_6$, DMSO-d$_5$=2.5 ppm): 1.9 (overlapping s, 3H, Me), 1.78-2.17 (overlapping m, 6H), 2.78 (m, 1H), 5.08 (t, J=9 Hz, 1H, C<u>H</u>NH), 7.03 (ddt, J(t)=8.5 Hz, J=3 Hz, J=1 Hz, 1H), 7.12-7.25 (m, 4H), 7.37 (dt, J(t)=8 Hz, J(d)=6.2 Hz, 1H), 7.59 (ddd, J=0.8 Hz, J=4.8 Hz, J=8.1 Hz, 1H), 7.66 (dt, J(t)=8.1 Hz, J(d)=5.2 Hz, 1H), 7.76 (ddd, J(d)=8.1 Hz, J=2.4 Hz, J=1.6 Hz, 1H), 8.5 (d, J=2.3 Hz, 1H), 8.55 (br d, J=8.3 Hz, NHCO), 8.68 (dd, J=1.6 Hz, J=4.8 Hz, 1H).

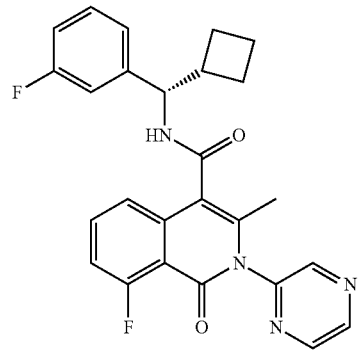 [SMILES: Cc1c(C(=O)N[C@H](c2cccc(F)c2)C2CCC2)c2cccc(F)c2c(=O)n1-c1cnccn1]

3b 8-Fluoro-3-methyl-1-oxo-2-pyrazin-2-yl-1,2-dihydro-isoquinoline-4-carboxylic acid [(S)-cyclobutyl-(3-fluoro-phenyl)-methyl]-amide LC-MS (m/z) 461.6 (MH$^+$); $t_R$=1.34.

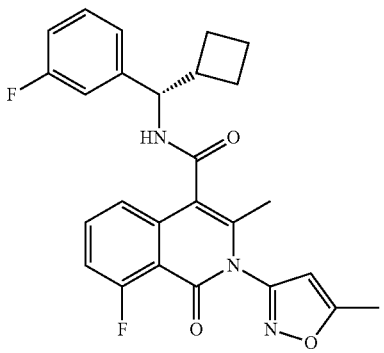 [SMILES: Cc1cc(-n2c(C)c(C(=O)N[C@H](c3cccc(F)c3)C3CCC3)c3cccc(F)c3c2=O)no1]

3c 8-Fluoro-3-methyl-2-(5-methyl-isoxazol-3-yl)-1-oxo-1,2-dihydro-isoquinoline-4-carboxylic acid [(S)-cyclobutyl-(3-fluoro-phenyl)-methyl]-amide LC-MS (m/z) 464.5 (MH$^+$); $t_R$=1.49.

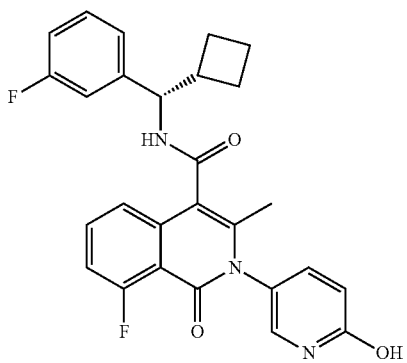 [SMILES: Cc1c(C(=O)N[C@H](c2cccc(F)c2)C2CCC2)c2cccc(F)c2c(=O)n1-c1ccc(O)nc1]

3d 8-Fluoro-2-(6-hydroxy-pyridin-3-yl)-3-methyl-1-oxo-1,2-dihydro-isoquinoline-4-carboxylic acid [(S)-cyclobutyl-(3-fluoro-phenyl)-methyl]-amide LC-MS (m/z) 476.3 (MH$^+$); $t_R$=1.14.

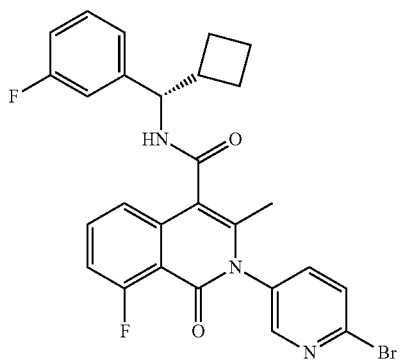 [SMILES: Cc1c(C(=O)N[C@H](c2cccc(F)c2)C2CCC2)c2cccc(F)c2c(=O)n1-c1ccc(Br)nc1]

3e 2-(6-Bromo-pyridin-3-yl)-8-fluoro-3-methyl-1-oxo-1,2-dihydro-isoquinoline-4-carboxylic acid [(S)-cyclobutyl-(3-fluoro-phenyl)-methyl]-amide The corresponding reaction mixture with 5-amino-2-bromopyridine (1.8 eq.) was stirred in toluene at 120° C. for 16 hours. The title product was isolated by preparative LC-MS. LC-MS (m/z) 538.5 & 540.5 (MH$^+$); $t_R$=1.48 (method A), 0.82 (method B).

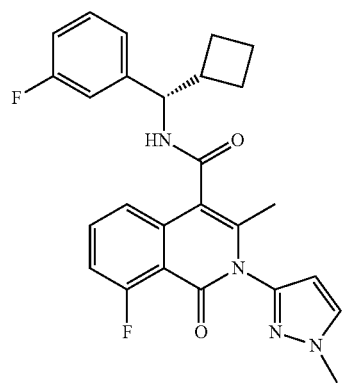 [SMILES: Cc1c(C(=O)N[C@H](c2cccc(F)c2)C2CCC2)c2cccc(F)c2c(=O)n1-c1ccn(C)n1]

3f 8-Fluoro-3-methyl-2-(1-methyl-1H-pyrazol-3-yl)-1-oxo-1,2-dihydro-isoquinoline-4-carboxylic acid [(S)-cyclobutyl-(3-fluoro-phenyl)-methyl]-amide The corresponding reaction mixture with 1-methyl-1H-pyrazol-3-amine (3 eq.) was microwaved in acetonitrile at 150° C. for 10 min. The title product was isolated by preparative LC-MS. LC-MS (m/z) 463.4 (MH$^+$); $t_R$=1.28.

Example 4

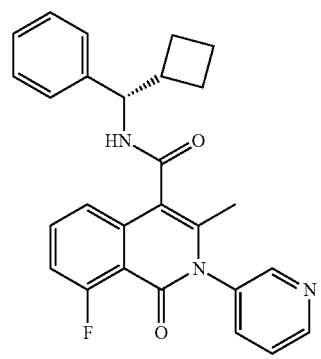 [SMILES: Cc1c(C(=O)N[C@H](c2ccccc2)C2CCC2)c2cccc(F)c2c(=O)n1-c1cccnc1]

4a 8-Fluoro-3-methyl-1-oxo-2-pyridin-3-yl-1,2-dihydro-isoquinoline-4-carboxylic acid ((S)-cyclobutyl-phenyl-methyl)-amide A mixture of 4-bromo-8-fluoro-3-methyl-2-pyridin-3-yl-2H-isoquinolin-1-one (93 mg, 0.28 mmol), C-((S)-C-Cyclobutyl-C-phenyl)-methylammonium chloride (61 mg, 0.31 mmol), sodium carbonate (100 mg, 0.95 mmol), palladium (II) acetate (4 mg, 0.018 mmol), and xantphos (18 mg, 0.031 mmol) in toluene (2 ml) was stirred under the atmosphere of carbon monoxide (1.5 bar) at +100° C. for 16 hours then at +120° C. until all the starting bromide was consumed (8 hours). It was flash chromatographed on silica gel (gradient heptane-ethyl acetate) to give 45 mg of the title compound, yield 34%. LC-MS (m/z) 442.4 (MH$^+$); $t_R$=1.15.

Example 5

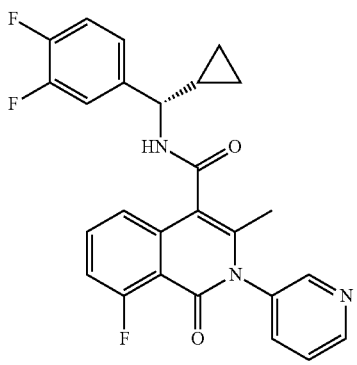 [SMILES: Cc1c(C(=O)N[C@H](c2ccc(F)c(F)c2)C2CC2)c2cccc(F)c2c(=O)n1-c1cccnc1]

5a 8-Fluoro-3-methyl-1-oxo-2-pyridin-3-yl-1,2-dihydro-isoquinoline-4-carboxylic acid [(S)-cyclopropyl-(3,4-difluoro-phenyl)-methyl]-amide 1-Hydroxybenzotriazole (19 mg, 0.14 mmol) and N-(3-dimethylaminopropyl)-N'-ethylcarbodiimide hydrochloride (28 mg, 0.14 mmol) and triethylamine (34 uL, 0.24 mmol) were added to 8-fluoro-3-methyl-1-oxo-2-pyridin-3-yl-1,2-dihydro-isoquinoline-4-carboxylic acid (33 mg, 0.11 mmol) and C-[(S)-C-Cyclopropyl-C-(3,4-difluoro-phenyl)]-methylamine hydrochloride (27 mg) in N,N-Dimethylformamide (1.3 mL). The reaction mixture was stirred at room temperature for 4 hours. The reaction mixture was poured into a mixture of sat. NaHCO$_3$ (aq) and brine (5 mL, 1:1). The mixture was extracted with ethyl acetate (5 mL). The organic phase was washed with brine, dried over MgSO$_4$, filtered through a pad of silica gel and rotavaped. The title compound was isolated by preparative TLC on silica gel with ethyl acetate as an eluent. LC-MS (m/z) 464.4 (MH$^+$); t$_R$=1.12.

The following compounds were obtained analogously:

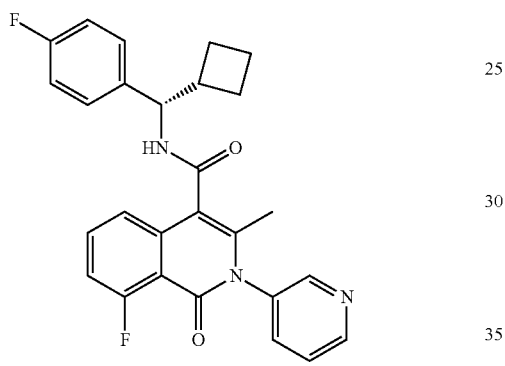

5b 8-Fluoro-3-methyl-1-oxo-2-pyridin-3-yl-1,2-dihydro-isoquinoline-4-carboxylic acid [(S)-cyclobutyl-(4-fluoro-phenyl)-methyl]-amide LC-MS (m/z) 460.6 (MH$^+$); t$_R$=1.19.

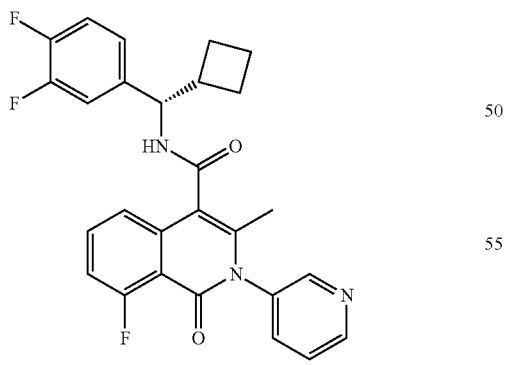

5c 8-Fluoro-3-methyl-1-oxo-2-pyridin-3-yl-1,2-dihydro-isoquinoline-4-carboxylic acid [(S)-cyclobutyl-(3,4-difluoro-phenyl)-methyl]-amide LC-MS (m/z) 478.2 (MH$^+$); t$_R$=1.24.

The following compounds may be obtained analogously:

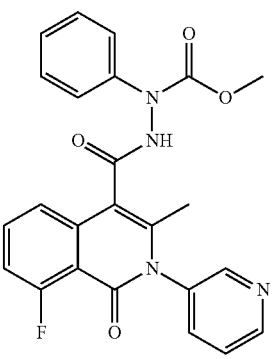 [SMILES: COC(=O)N(NC(=O)c1c(C)n(-c2cccnc2)c(=O)c2c(F)cccc12)c1ccccc1]

5d N'-(3-Methyl-1-oxo-2-pyridin-3-yl-1,2-dihydro-isoquinoline-4-carbonyl)-N-phenyl-hydrazinecarboxylic acid methyl ester

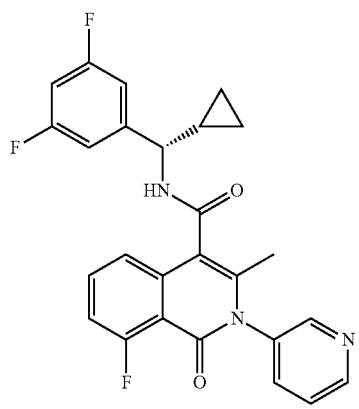 [SMILES: Cc1c(C(=O)N[C@H](c2cc(F)cc(F)c2)C2CC2)c2cccc(F)c2c(=O)n1-c1cccnc1]

5e 8-Fluoro-3-methyl-1-oxo-2-pyridin-3-yl-1,2-dihydro-isoquinoline-4-carboxylic acid [(S)-cyclopropyl-(3,5-difluoro-phenyl)-methyl]-amide LC-MS (m/z) 464.5 (MH$^+$); t$_R$=1.12.

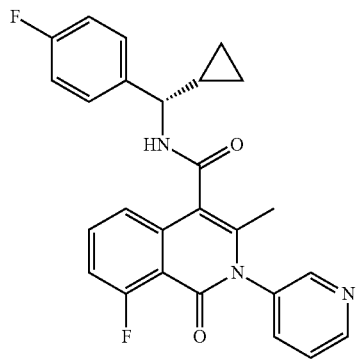 [SMILES: Cc1c(C(=O)N[C@H](c2ccc(F)cc2)C2CC2)c2cccc(F)c2c(=O)n1-c1cccnc1]

5f 8-Fluoro-3-methyl-1-oxo-2-pyridin-3-yl-1,2-dihydro-isoquinoline-4-carboxylic acid [(S)-cyclopropyl-(4-fluoro-phenyl)-methyl]-amide LC-MS (m/z) 446.8 (MH$^+$); $t_R$=1.06.

Example 6

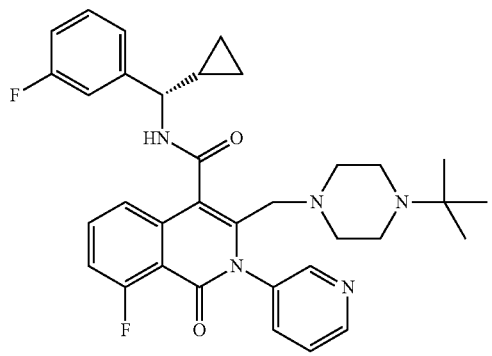 [SMILES: CC(C)(C)N1CCN(Cc2c(C(=O)N[C@H](c3cccc(F)c3)C3CC3)c3cccc(F)c3c(=O)n2-c2cccnc2)CC1]

6a 3-(4-tert-Butyl-piperazin-1-ylmethyl)-8-fluoro-1-oxo-2-pyridin-3-yl-1,2-dihydro-isoquinoline-4-carboxylic acid [(S)-cyclopropyl-(3-fluoro-phenyl)-methyl]-amide 3-Bromomethyl-8-fluoro-1-oxo-2-pyridin-3-yl-1,2-dihydro-isoquinoline-4-carboxylic acid[(S)-cyclopropyl-(3-fluoro-phenyl)-methyl]-amide (118 mg, 0.225 mmol) was dissolved in THF (6 mL) mmol) and 1-tert-butyl-piperazine (64.0 mg, 0.450 mmol) and triethylamine (62 µL, 0.44 mmol) were added. The reaction mixture was stirred overnight at room temperature and concentrated in vacuo. The residue was subjected to preperative TLC on silica gel (eluent: 80% ethyl acetate, 10% methanol, 10% triethylamine). The product-containing fraction was dissolved in methanol and the product precipitated on addition of water. After filtration and drying 3-(4-tert-butyl-piperazin-1-ylmethyl)-8-fluoro-1-oxo-2-pyridin-3-yl-1,2-dihydro-isoquinoline-4-carboxylic acid [(S)-cyclopropyl-(3-fluoro-phenyl)-methyl]-amide was obtained.

LC-MS (m/z) 586.4 (MH$^+$); $t_R$=0.86.

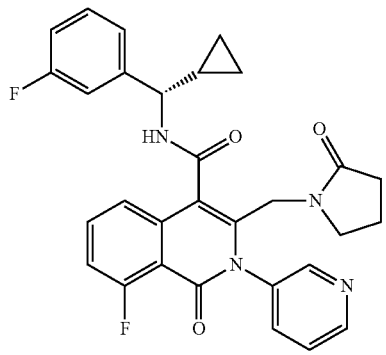 [SMILES: O=C(N[C@H](c1cccc(F)c1)C1CC1)c1c(CN2CCCC2=O)n(-c2cccnc2)c(=O)c2c(F)cccc12]

6b 8-Fluoro-1-oxo-3-(2-oxo-pyrrolidin-1-ylmethyl)-2-pyridin-3-yl-1,2-dihydro-isoquinoline-4-carboxylic acid [(S)-cyclopropyl-(3-fluoro-phenyl)-methyl]-amide Sodium hydride (60% in mineral oil, 72 mg, 1.8 mmol) was added to 2-pyrrolidinone (380 mg, 4.5 mmol) in tetrahydrofuran (2.0 mL) under an atmosphere of Argon. The reaction mixture was stirred for 30 minutes at room temperature. To this mixture, 3-bromomethyl-8-fluoro-1-oxo-2-pyridin-3-yl-1,2-dihydro-isoquinoline-4-carboxylic acid[(S)-cyclopropyl-(3-fluoro-phenyl)-methyl]-amide (118 mg, 0.23 mmol) in tetrahydrofuran (5 mL) was added dropwise. The reaction mixture was stirred for 1 hour at room temperature. The reaction mixture was poured into 25 mL 0.2N HCl (aq). The mixture was extracted with ethyl acetate (25 mL). The organic phase was washed with brine, dried over MgSO$_4$ and concentrated in vacuo. The title compound was isolated by preparative TLC on silica gel (eluent: ethyl acetate).

LC-MS (m/z) 529.5 (MH$^+$); $t_R$=1.01.

Example 7

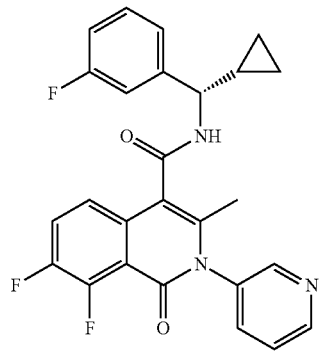 [SMILES: Cc1c(C(=O)N[C@H](c2cccc(F)c2)C2CC2)c2ccc(F)c(F)c2c(=O)n1-c1cccnc1]

7a 4-({[(S)-Cyclopropyl-(3-fluoro-phenyl)-methyl]-amino}-methyl)-7,8-difluoro-3-methyl-2-pyridin-3-yl-2H-isoquinolin-1-one The title compound was prepared as described in the example 2 from 641-{[(S)-cyclopropyl-(3-fluoro-phenyl)-methyl]-carbamoyl}-2-oxo-propyl)-2,3-difluoro-benzoic acid and 3-aminopyridine (acetonitrile, 90° C., 16 hours) and purified by preparative LC-MS.

LC-MS (m/z) 464.5 (MH$^+$); $t_R$=1.23.

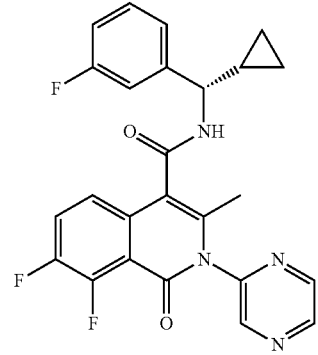 [SMILES: Cc1c(C(=O)N[C@H](c2cccc(F)c2)C2CC2)c2ccc(F)c(F)c2c(=O)n1-c1cnccn1]

7b 7,8-Difluoro-3-methyl-1-oxo-2-pyrazin-2-yl-1,2-dihydro-isoquinoline-4-carboxylic acid [(S)-cyclopropyl-(3-fluoro-phenyl)-methyl]-amide The title compound was prepared analogously using 2-aminopyrazine (acetonitrile 120° C., 16 hours). LC-MS (m/z) 465.5 (MH+); $t_R$=1.31.

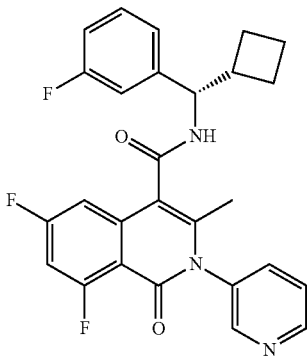 [SMILES: Cc1c(C(=O)N[C@H](c2cccc(F)c2)C2CCC2)c2cc(F)cc(F)c2c(=O)n1-c1cccnc1]

7c 6,8-Difluoro-3-methyl-1-oxo-2-pyridin-3-yl-1,2-dihydro-isoquinoline-4-carboxylic acid [(S)-cyclobutyl-(3-fluoro-phenyl)-methyl]-amide The title compound was prepared analogously from 2-(1-{[(S)-Cyclobutyl-(3-fluoro-phenyl)-methyl]-carbamoyl}-2-oxo-propyl)-4,6-difluoro-benzoic acid and 3-aminopyridine (acetonitrile 90° C., 16 hours). LC-MS (m/z) 478.1 (MH+); $t_R$=1.27.

Example 8

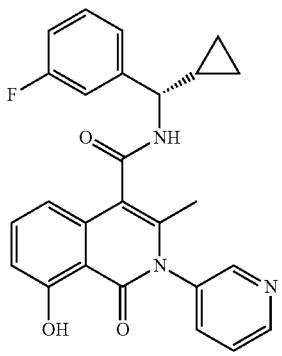 [SMILES: Cc1c(C(=O)N[C@H](c2cccc(F)c2)C2CC2)c2cccc(O)c2c(=O)n1-c1cccnc1]

8a 8-Hydroxy-3-methyl-1-oxo-2-pyridin-3-yl-1,2-dihydro-isoquinoline-4-carboxylic acid [(S)-cyclopropyl-(3-fluoro-phenyl)-methyl]-amide A mixture of 8-fluoro-3-methyl-1-oxo-2-pyridin-3-yl-1,2-dihydro-isoquinoline-4-carboxylic acid [(S)-cyclopropyl-(3-fluoro-phenyl)-methyl]-amide (2a, 70.0 mg, 0.157 mmol), sodium nitrite (NaNO$_2$, 77.0 mg, 1.12 mmol) in N,N-dimethylformamide (0.7 mL) was heated under microwave irradiation at 220° C. for 30 min. The obtained dark solution was quenched with 3M aq. HCl (5 ml), stirred for 20 min and partitioned with ethyl acetate (3×5 mL). Each organic solution was washed with 1M HCl (3×2 mL). The combined aq. solution was basified with NaHCO$_3$ (pH=7) and extracted with ethyl acetate. The combined organic extracts were absorbed on 1 g SiO$_2$ and flash chromatographed on 20 g silica gel with gradient heptane-ethyl acetate. The product came out with 75% ethyl acetate and only pure fractions were evaporated to give 7.1 mg of a brown residue, yield 10%. LC-MS (m/z) 444.6 (MH+); $t_R$=1.26. $^1$H NMR (500 MHz, 70° C., DMSO-d$_6$): 0.48 & 0.59 (two br. s, 2×2H, two CH$_2$ of Cp), 1.27 (br. s, 1H, CH of Cp), 1.91 (br. s, 3H, Me), 4.51 (t, J=8.5 Hz, 1H, CHNH), 6.87 (overlapping d, J=8.1 Hz, 1H), 6.9 (overlapping br. s, 1H), 7.06 (br. T, J=8.3 Hz, 1H), 7.26 (d, J=10.5 Hz, 1H), 7.3 (d, J=7.6 Hz, 1H), 7.40 (q, J=7.2 Hz, 1H), 7.59-7.66 (br. m, 2H), 7.86 (br. m, 1H), 8.58 (s, 1H), 8.72 (s, 1H), 8.93 (br. d, J=7.8 Hz, NHCO), 12.46 (s, 1H, OH).

Reagents used for the preparation of the compounds.

| Name | Supplier | CAS no. | Cat. no. |
|---|---|---|---|
| (S)-(−)-1-Phenylpropylamine | Lancaster | 3789-59-1 | X16320G0025 |
| C-[(S)-C-Cyclopropyl-C-(3-fluorophenyl)]-methylamine | The compound was prepared according to a described procedure in WO 2005/014575 | | |
| 1-Ethyl-3-(3-dimethylaminopropyl)carbodiimide hydrochloride (EDC) | Aldrich | 25952-53-8 | 16,146-2 |
| 1-Hydroxybenzotriazole (HOBT) | ABCR | 2592-95-2 | AV21700 |
| Homophthalic anhydride | ABCR | 703-59-3 | AV15538 |
| Cyclopropanecarboxaldehyde | Aldrich | 1489-69-6 | 27,221-3 |
| 1-Bromo-3-fluorobenzene | Aldrich | 1073-06-9 | B67007 |
| Xantphos (=4,5-bis(diphenylphosphino)-9,9-dimethylxanthene) | Aldrich | 161265-03-8 | 52,646-0 |
| N-bromosuccinimide | Aldrich | 128-08-5 | B8,125-5 |
| N-tert-butylpiperazine | 3B-Medical | 38216-72-7 | 3B-2316 |
| 2-pyrrolidinone | Aldrich | 616-45-5 | P7,437-0 |
| Sodium hydride | Aldrich | 7646-69-7 | 45,291-2 |
| Bromine | Merck | 7726-95-6 | 101948 |

Aminoheterocycles of the general formula VI used for the preparation of the compounds.

| Name | Supplier | CAS no. | Cat. no. |
|---|---|---|---|
| 3-Aminopyridine | Aldrich | 462-08-8 | A7,820-9 |
| 4-Amino-1,2,4-triazole | Aldrich | 584-13-4 | A8,180-3 |
| 3-Aminothiophene | Synchem | 17721-06-1 | UN070 |
| 2-Aminopyridine | Aldrich | 504-29-0 | A7,799-7 |
| 2-Aminopyrazine | Aldrich | 5049-61-6 | A76958 |
| 5-Amino-2-chloropyridine | Aldrich | 5350-93-6 | 18,877-8 |
| 5-Amino-2-methoxypyridine | Aldrich | 6628-77-9 | A6,120-9 |
| 2,3-Diaminopyridine | Aldrich | 452-58-4 | 12,585-7 |
| 6-(4-Methoxyphenyl)-3-pyridinamine | Bionet | — | 4Y-0705 |
| 2-(4-Methoxyphenyl)-3-pyridinamine | Bionet | — | 5Y-0701 |
| 2-Morpholino-3-pyridinamine | Maybridge | — | CC 24614 |
| 3-Amino-2-fluoropyridine | Matrix Scientific | 1597-33-7 | 18275 |
| 5-Aminopyrimidine | AK Scientific | 591-55-9 | 66197 |
| 3-Amino-6-picoline | Aldrich | 3430-14-6 | 662704 |
| 3-Amino-2-picoline | Aldrich | 3430-10-2 | 662690 |
| 5-Amino-2-fluoropyridine | Apollo | 1827-27-6 | PC9133 |
| 3-Amino-4-methylpyridine | Apollo | 3430-27-1 | OR2023 |
| 3-Amino-5-methylpyridine | Apollo | 3430-19-1 | OR7004 |
| 6-Phenoxy-3-pyridinamine | Maybridge | — | CC19614 |
| 2-Amino-4-methylthiazole | Aldrich | 1603-91-4 | A66006 |
| 1,3-Dimethyl-1H-pyrazol-4-ylamine hydrochloride | ACB | — | MIX-0196 |

-continued

| Name | Supplier | CAS no. | Cat. no. |
|---|---|---|---|
| 2-Methyl-1H-imidazole-1-amine | CgeneTech | 51741-29-8 | 50047 |
| 2-Amino-5-ethyl-1,3,4-thiadiazole | Aldrich | 14068-53-2 | 19,692-4 |
| 2-Aminothiazole | Avocado | 96-50-4 | 12026 |
| 2-Aminobenzimidazole | Aldrich | 934-32-7 | 17,177-8 |
| 4-Amino-3,5-dimethyl-1,2,4-triazole | Alfa | 3530-15-2 | B20417 |
| 5-Amino-1,3-dimethylpyrazole | Aldrich | 3524-32-1 | 53,222-3 |
| 3-Amino-5-methylisoxazole | Aldrich | 1072-67-9 | 232270 |
| 2-Amino-5-methyl-1,3,4-thiadiazole | Aldrich | 108-33-8 | 686166 |
| 1-Aminopyrrole | TCI-Europe | 765-39-9 | A1022 |
| 2-Amino-5-methylthiazole | Aldrich | 7305-71-7 | 38,056-3 |
| 2-Amino-3-thiophenecarbonitrile | Fluorochem | 4651-82-5 | 017505 |
| 3-Aminoisoxazole | Aldrich | 1750-42-1 | 424218 |
| 1-Methyl-1H-pyrazol-3-amine | Apollo | 1904-31-0 | OR24245 |
| 5-Amino-2-bromopyridine | Aldrich | 13534-97-9 | 552844 |

Example 9

NK3 Receptor Binding Assay

Membrane preparation: BHK cells stably expressing the human NK3 receptor were seeded in harvesting plates in Dulbeccos MEM containing GlutaMax (862 mg/l), 1 mM sodium pyruvate, 10% fetal calf serum, 1% Pen/Strep, 1 mg/ml G418 and were grown at 34° C. in a humidified atmosphere containing 10% $CO_2$. To increase receptor expression, 10 μM trichotatin A was added to the media 24 hours before harvest of the cells at a confluency of app 90%. Prior to the harvesting, the cells were washed twice with PBS without $Mg^{2+}$ og $Ca^{2+}$ and subsequently scrapped of in 10 ml PBS pr harvesting plate. The cells suspension were centrifuged at 1500×G in three minutes before resuspension in 15 mM Tris-HCl pH 7.5 buffer containing 2 mM $MgCl_2$; 0.3 mM EDTA and 1 mM EGTA (buffer A). The cell suspension was homogenised and subsequently centrifuged at 40000×G in 30 minutes. The membrane-pellet was resuspended in buffer A containing 250 mM sucrose, aliquoted and stored at −80° C.

Affinity assay description: The assay was performed as a SPA-based competition-binding assay in a 50 mM Tris pH 7.4 assay buffer containing 120 mM NaCl, 3 mM $MnCl_2$, 40 μg/ml bacitracin, 2 μg/ml Chymostatin, 1 μg/ml Phosphoramidon and 4 μg/ml Leupeptin. App 0.02 nM $^{125}$I-NKB was mixed with test compounds before addition of 4 μg of the homogenised NK3 membrane preparation and 0.025 mg SPA beads in a total volume of 60 μl. The assay plate was subsequently under agitation incubated for 90 min at RT. The plate was centrifugated 10 minutes at 500×G and counted in a topcounter 5 minutes pr well.

The total binding, which comprised less than 5% of added radioligand, was defined using assay buffer whereas the non-specific binding was defined in the presence of 1 μM osanetant. The non-specific binding constituted app 5% of the total binding.

Data points were expressed in percent of the specific binding of $^{125}$I-NKB and the $IC_{50}$ values (concentration causing 50 percent inhibition of $^{125}$I-NKB specific binding) were determined by non-linear regression analysis using a sigmoidal variable slope curve fitting. The dissociation constant ($K_i$) were calculated from the Cheng Prusoff equation ($K_i = IC_{50}/(1+(L/K_D))$), where the concentration of free radioligand L is approximated to the concentration of added $^{125}$I-NKB in the assay (app 0.02 nM). The $K_D$ of $^{125}$I-NKB was determined to be 0.7 nM from three independent saturation assays each performed with duplicate determinations. Bmax was app 2 pmol/mg.

The compounds of the present invention generally have $K_i$ values of 500 nM or less. Many compounds, in fact, have $K_i$ values below 100 nM and down to single digit values.
The table below shows the $K_i$ for the NK3 receptor

| example # in the patent | Affinity Ki/nM |
|---|---|
| 2b | 150 |
| 2d | 120 |
| 2k | 110 |
| 2l | 220 |
| 2r | 150 |
| 2u | 200 |
| 2v | 210 |
| 2ac | 96 |
| 4a | 18 |
| 3f | 71 |
| 6a | 13 |
| 6b | 110 |
| 7c | 15 |
| 8a | 33 |

Example 10

NK3 Receptor Efficacy and Potency Assay

BHK cells stably expressing the human NK3 receptor were seeded in 100 μl media in black walled clear-base 96-wells plates (Costar) aiming at a confluency of 95-100% at the day of assay. The assay was performed according to the FLIPR Calcium 4 Assay kit (Molecular Devices). At the day of the assay, the media was removed and the cells were washed once with the HBSS buffer (Hanks BSS buffer, pH 7.4 containing 20 mM Hepes) before 100 μl of a solution of the calcium assay reagent dissolved in the HBSS buffer containing 2.5 mM probinicid was added to the cells. The plates were incubated for 60 min at 34° C., 10% $CO_2$ before use in the FLIPR for examination of fluorescence.

One representative plate was examined with a dose-response curve with NKB in a setup in which the wells initially were added HBSS buffer and 15 min later the various concentrations of NKB were added in order to determine the $EC_{50}$ and $EC_{85}$ of NKB. All compound plates used for NKB were precoated with a 1% BSA solution and subsequently washed three times with $H_2O$, NKB was diluted in HBSS buffer containing 0.1% BSA.

For efficacy and potency evaluation of compounds, these were diluted in HBSS buffer prior to test. For test of agonist activity, 25 μl of the diluted compound solution was added and the plate was analyzed for 5 minutes in the FLIPR. For test of antagonist activity, the plate was incubated for another 45 minutes before addition of 25 μl of the $EC_{85}$ concentration of NKB (app. 4 nM) as described above. The plates were subsequently analyzed for 5 minutes before the assay was terminated. The maximal increase in fluorescence over background following each ligand addition was determined. The $IC_{50}$ value was calculated using sigmoidal variable slope curve fitting, and the $cIC_{50}$ value was determined using the equation ($cIC_{50} = IC_{50}/(1+(EC_{85}/EC_{50}))$), where $EC_{85}$ and $EC_{50}$ for NKB were determined as described above.

All isoquinolinones of the present invention characterized in the NK3 receptor efficacy and potency assay have been antagonists without any observed significant agonist activity at relevant doses.

The invention claimed is:

1. A compound according to formula I

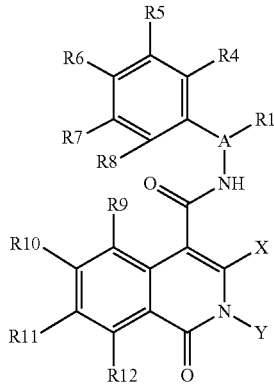

wherein A is N, CH or CR$^1$;
each R$^1$ is independently hydrogen, C$_{1-6}$alkyl, C$_{2-6}$alkenyl, C$_{2-6}$alkynyl, —C(O)—C$_{1-6}$alkyl, —C(O)—C$_{2-6}$alkenyl, —C(O)—C$_{2-6}$alkynyl, —C(O)—O—C$_{1-6}$alkyl, —C(O)—O—C$_{2-6}$alkenyl, —C(O)—O—C$_{2-6}$alkynyl, or phenyl, wherein said phenyl, C$_{1-6}$alkyl, C$_{2-6}$alkenyl or C$_{2-6}$alkynyl is optionally substituted with one or more substituents selected from the group consisting of halogen, hydroxyl, haloC$_{1-6}$alkyl, nitro, C$_{1-6}$alkoxy, and NR$^2$R$^3$;
X is hydrogen, C$_{1-6}$alkyl or —CR$^a$R$^b$—X', wherein X' is a monocyclic saturated moiety having 5-6 ring atoms, one of which is N and wherein one or two additional ring atoms may be a hetero atom selected from the group consisting of N, O and S, which monocyclic ring may be substituted with one or more substituents W, wherein W is selected from the group consisting of C$_{1-6}$alkyl, C$_{2-6}$alkenyl, C$_{2-6}$alkynyl, and (=O);
R$^a$ and R$^b$ are each independently hydrogen, —CH$_3$ or halogen;
Y is a hetero aromatic moiety having 5-6 ring atoms, wherein 1-4 of said ring atoms are selected from the group consisting of N, O and S, which hetero aromatic moiety may optionally be benzofused, and which hetero aromatic moiety may be substituted with one or more substituents Z, wherein Z is selected from the group consisting of C$_{1-6}$alkyl, C$_{2-6}$alkenyl, C$_{2-6}$alkynyl, cyano, halogen, hydroxy, C$_{1-6}$alkoxy, C$_{1-6}$haloalkyl, and NR$^2$R$^3$; wherein
each of R$^2$ and R$^3$ are independently hydrogen, C$_{1-6}$alkyl, C$_{2-6}$alkenyl, C$_{2-6}$alkynyl, hydroxyC$_{1-6}$alkyl, or haloC$_{1-6}$alkyl;
each of R$^4$-R$^8$ and R$^9$-R$^{12}$ are independently hydrogen, C$_{1-6}$alkyl, C$_{2-6}$alkenyl, C$_{2-6}$alkynyl, halogen, NR$^2$R$^3$, hydroxy, cyano, nitro, C$_{1-6}$alkoxy, haloC$_{1-6}$alkyl or hydroxyC$_{1-6}$alkyl;
or a pharmaceutically acceptable salt thereof.

2. The compound according to claim 1, wherein A is CH.

3. The compound according to claim 1, wherein R$^1$ is C$_{1-6}$alkyl.

4. The compound according to claim 3, wherein R$^1$ is ethyl, cyclopropyl, or cyclobutyl.

5. The compound according to claim 1, wherein X is H, methyl or —CH$_2$—X', wherein X' is a monocyclic moiety selected from the group consisting of piperazinyl and pyrrolidinyl, wherein said monocyclic moiety may be substituted with one or more substituents W, wherein W is selected from the group consisting of C$_{1-6}$alkyl and (=O).

6. The compound according to claim 1, wherein Y is a hetero aromatic moiety having 5-6 ring atoms, wherein 1-3 of said ring atoms are selected from the group consisting of N, O and S, and which hetero aromatic moiety may be substituted with one or more substituents Z, wherein Z is selected from the group consisting of C$_{1-6}$alkyl, cyano, halogen C$_{1-6}$alkoxy, and NR$^2$R$^3$; wherein each of R$^2$ and R$^3$ are independently hydrogen or C$_{1-6}$alkyl.

7. The compound according to claim 6, wherein Y is 4H-[1,2,4]triazolyl, thienyl, thiazolyl, 1H-pyrazolyl, 1H-imidazolyl, [1,3,4]thiadiazolyl, thiazolyl, isoxazolyl, pyrrolyl, pyridyl, or pyrazinyl.

8. The compound according to claim 1, wherein R$^4$-R$^8$ are each independently hydrogen or halogen.

9. The compound according to claim 8, wherein R$^7$ is halogen, and R$^4$, R$^5$, and R$^8$ are each hydrogen.

10. The compound according to claim 1, wherein R$^9$-R$^{12}$ are each independently hydrogen or halogen.

11. The compound according to claim 10, wherein R$^9$-R$^{11}$ are each hydrogen, and R$^{12}$ is halogen.

12. The compound according to claim 1, represented by formula I'

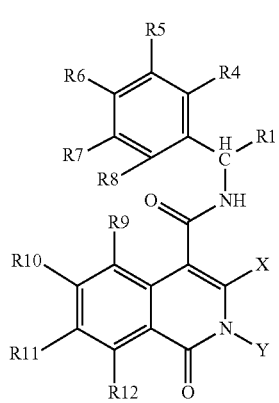

wherein R$^1$ is C$_{1-6}$alkyl;
X is hydrogen, C$_{1-6}$alkyl or —CH$_2$—X', wherein X' is piperazinyl or pyrrolidinyl, wherein said piperazinyl or pyrrolidinyl may be substituted with one or more substituents W, wherein W is selected from the group consisting of C$_{1-6}$alkyl and (=O);
wherein Y is a hetero aromatic moiety having 5-6 ring atoms, wherein 1-4 of said ring atoms are selected from the group consisting of N, O and S, which hetero aromatic moiety may optionally be benzo-fused, and which hetero aromatic moiety may be substituted with one or more substituents Z, wherein Z is selected from the group consisting of C$_{1-6}$alkyl, cyano, halogen, hydroxy, C$_{1-6}$alkoxy, C$_{1-6}$haloalkyl, and NR$^2$R$^3$; wherein each of R$^2$ and R$^3$ are independently hydrogen or C$_{1-6}$alkyl;
each of R$^4$-R$^8$ and R$^9$-R$^{12}$ are independently hydrogen, halogen, C$_{1-6}$alkoxy or C$_{1-6}$haloalkyl;
or a pharmaceutically acceptable salt thereof.

13. The compound according to claim 12, wherein R$^1$ is ethyl, cyclopropyl, or cyclobutyl.

14. The compound according to claim 12, wherein R$^1$ is ethyl, cyclopropyl, or cyclobutyl; X is C$_{1-6}$alkyl;
Y is a hetero aromatic moiety having 5-6 ring atoms, wherein 1-4 of said ring atoms are selected from the group consisting of N, O and S, and which hetero aromatic moiety may be substituted with one or more substituents Z, wherein Z is selected from the group consisting of $C_{1-6}$alkyl, cyano, halogen, hydroxy, $C_{1-6}$alkoxy, $C_{1-6}$haloalkyl, and $NR^2R^3$;
wherein each of $R^2$ and $R^3$ are independently hydrogen or $C_{1-6}$alkyl;
$R^4$-$R^8$ are independently hydrogen or halogen; and $R^9$-$R^{12}$ are independently hydrogen or halogen.

15. The compound according to claim 14, wherein $R^7$ is halogen, and $R^4$, $R^5$, and $R^8$ are each hydrogen; and $R^9$-$R^{11}$ are each hydrogen and $R^{12}$ is halogen.

16. The compound according to claim 15, wherein Y is 4H-[1,2,4]triazolyl, thienyl, thiazolyl, 1H-pyrazolyl, 1H-imidazolyl, [1,3,4]thiadiazolyl, thiazolyl, isoxazolyl, pyrrolyl, pyridyl, or pyrazinyl.

17. A compound according to claim 1 selected from the group consisting of:
  3-Methyl-1-oxo-2-pyridin-3-yl-1,2-dihydro-isoquinoline-4-carboxylic acid ((S)-1-phenyl-propyl)-amide;
  3-Methyl-1-oxo-2-[1,2,4]triazol-4-yl-1,2-dihydro-isoquinoline-4-carboxylic acid ((S)-1-phenyl-propyl)-amide;
  3-Methyl-1-oxo-2-thiophen-3-yl-1,2-dihydro-isoquinoline-4-carboxylic acid ((S)-1-phenyl-propyl)-amide;
  8-Fluoro-3-methyl-1-oxo-2-pyridin-3-yl-1,2-dihydro-isoquinoline-4-carboxylic acid [(S)-cyclopropyl-(3-fluoro-phenyl)-methyl]-amide;
  8-Fluoro-3-methyl-2-(5-methyl-isoxazol-3-yl)-1-oxo-1,2-dihydro-isoquinoline-4-carboxylic acid [(S)-cyclopropyl-(3-fluoro-phenyl)-methyl]-amide;
  8-Fluoro-3-methyl-2-(5-methyl-[1,3,4]thiadiazol-2-yl)-1-oxo-1,2-dihydro-isoquinoline-4-carboxylic acid [(S)-cyclopropyl-(3-fluoro-phenyl)-methyl]-amide;
  8-Fluoro-3-methyl-1-oxo-2-pyrrol-1-yl-1,2-dihydro-isoquinoline-4-carboxylic acid [(S)-cyclopropyl-(3-fluoro-phenyl)-methyl]-amide;
  8-Fluoro-3-methyl-2-(5-methyl-thiazol-2-yl)-1-oxo-1,2-dihydro-isoquinoline-4-carboxylic acid [(S)-cyclopropyl-(3-fluoro-phenyl)-methyl]-amide;
  2-(3-Cyano-thiophen-2-yl)-8-fluoro-3-methyl-1-oxo-1,2-dihydro-isoquinoline-4-carboxylic acid [(S)-cyclopropyl-(3-fluoro-phenyl)-methyl]-amide;
  8-Fluoro-2-isoxazol-3-yl-3-methyl-1-oxo-1,2-dihydro-isoquinoline-4-carboxylic acid [(S)-cyclopropyl-(3-fluoro-phenyl)-methyl]-amide;
  8-Fluoro-3-methyl-1-oxo-2-pyridin-2-yl-1,2-dihydro-isoquinoline-4-carboxylic acid [(S)-cyclopropyl-(3-fluoro-phenyl)-methyl]-amide;
  8-Fluoro-3-methyl-1-oxo-2-pyrazin-2-yl-1,2-dihydro-isoquinoline-4-carboxylic acid [(S)-cyclopropyl-(3-fluoro-phenyl)-methyl]-amide;
  2-(6-Chloro-pyridin-3-yl)-8-fluoro-3-methyl-1-oxo-1,2-dihydro-isoquinoline-4-carboxylic acid [(S)-cyclopropyl-(3-fluoro-phenyl)-methyl]-amide;
  8-Fluoro-2-(6-methoxy-pyridin-3-yl)-3-methyl-1-oxo-1,2-dihydro-isoquinoline-4-carboxylic acid [(S)-cyclopropyl-(3-fluoro-phenyl)-methyl]-amide;
  2-(2-Amino-pyridin-3-yl)-8-fluoro-3-methyl-1-oxo-1,2-dihydro-isoquinoline-4-carboxylic acid [(S)-cyclopropyl-(3-fluoro-phenyl)-methyl]-amide;
  8-Fluoro-2-[6-(4-methoxy-phenyl)-pyridin-3-yl]-3-methyl-1-oxo-1,2-dihydro-isoquinoline-4-carboxylic acid [(S)-cyclopropyl-(3-fluoro-phenyl)-methyl]-amide;
  8-Fluoro-3-methyl-1-oxo-2-pyrimidin-5-yl-1,2-dihydro-isoquinoline-4-carboxylic acid [(S)-cyclopropyl-(3-fluoro-phenyl)-methyl]-amide;
  8-Fluoro-3-methyl-2-(6-methyl-pyridin-3-yl)-1-oxo-1,2-dihydro-isoquinoline-4-carboxylic acid [(S)-cyclopropyl-(3-fluoro-phenyl)-methyl]-amide;
  8-Fluoro-3-methyl-2-(2-methyl-pyridin-3-yl)-1-oxo-1,2-dihydro-isoquinoline-4-carboxylic acid [(S)-cyclopropyl-(3-fluoro-phenyl)-methyl]-amide;
  8-Fluoro-2-(6-fluoro-pyridin-3-yl)-3-methyl-1-oxo-1,2-dihydro-isoquinoline-4-carboxylic acid [(S)-cyclopropyl-(3-fluoro-phenyl)-methyl]-amide;
  8-Fluoro-3-methyl-2-(4-methyl-pyridin-3-yl)-1-oxo-1,2-dihydro-isoquinoline-4-carboxylic acid [(S)-cyclopropyl-(3-fluoro-phenyl)-methyl]-amide;
  8-Fluoro-3-methyl-2-(5-methyl-pyridin-3-yl)-1-oxo-1,2-dihydro-isoquinoline-4-carboxylic acid [(S)-cyclopropyl-(3-fluoro-phenyl)-methyl]-amide;
  8-Fluoro-3-methyl-2-(4-methyl-thiazol-2-yl)-1-oxo-1,2-dihydro-isoquinoline-4-carboxylic acid [(S)-cyclopropyl-(3-fluoro-phenyl)-methyl]-amide;
  2-(1,3-Dimethyl-1H-pyrazol-4-yl)-8-fluoro-3-methyl-1-oxo-1,2-dihydro-isoquinoline-4-carboxylic acid [(S)-cyclopropyl-(3-fluoro-phenyl)-methyl]-amide;
  8-Fluoro-3-methyl-2-(2-methyl-imidazol-1-yl)-1-oxo-1,2-dihydro-isoquinoline-4-carboxylic acid [(S)-cyclopropyl-(3-fluoro-phenyl)-methyl]-amide;
  8-Fluoro-3-methyl-1-oxo-2-[1,2,4]triazol-4-yl-1,2-dihydro-isoquinoline-4-carboxylic acid [(S)-cyclopropyl-(3-fluoro-phenyl)-methyl]-amide;
  2-(5-Ethyl-[1,3,4]thiadiazol-2-yl)-8-fluoro-3-methyl-1-oxo-1,2-dihydro-isoquinoline-4-carboxylic acid [(S)-cyclopropyl-(3-fluoro-phenyl)-methyl]-amide;
  8-Fluoro-3-methyl-1-oxo-2-thiazol-2-yl-1,2-dihydro-isoquinoline-4-carboxylic acid [(S)-cyclopropyl-(3-fluoro-phenyl)-methyl]-amide;
  2-(1H-Benzoimidazol-2-yl)-8-fluoro-3-methyl-1-oxo-1,2-dihydro-isoquinoline-4-carboxylic acid [(S)-cyclopropyl-(3-fluoro-phenyl)-methyl]-amide;
  2-(3,5-Dimethyl-[1,2,4]triazol-4-yl)-8-fluoro-3-methyl-1-oxo-1,2-dihydro-isoquinoline-4-carboxylic acid [(S)-cyclopropyl-(3-fluoro-phenyl)-methyl]-amide;
  2-(2,5-Dimethyl-2H-pyrazol-3-yl)-8-fluoro-3-methyl-1-oxo-1,2-dihydro-isoquinoline-4-carboxylic acid [(S)-cyclopropyl-(3-fluoro-phenyl)-methyl]-amide;
  8-Fluoro-3-methyl-1-oxo-2-pyridin-3-yl-1,2-dihydro-isoquinoline-4-carboxylic acid [(S)-cyclobutyl-(3-fluoro-phenyl)-methyl]-amide;
  8-Fluoro-3-methyl-1-oxo-2-pyrazin-2-yl-1,2-dihydro-isoquinoline-4-carboxylic acid [(S)-cyclobutyl-(3-fluoro-phenyl)-methyl]-amide;
  8-Fluoro-3-methyl-2-(5-methyl-isoxazol-3-yl)-1-oxo-1,2-dihydro-isoquinoline-4-carboxylic acid [(S)-cyclobutyl-(3-fluoro-phenyl)-methyl]-amide;
  8-Fluoro-2-(6-hydroxy-pyridin-3-yl)-3-methyl-1-oxo-1,2-dihydro-isoquinoline-4-carboxylic acid [(S)-cyclobutyl-(3-fluoro-phenyl)-methyl]-amide;
  8-Fluoro-3-methyl-1-oxo-2-pyridin-3-yl-1,2-dihydro-isoquinoline-4-carboxylic acid ((S)-cyclobutyl-phenyl-methyl)-amide;
  8-Fluoro-3-methyl-1-oxo-2-pyridin-3-yl-1,2-dihydro-isoquinoline-4-carboxylic acid [(S)-cyclopropyl-(3,4-difluoro-phenyl)-methyl]-amide;
  8-Fluoro-3-methyl-1-oxo-2-pyridin-3-yl-1,2-dihydro-isoquinoline-4-carboxylic acid [(S)-cyclobutyl-(4-fluoro-phenyl)-methyl]-amide;
  8-Fluoro-3-methyl-1-oxo-2-pyridin-3-yl-1,2-dihydro-isoquinoline-4-carboxylic acid [(S)-cyclobutyl-(3,4-difluoro-phenyl)-methyl]-amide;

3-(4-tert-Butyl-piperazin-1-ylmethyl)-8-fluoro-1-oxo-2-pyridin-3-yl-1,2-dihydro-isoquinoline-4-carboxylic acid [(S)-cyclopropyl-(3-fluoro-phenyl)-methyl]-amide;

8-Fluoro-1-oxo-3-(2-oxo-pyrrolidin-1-ylmethyl)-2-pyridin-3-yl-1,2-dihydro-isoquinoline-4-carboxylic acid [(S)-cyclopropyl-(3-fluoro-phenyl)-methyl]-amide;

4-({[(S)-Cyclopropyl-(3-fluoro-phenyl)-methyl]-amino}-methyl)-7,8-difluoro-3-methyl-2-pyridin-3-yl-2H-isoquinolin-1-one;

N'-(3-Methyl-1-oxo-2-pyridin-3-yl-1,2-dihydro-isoquinoline-4-carbonyl)-N-phenyl-hydrazinecarboxylic acid methyl ester;

7,8-Difluoro-3-methyl-1-oxo-2-pyrazin-2-yl-1,2-dihydro-isoquinoline-4-carboxylic acid [(S)-cyclopropyl-(3-fluoro-phenyl)-methyl]-amide;

8-Fluoro-3-methyl-1-oxo-2-pyridin-3-yl-1,2-dihydro-isoquinoline-4-carboxylic acid [(S)-cyclopropyl-(3,5-difluoro-phenyl)-methyl]-amide;

8-Fluoro-3-methyl-1-oxo-2-pyridin-3-yl-1,2-dihydro-isoquinoline-4-carboxylic acid [(S)-cyclopropyl-(4-fluoro-phenyl)-methyl]-amide;

6,8-Difluoro-3-methyl-1-oxo-2-pyridin-3-yl-1,2-dihydro-isoquinoline-4-carboxylic acid [(S)-cyclobutyl-(3-fluoro-phenyl)-methyl]-amide;

2-(6-Bromo-pyridin-3-yl)-8-fluoro-3-methyl-1-oxo-1,2-dihydro-isoquinoline-4-carboxylic acid [(S)-cyclobutyl-(3-fluoro-phenyl)-methyl]-amide;

8-Fluoro-3-methyl-2-(1-methyl-1H-pyrazol-3-yl)-1-oxo-1,2-dihydro-isoquinoline-4-carboxylic acid [(S)-cyclopropyl-(3-fluoro-phenyl)-methyl]-amide;

8-Fluoro-3-methyl-2-(1-methyl-1H-pyrazol-3-yl)-1-oxo-1,2-dihydro-isoquinoline-4-carboxylic acid [(S)-cyclobutyl-(3-fluoro-phenyl)-methyl]-amide; and 8-Hydroxy-3-methyl-1-oxo-2-pyridin-3-yl-1,2-dihydro-isoquinoline-4-carboxylic acid [(S)-cyclopropyl-(3-fluoro-phenyl)-methyl]-amide.

18. A method for the treatment of a disease selected from the group consisting of consisting of psychosis; schizophrenia; schizophrenoform disorder; schizoaffective disorder; delusional disorder; brief psychotic disorder; shared psychotic disorder; psychotic disorder due to a general medical condition; substance or drug induced psychotic disorder; schizoid personality disorder; schizoptypal personality disorder; psychosis or schizophrenia associated with major depression, bipolar disorder, Alzheimer's disease or Parkinson's disease; major depression; general anxiety disorder; bipolar disorder; mania; hypomania; cognitive impairment; ADHD; obesity; appetite reduction; Alzheimer's disease; Parkinson's disease; pain; convulsions; cough; asthma; airway hyperresponsiveness; microvascular hypersensitivity; bronchoconstriction; chronic obstructive pulmonary disease; urinary incontinence; gut inflammation; post traumatic stress disorder; dementia; agitation and delirium in elderly; and inflammatory bowel syndrome, the method comprising the administration of a therapeutically effective amount of a compound according to claim 1 to a patient in need thereof.

19. The method according to claim 18, wherein said disease is schizophrenia, 20. The method according to claim 19, wherein the positive, negative and/or cognitive symptoms of schizophrenia are treated.

21. The method according to claim 18 wherein the substance or drug induced psychotic disorder is cocaine, alcohol, or amphetamine.

22. The method according to claim 18 wherein the bipolar disorder is maintenance treatment, recurrence prevention and stabilization.

23. A pharmaceutical composition comprising a compound according to claim 1 in combination with one or more pharmaceutically acceptable carrier or excipient.

* * * * *

UNITED STATES PATENT AND TRADEMARK OFFICE
CERTIFICATE OF CORRECTION

PATENT NO. : 8,415,356 B2
APPLICATION NO. : 12/997282
DATED : April 9, 2013
INVENTOR(S) : Khanzhin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 196 days.

Signed and Sealed this
Eighth Day of April, 2014

Michelle K. Lee
*Deputy Director of the United States Patent and Trademark Office*